(12) United States Patent
Mehansho et al.

(10) Patent No.: US 11,007,171 B2
(45) Date of Patent: *May 18, 2021

(54) TREATMENT AND PREVENTION OF JOINT DISORDERS

(71) Applicant: Summit Innovation Labs, LLC, Norwood, OH (US)

(72) Inventors: Haile Mehansho, Hamilton, OH (US); Satyanarayana Majeti, Liberty Township, OH (US); Ghebre Egziabher Tzeghai, Wyoming, OH (US)

(73) Assignee: Summit Innovation Labs, LLC, Norwood, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/050,069

(22) Filed: Jul. 31, 2018

(65) Prior Publication Data
US 2019/0015384 A1 Jan. 17, 2019

Related U.S. Application Data

(63) Continuation-in-part of application No. 15/649,084, filed on Jul. 13, 2017, and a continuation-in-part of application No. 15/674,876, filed on Aug. 11, 2017, and a continuation-in-part of application No. 15/908,365, filed on Feb. 28, 2018, now abandoned.

(51) Int. Cl.
| | | |
|---|---|---|
| A61K 31/353 | (2006.01) | |
| A61K 31/05 | (2006.01) | |
| A61K 31/047 | (2006.01) | |
| A61K 31/7048 | (2006.01) | |
| A61K 47/22 | (2006.01) | |
| A61K 47/12 | (2006.01) | |
| A61K 9/00 | (2006.01) | |
| A61P 19/02 | (2006.01) | |
| A61K 31/12 | (2006.01) | |
| A61K 33/30 | (2006.01) | |
| A61K 33/08 | (2006.01) | |
| A61K 33/10 | (2006.01) | |
| A61K 33/14 | (2006.01) | |
| A61K 33/26 | (2006.01) | |

(52) U.S. Cl.
CPC .......... *A61K 31/353* (2013.01); *A61K 9/0053* (2013.01); *A61K 31/047* (2013.01); *A61K 31/05* (2013.01); *A61K 31/12* (2013.01); *A61K 31/7048* (2013.01); *A61K 47/12* (2013.01); *A61K 47/22* (2013.01); *A61P 19/02* (2018.01); *A61K 33/08* (2013.01); *A61K 33/10* (2013.01); *A61K 33/14* (2013.01); *A61K 33/26* (2013.01); *A61K 33/30* (2013.01); *A61K 2300/00* (2013.01)

(58) Field of Classification Search
CPC .. A61K 2300/00; A61K 31/047; A61K 31/05; A61K 31/12; A61K 31/353; A61K 31/7048; A61K 33/08; A61K 33/10; A61K 33/14; A61K 33/26; A61K 33/30; A61K 47/12; A61K 47/22; A61K 9/0053; A61P 19/02

See application file for complete search history.

(56) References Cited

U.S. PATENT DOCUMENTS

| | | | | |
|---|---|---|---|---|
| 6,589,555 | B2* | 7/2003 | Pandya | A23L 2/40 424/466 |
| 6,812,215 | B2* | 11/2004 | Buchholz | A23L 33/16 514/25 |
| 6,827,945 | B2* | 12/2004 | Rosenbloom | A61K 36/185 424/434 |
| 8,841,264 | B2* | 9/2014 | Raederstorff | A61K 31/05 514/32 |
| 2004/0121024 | A1* | 6/2004 | Gorsek | A61K 31/352 424/643 |
| 2007/0116841 | A1* | 5/2007 | Prakash | A23L 33/105 426/548 |
| 2007/0190209 | A1* | 8/2007 | Sinnott | A61K 36/31 426/72 |
| 2008/0242690 | A1* | 10/2008 | Tripp | A61K 36/00 514/280 |
| 2008/0254185 | A1* | 10/2008 | Yamakawa | A23L 2/60 426/548 |
| 2008/0300198 | A1* | 12/2008 | Matt | G01N 33/6815 514/27 |
| 2009/0130199 | A1* | 5/2009 | Kovacs | A61K 9/006 424/455 |

(Continued)

OTHER PUBLICATIONS

Rylander (J of Pharm and Nutrition Sciences, 2014, 4, 57-59) (Year: 2014).*

(Continued)

*Primary Examiner* — Umamaheswari Ramachandran
(74) *Attorney, Agent, or Firm* — Dinsmore & Shohl LLP

(57) ABSTRACT

The invention encompasses compositions and methods for effectively treating and/or preventing the development and/or progression of osteoarthritis and rheumatoid arthritis and for promoting overall joint health. This is accomplished by totally addressing the key multiple biochemical processes and mechanisms that lead to such disorders. The invention includes compositions comprising a combination of natural agents that safely and effectively suppress, regulate or interfere with the various biochemical processes and mechanisms that increase the risk for or lead to the development and/or progression of OA and RA. The present compositions are holistically formulated to be effective in preventing/arresting loss of and/or damage to the articular cartilage (AC) by suppressing (a) extracellular matrix (ECM) degradation, (b) chondrocyte apoptosis, and (c) inflammation of synovium through modulation of mechanisms that involve transcription factors, growth factors, kinases, antiapoptotic/apoptotic factors and deacetylases. The active agents used herein are natural materials, in particular phytonutrients (or phytochemicals), minerals and/or vitamins.

11 Claims, No Drawings

(56) References Cited

U.S. PATENT DOCUMENTS

| | | | |
|---|---|---|---|
| 2011/0014308 A1* | 1/2011 | Raederstorff | A61K 31/05 |
| | | | 424/769 |
| 2011/0117207 A1* | 5/2011 | Minatelli | A61K 35/57 |
| | | | 424/581 |
| 2011/0245213 A1* | 10/2011 | O'Kennedy | A23L 2/02 |
| | | | 514/171 |
| 2012/0121730 A1* | 5/2012 | Singh | A61K 31/05 |
| | | | 424/682 |
| 2014/0011756 A1* | 1/2014 | Crea | A61K 31/05 |
| | | | 514/27 |
| 2014/0141082 A1* | 5/2014 | Gao | A61K 36/45 |
| | | | 424/474 |
| 2016/0193306 A1* | 7/2016 | Rabovsky | A23L 33/115 |
| | | | 424/93.3 |
| 2018/0008573 A1* | 1/2018 | Brown | A61K 9/2054 |

OTHER PUBLICATIONS

Donsky (https://naturallysavvy.com/restore/is-it-this-simple-could-magnesium-help-your-arthritis/, May 2015 (Year: 2015).*

Zhang et al. (Ann Joint, 2016, p. 1-13) (Year: 2016).*

* cited by examiner

TREATMENT AND PREVENTION OF JOINT DISORDERS

CROSS REFERENCE TO RELATED APPLICATIONS

This application is a continuation-in-part of U.S. application Ser. No. 15/649,084 filed on Jul. 13, 2017, of U.S. application Ser. No. 15/674,876 filed on Aug. 11, 2017 and of U.S. application Ser. No. 15/908,365 filed on Feb. 28, 2018.

FIELD OF THE INVENTION

The present invention relates to compositions and methods for the prevention and/or treatment of joint disorders including osteoarthritis (OA) and rheumatoid arthritis (RA) and for promoting overall joint health. The present compositions comprise combinations of select natural actives that provide additive and/or synergistic benefits against these disorders, associated conditions and contributory factors/inducers including diabetes, obesity, chronic inflammation and oxidative stress. Other inducers of OA and RA include aging, mechanical loading/stress, injury and genetic predisposition. Advantageously, these select actives include materials such as phytonutrients, vitamins and minerals that have been broadly used in food and drink products and are safe for human and pet/animal consumption.

BACKGROUND OF THE INVENTION

According to the World Health Organization (WHO), arthritis comprises many diseases and syndromes, which are usually progressive and associated with pain. These conditions can broadly be categorized as joint diseases and physical disability. Arthritis is caused by multiple triggers mentioned above including trauma/injury and is the leading cause of morbidity and disability, giving rise to enormous healthcare expenditures and loss of work. Among those conditions with the greatest impact on society are osteoarthritis (OA) and rheumatoid arthritis (RA). Both OA and RA are already among the ten most disabling diseases in developed countries. [WHO. "Chronic rheumatic conditions,"]

Osteoarthritis (OA) is a degenerative joint disease, mainly affecting the articular cartilage (AC), whose major components include the extracellular matrix (ECM) and chondrocytes, the only cells found in healthy cartilage. These cells produce and maintain the cartilaginous matrix, which consists mainly of collagen and proteoglycans. OA essentially results from the loss of cartilage resulting from enzymatically-catalyzed degradation of ECM components by proteases and from apoptosis of chondrocytes caused by DNA degrading enzymes. OA is associated with aging and most likely will affect the joints that have been continually stressed throughout the years including the knees, hips, fingers, and lower spine region. Worldwide estimates are that 9.6% of men and 18.0% of women aged over 60 years have symptomatic osteoarthritis. It is estimated that 80% of those with osteoarthritis will have limitations in movement, and 25% cannot perform their major daily activities of life. According to recent estimates, more than 27 million Americans suffer from OA. In 2006, it was estimated that around 35 to 40 million Europeans had OA. It is expected that by 2030, 20% of adults will have developed OA in Western Europe and North America.

Rheumatoid arthritis (RA) is a chronic autoimmune disease that affects the joints, connective tissues, muscle, tendons, and fibrous tissue. Development of both OA and RA results from the degradation of the cartilage. However, in RA inflamed synovial cells are the primary source of the degrading enzymes. RA tends to strike during the most productive years of adulthood, between the ages of 20 and 40, and is a chronic disabling condition often causing pain and deformity. The global prevalence of RA is estimated at around 0.24% and is more common in women and in developed countries. In these estimates, DALYs (disability-adjusted life years) increased from 3.3 million in 1990 to 4.8 M in 2010. This increase was due to a growth in population and increase in aging. RA continues to cause modest global disability, but with severe consequences in the affected individuals. Within 10 years of onset, at least 50% of patients in developed countries are unable to hold down a full-time job. In the US in 2014, estimates for the overall age-adjusted prevalence of RA ranged from 0.53 to 0.55% (0.29-0.31% for males and 0.73-0.78% for females). The prevalence of RA in the US appeared to increase during the period from 2004 to 2014, affecting a conservative estimate of 1.28-1.36 million adults in 2014. [See e.g., Hunter T M et al. (2017), "Prevalence of rheumatoid arthritis in the United States adult population in healthcare claims databases, 2004-2014," *Rheumatol Int.* 37(9):1551-1557.]

Therefore, there is a continuing and critical need for therapeutic and preventive compositions and methods against osteoarthritis and rheumatoid arthritis as well as for promoting overall bone and joint health. The global incidence of these age-related diseases of bone, joint, and muscle is steadily rising and seriously affecting the health of millions of people worldwide. Musculoskeletal, rheumatic, and arthritic conditions are leading causes of morbidity and disability throughout the world, and result in enormous healthcare expenditure and loss of work. Osteoarthritis (OA), also known as osteoarthrosis or degenerative joint disease (DJD), is the most common form of arthritis and the most common type of degenerative joint disease. It is the major cause of pain and disability affecting particularly the elderly. According to a United Nations report, by 2050 130 million people will suffer from OA worldwide, of whom 40 million will be severely disabled by the disease. [See e.g., Woolf A D and Pfleger B (2003), "Burden of major musculoskeletal conditions". *Bull World Health Organ.* 81(9): 646-56; Ehrlich G E (2003), "The rise of osteoarthritis". *Bull World Health Organ.* 81(9):630; National Institute of Arthritis and Musculoskeletal and Skin Diseases (NIAMS). (2012); Symmons D, et al. (2000), "Global burden of osteoarthritis in the year 2000". WHO; Centers for Disease Control and Prevention (CDC), (2012); United Nations. "World Population to 2300".]

SUMMARY OF THE INVENTION

The invention encompasses compositions and methods for effectively treating and/or preventing the development and/or progression of osteoarthritis and rheumatoid arthritis and for promoting overall joint health. This is accomplished by totally addressing the multiple biochemical processes and mechanisms that lead to such disorders. The invention includes compositions comprising a combination of agents that effectively suppress, regulate or interfere with the various biochemical processes and mechanisms that increase the risk for or lead to the development and/or progression of OA and RA. The present compositions are holistically formulated to be effective in preventing/arresting loss of and/or damage to the articular cartilage (AC) by suppressing (a) extracellular matrix (ECM) degradation, (b)

chondrocyte apoptosis, and (c) inflammation of synovium. The inventive compositions used for administration to human and other mammalian subjects having or at risk for development and/or progression of osteoarthritis (OA) and/or rheumatoid arthritis (RA) comprise (1) at least one agent that inhibits and/or suppresses expression and/or activity of one or more of inflammatory mediators including interleukins IL-1α, IL-1β, IL-6, NF-κB, TNF-α, matrix metalloproteinases (MMPs), prostaglandin E2 (PGE2), and nitric oxide (NO); (2) at least one agent that inhibits the activity of pro-oxidants including reactive nitrogen species (RNS) and reactive oxygen species (ROS) and/or upregulates expression and/or activity of antioxidants including glutathione (GS), superoxide dismutase (SOD) and catalase; (3) at least one agent that induces the expression of and/or activates one or more of AMPK (adenosine monophosphate-activated protein kinase, SIRT1 (sirtuin1), HIF-1α (hypoxia inducible factor 1 alpha), SOX9 (SRY-related protein 9), BMP-7 (bone morphogenetic protein 7), and ERK 1/2 (extracellular regulated kinase isoforms 1 and 2); (4) at least one agent capable of modulating expression and/or activity of one or more of Runx2 (Runt-related transcription factor 2 also known as core-binding factor subunit alpha-1), P38-MAPK (mitogen-activated protein kinase), HIF-2α (hypoxia inducible factor 2 alpha), and AP-1 (Activator protein 1); (5) at least one agent capable of modulating expression and/or activity of one or more of VEGF (vascular endothelial growth factor) and FGF (fibroblast growth factor); (6) at least one agent capable of modulating expression and/or activity of one or more of NMDAR (N-methyl-D-aspartic acid receptor), mTOR (mammalian target for rapamycin) and Wnt/β-catenin signaling pathway; and (7) at least one agent capable of inducing expression of and/or activating antiapoptotic proteins (including Bcl-2 and beclin) and/or suppressing proapoptotic proteins (including, (Bcl-2-associated X protein, Bax).

The active agents for use herein are natural materials, in particular phytonutrients (or phytochemicals), minerals and/or vitamins. It is to be understood that any one of the agents used herein may provide multiple activities or functions; thus in some embodiments the present combinations may comprise less than seven (7) different agents to provide the target activities. Compositions with combinations of such natural agents are safe and efficacious to prevent, reduce or treat OA, RA and associated disorders or triggers including diabetes, obesity, oxidative stress and systemic inflammation. The mechanisms and processes that lead to the development and/or progression of osteoarthritis and rheumatoid arthritis are discussed in detail below.

DETAILED DESCRIPTION OF THE INVENTION

All percentages used herein are by weight of the composition, unless otherwise specified. The ratios used herein are molar ratios of the overall composition, unless otherwise specified.

All measurements of e.g., weights, pH values, etc. are made at 25° C. with standard equipment, unless otherwise specified.

As used in this disclosure and the appended claims, the singular forms "a," "an" and "the" include plural referents unless the context clearly dictates otherwise. As used herein, "about" is understood to refer to numbers in a range of numerals. Moreover, all numerical ranges herein should be understood to include all integers, whole or fractions, within the range. The compositions disclosed herein may lack any element that is not specifically disclosed herein. Herein, "comprising" and its variants mean that other steps and other ingredients which do not affect the end result can be added. The terms encompass the terms "consisting of" and "consisting essentially of". Thus, the disclosure of an embodiment using the term "comprising" includes a disclosure of an embodiment "consisting essentially" of and an embodiment "consisting" of the referenced components. Any embodiment disclosed herein can be combined with any other embodiment disclosed herein.

As used herein, the word "include," and variants, are intended to be non-limiting, such that recitation of items in a list is not to the exclusion of other like items that may also be useful in the materials, compositions, devices, and methods of this invention.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the terms "prevent", "prevention" and variants includes reduction of risk and/or severity of osteoporosis, osteoarthritis, rheumatoid arthritis, vascular calcification, diabetes, obesity and/or any other referenced condition. The terms "treatment", "treat", "ameliorate" and "alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measures. The terms "treatment," "treat" and "alleviate" are further intended to include the dietary management of a disease or condition or the dietary management for prophylaxis or prevention a disease or condition. A treatment can be patient- or doctor-related.

As used herein, a "therapeutically effective amount" is an amount that prevents a deficiency, treats a disease or medical condition in an individual or, more generally, reduces symptoms, manages progression of the diseases or provides a nutritional, physiological, or medical benefit to the individual. The therapeutically effective amount that is required to achieve a therapeutic effect will, of course, vary with the particular composition, the route of administration, the age and the condition of the recipient, and the particular disorder or disease being treated or prevented.

By "safe and effective amount" as used herein means a sufficient amount of an active agent to provide the desired benefit while being safe and will vary with the particular condition being treated, the age and physical condition of the patient being treated, the severity of the condition, the duration of treatment, the nature of concurrent therapy, the specific form of the agent(s) employed, and the particular vehicle from which the agent(s) are applied.

As used herein, "animal" includes, but is not limited to, mammals, which includes but is not limited to, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human, having or at risk for a medical condition that can benefit from the treatment.

The terms "phytonutrients" or "phytochemicals" are used interchangeably herein to denote natural chemical compounds that are found in many plant foods and refers to any compound produced by a plant that imparts one or more health benefits to the user. "Phyto" refers to the Greek word for plant. These chemicals help protect plants from germs, fungi, bugs, and other threats.

The terms, "food product", "food composition", "nutritional composition", "dietary supplement" and variants as used herein, are understood to mean ingestible compositions comprising nutrients and may include any number of optional additional ingredients, including conventional additives, for example, one or more proteins, carbohydrates, fats, vitamins, minerals, acidulants, thickeners, buffers or agents for pH adjustment, chelating agents, colorants, emulsifiers, excipients, flavoring and sweetening agents, osmotic agents, preservatives, stabilizers, sugars, sweeteners, and/or texturizers, acceptable excipients and/or carriers for oral consumption. The optional ingredients can be added in any suitable amount.

The term "carriers" refer to one or more compatible solid or liquid excipients or diluents which are suitable for oral administration and consumption. By "compatible," as used herein, is meant that the components of the composition are capable of being commingled without interaction in a manner which would substantially reduce the composition's stability and/or efficacy. Suitable excipient and/or carriers for ingestible products include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, vegetable gums, lactose, methyl cellulose, povidone, carboxymethyl cellulose, corn starch, and the like (including mixtures thereof). Preferred carriers include calcium carbonate, magnesium stearate, maltodextrin, and mixtures thereof.

Suitable flavoring agents include oil of wintergreen, oil of peppermint, oil of spearmint, clove bud oil, menthol, anethole, methyl salicylate, eucalyptol, *cassia,* 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof.

Sweetening agents which can be used include sucrose, glucose, saccharin, dextrose, levulose, lactose, mannitol, sorbitol, fructose, maltose, xylitol, saccharin salts, thaumatin, stevioside, aspartame, D-tryptophan, dihydrochalcones, acesulfame and cyclamate salts, especially sodium cyclamate and sodium saccharin, and mixtures thereof.

The compositions of the present invention may be in various forms including ingestible solid forms such as capsules, tablets, pills, gummies, gelcaps, or granules and powder such as teas and drink mixes. The compositions may also be prepared as a liquid solution, emulsion, concentrate, gel, and the like for beverage and like products.

The present compositions may also be prepared for use in topical applications such as for the oral cavity, skin, hair, scalp and nails. By "topical composition", "oral, hair, skin, scalp or nail care composition" as used herein means products which in the ordinary course of usage are not intentionally swallowed for purposes of systemic administration of particular therapeutic agents, but are rather retained in the oral cavity or other body surfaces/tissues for a time sufficient to contact substantially all such dental, mouth, skin, scalp, hair or nail surfaces and/or tissues to deliver the intended benefits.

The topical oral care composition of the present invention may be in various forms including toothpaste, dentifrice, tooth powder, topical oral gel, mouthrinse, denture product, mouthspray, mousse, foam, lozenge, oral tablet, and chewing gum. Examples of composition forms for the care of the skin, scalp, hair or nail include lotions, creams, gels, cleansers, scrubs, shampoos, rinses, rinse-off or leave-in conditioners, mousses, hairsprays, ointments, tinctures and salves. Carriers and excipients for these topical products are well known in the art. For example, conventional additives in oral care compositions include but are not limited to fluoride ion sources; anti-calculus or anti-tartar agents; antimicrobial agents such as stannous salts, cetyl pyridinium chloride (CPC), flavor oils and others; buffers; abrasives such as silica; bleaching agents such as peroxide sources; alkali metal bicarbonate salts; thickening materials; humectants; water; surfactants; titanium dioxide; flavor system; sweetening agents; xylitol; coloring agents, and mixtures thereof.

For pet and animal care, the present compositions may be formulated for example as tablets, foods, chews and toys. The active agent(s) may be incorporated for example, into a relatively supple but strong and durable material such as rawhide, ropes made from natural or synthetic fibers, and polymeric articles made from nylon, polyester or thermoplastic polyurethane. As the animal chews, licks or gnaws the product, incorporated active agents are released into the animal's oral cavity and ingested. In pet food embodiments, the active agent(s) may be incorporated as an ingredient or admixed into a pet food such as for example, a kibbled, semi-moist, or canned food. The present compositions may also be incorporated into other pet care products including nutritional supplements and drinking water additives.

The various ingredients and the excipient and/or carrier are mixed and formed into the desired form using conventional techniques. For example, the tablet or capsule of the present invention may be coated with an enteric coating that dissolves at a pH of about 5.0 to 9.0. Suitable enteric coatings that dissolve at a higher pH in intestine but not in the stomach include cellulose acetate phthalate, phospholipid bilayers and others. Further materials are well known in the art and are readily chosen by one skilled in the art based on the physical, aesthetic and performance properties desired for the compositions being prepared. Details on techniques for formulation and administration may be found in *Remingtons' Pharmaceutical Sciences* (18th Edition, 1990); *Cosmetic and Toiletry Formulations* ($2^{nd}$ Edition, 1989); *The International Cosmetic Ingredient Directory and Handbook* ($8^{th}$ Edition, 2000).

Active and other ingredients useful herein may be categorized or described herein by their therapeutic and/or nutritional benefit or their postulated mode of action or function. However, it is to be understood that the active and other ingredients useful herein can, in some instances, provide more than one therapeutic benefit or function or operate via more than one mode of action. Therefore, classifications herein are made for the sake of convenience and are not intended to limit an ingredient to the particularly stated application or applications listed.

Arthritis is a degenerative disease of the joints. It includes osteoarthritis (OA) and rheumatoid arthritis (RA). As with osteoporosis, OA and RA have in common an upsurge of inflammation and oxidative stress, resulting in progressive histological alterations and disabling symptoms.

Osteoarthritis (OA) is characterized by destruction of articular cartilage and bone erosion, induced by multiple effectors, including pro-inflammatory cytokines, e.g., interleukin 1 (IL-1), interleukin 6 (IL-6), and tumor necrosis factor α (TNF-α), fragmented and un-fragmented matrix proteins, chondrocytes hypertrophy, mitochondrial dysfunction, nitic oxide, and oxidative stress. These mediators increase synthesis of collagenase or matrix metalloproteinase (MMP) and the degradation of collagen type II, and decrease the synthesis of collagenase inhibitors: collagen and proteoglycans by modulating various mechanisms. Degradation of collagen type II by collagenase-1 and collagenase-3 (also called MMP-13), and aggrecanases (the predominant one being ADAMTS-5, a disintegrin-like and metalloproteinase with thrombospondin 5) represents one of the biochemical hallmarks of osteoarthritis. Factors that increase the risk of OA include advanced age, sex, obesity, increased body mass index (BMI), genetics, ethnicity, diet, trauma, and certain physical or occupational activities that induce biomechanical stress (e.g., pressure, load-bearing) across the joints. [See e.g., Dragos D, et al. (2017), "Phytomedicine in Joint Disorders". *Nutrients.* 9(1):70; Mobasheri A (2012), "Intersection of Inflammation and Herbal Medicine in the Treatment of Osteoarthritis". *Curr. Rheumatol. Rep.* 14(6):604-616; Green J A, et al. (2014), "The potential for dietary factors to prevent or treat osteoarthritis". *Proceedings of the Nutrition Society,* 73(2): 278-288.]

Rheumatoid arthritis (RA) is a chronic progressive systemic autoimmune disease generating disability and increased risk for cardiovascular disease, lymphoma, and death. It mostly affects smaller joints such as those of the fingers, toes, wrists and ankles. RA is characterized by synovial inflammation, hyperplasia, autoantibody production, i.e., rheumatoid factor (RF) and anti-citrullinated protein antibody (ACPA) and cartilage destruction. The precise causes of RA remain uncertain. However, both environmental factors and genetic predisposition are believed to contribute to RA development. These environmental factors include smoking, exposure to infectious agents (virus and bacteria), periodontal disease, and gastrointestinal microbiome. It is estimated that 50% of risk for developing RA is attributed to genetic predisposition, and the rest is attributed to environmental factors. These environmental factors and early life events such as infections have long lasting effects on the body's overall immune function. There is evidence that production of the RA associated autoantibodies, including rheumatoid factor (RF) and anti-citrullinated protein antibody (ACCP), and increased levels of C-reactive protein (CRP) occur years before the appearance of RA clinical symptoms.

Multiple cell types, including lymphocytes, dendritic cells, microphages and synovial cells (synovial fibroblasts, endothelial and perivascular cells) contribute to the etiology of RA via attacking the synovial membrane and/or the synovium that surrounds the joint. These cells produce pro-inflammatory cytokines (IL-1β, IL-6 and TNF-α); transcription factors such as NF-κB; growth factors; cyclooxygenase (COX2) and lipoxygenase, which are involved in intracellular pathways inducing production of proteases. These proteases mediate the degradation of cartilage. Among these cells RA synovial fibroblasts (RASFs) are thought to be the key contributor to the development of RA mediated articular cartilage destruction. In healthy subjects, proliferation and apoptosis is tightly regulated. However, in the RA state, RASFs become apoptosis resistant. This is evidenced by the increased level of the antiapoptotic protein, Bcl-2, observed in RA patients.

[See e.g., de Brito Oliveira A L, et al. (2017), "Resveratrol Role in Autoimmune Disease-A Mini-Review". *Nutrients,* 9:1306, doi:10.3390/nu9121306; Klareskog L, et al. (2006), "Mechanisms of Disease: genetic susceptibility and environmental triggers in the development of rheumatoid arthritis". *Nat. Clin. Pract. Rheumatol.* 2(8):425-33; Ansari M and Khan H A (2014), "Quercetin alleviate oxidative stress and inflammation through up-regulation of antioxidant machinery and down-regulation of COX2 and NF-κB expression in Collagen induced rheumatoid arthritis". *Int. J. Drug Dev. & Res.,* 6: 15-230; Hao L, et al. (2017, "A study of Sirt1 regulation and the effect of resveratrol on synoviocyte invasion and associated joint destruction in rheumatoid arthritis". *Molecular Medicine Reports,* 16:5099-5106; Müller-Ladner U, et al. (2008), "Mechanisms of disease: The molecular and cellular basis of joint destruction in rheumatoid arthritis". *Nature Clinical Practice Rheumatology,* 1(2): 102-10; Liu-Bryan R (2015), "Inflammation and intracellular metabolism: new targets in OA. *Osteoarthritis and Cartilage* 23:835e1842; McInnes I B and Schett G (2011), "The Pathogenesis of Rheumatoid Arthritis". *N. Engl. J. Med.* 365:2205-19; Edwards C J and Cooper C (2006), "Early environmental factors and rheumatoid arthritis". *Clin Exp Immunol.* 143(1): 1-5 doi:10.1111/j.1365-2249.2005.02940.x; Byun H S, et al. (2008), "Caspase-8 has an essential role in resveratrol-induced apoptosis of rheumatoid fibroblast-like synoviocytes". Rheumatology (Oxford) 47: 301-308; Sing A K, et al. (2016), "Regulation of TAK1 activation by epigallocatechin-3-gallate in RA synovial fibroblasts: suppression of K63-linked autoubiquitination of TRAF6". *Arthritis Rheumatol.* 68(2):347-358. doi: 10.1002/art.39447; Bhupinder K, et al. (2017), "Natural products in treatment of rheumatoid arthritis". *International Journal of Green Pharmacy* (Suppl) 11(3):5356; González R, et al. (2011), "Effects of Flavonoids and other Polyphenols on Inflammation". *Critical Reviews in Food Science and Nutrition,* 51:331-362; Khanna D, et al. (2007), "Natural products as a gold mine for arthritis treatment". *Current Opinion in Pharmacology,* 7:344-351.]

In contrast to RA, OA is primarily an outcome of wear-and-tear damage, predominantly as a function of mechanical stress and aging, affecting the joints of the hips, spine, knees, and hands. Between these two types of arthritis, OA is by far the more prevalent and devastating disease of the joint. Globally, millions of people suffer from this degenerative disease. In the United States, the prevalence of OA has steadily increased to more than 27 million people currently, likely due to aging of the population and the rising prevalence of obesity. In fact, OA is recognized as one of the leading causes of disability among the adult population with symptoms including pain, stiffness, swelling, loss of mobility, and reduction of quality of life. [See e.g., Lawrence R C, et al. (2008), "Estimates of the prevalence of arthritis and other rheumatic conditions in the United States. Part II".

Arthritis Rheum. 58:26-35; Plotnikoff R, et al. (2015), "Osteoarthritis prevalence and modifiable factors: a population study," BMC Public Health 15:1195; Grover A K and Samson S E (2016), "Benefits of antioxidant supplements for knee osteoarthritis: rationale and reality". *Nutrition Journal*, 15:1; Gupta P K, et al. (2012). "Mesenchymal stem cells for cartilage repair in Osteoarthritis". *Stem Cell Research & Therapy*, 3:25; Akkiraju H and Nohe A (2015). "Role of Chondrocytes in Cartilage Formation. Progression of Osteoarthritis and Cartilage Regeneration". *Dev. Biol.* 3(4): 177-192; Goldring M B and Marcu K B (2009), "Cartilage homeostasis in health and rheumatic diseases." *Arthritis Research & Therapy*, 11:224; van der Kraan P M and van den Berg W B (2012), "Chondrocyte hypertrophy and osteoarthritis: role in initiation and progression of cartilage degeneration?". *Osteoarthritis and Cartilage* 20:223e232; Zhong L, et al. (2015), "The Regulatory Role of Signaling Crosstalk in Hypertrophy of MSCs and Human Articular Chondrocytes". *Int. J. Mol. Sci.* 16:19225-19247; Charlier E, et al. (2016), "Insights on Molecular Mechanisms of Chondrocytes Death in Osteoarthritis". *Int. J. Mol. Sci.* 17:2146; Ansari M and Khan H A (2014), Ibid.; Liu-Bryan R (2015), Ibid.; Hao L, et al. (2017), Ibid.]

Joints are areas, where bones come together to provide flexibility and movement to the skeleton. The joint bones are separated from each other by a tissue called articular cartilage (AC). AC is a highly specialized tissue whose primary function is to provide support and flexibility and reduce friction to the joint. AC is avascular (i.e., characterized by or associated with a lack of blood vessels) and hypoxic (i.e., having inadequate oxygenation). As such, AC does not have the ability to regenerate itself. The major components of AC include the extracellular matrix (ECM) and chondrocytes.

ECM is the material covering the ends of bones at the joints. It is primarily composed of water, collagen, proteoglycans and other minor proteins. Type II collagen, is the most abundant structural component of ECM. It provides tensile strength to the cartilage, a framework for the other ECM components, particularly to the proteoglycans, and adhesion to chondrocytes' cytoskeleton. Proteoglycans are primarily composed of aggrecan, also known as cartilage-specific proteoglycan core protein (CSPCP) or chondroitin sulfate proteoglycan 1. Along with type-II collagen, aggrecan forms the major structural component of cartilage, particularly of articular cartilage. They provide gelling/cushioning property to the joint, and protection to the collagen network from degradation. Degradation of collagen and aggrecans resulting from proteolysis is associated with the development of arthritis. Proteases capable of degrading aggrecans are called aggrecanases, and they are members of the ADAM (A Disintegrin And Metalloproteinase) protein family. Proteases known as matrix metalloproteases (MMPs, primary one is MMP-13) degrade collagen. [See e.g., Fox A J, et al. (2009), "The Basic Science of Articular Cartilage: Structure, Composition, and Function". *Sports Health*, 1:461-468; Goldring M B and Marcu K B (2009), .Ibid.]

Chondrocytes are the only cells found in cartilage; they are embedded in the ECM. Their main function is to maintain the structure and function of AC under normal and low turnover conditions by producing collagen, proteoglycans, minor proteins, and enzymes. Since AC is avascular and hypoxic tissue without mesenchymal stem cells (MSCs), chondrocytes are incapable of regenerating themselves. In healthy individuals, chondrocytes remain in a post-mitotic state throughout life. However, when disturbed by risk factors (e.g., aging, mechanical loading, genetic predisposition) and/or in a joint disease state, chondrocytes undergo changes, including senescence, increase in proteolytic enzymes and inflammatory cytokines, and cell death. Like osteoblasts and adipocytes, chondrocytes originate from mesenchymal stem cells (MSCs) that reside in the bone marrow. The differentiation of chondrocytes involves various transcription factors (Sox9 and Runx2), growth factors (TGF-β), and signaling pathway (Wnt/β-catenin). However, once they become ECM producing cells and embedded in cartilage, they either remain as permanent chondrocytes throughout life or become hypertrophic and eventually die. Thus, unless disturbed, chondrocytes remain in a post-mitotic state throughout life. Since dead and/or dysfunctional chondrocytes are not replaced with new ones, the survival of chondrocytes is critically important for the maintenance of healthy articular cartilage and the prevention of OA. [See e.g., Leong D J, et al. (2013), "Nutraceuticals: Potential for Chondroprotection and Molecular Targeting of Osteoarthritis". *Int. J. Mol. Sci.* 14:23063-23085; Akkiraju H and Nohe A (2015), "Role of Chondrocytes in Cartilage Formation, Progression of Osteoarthritis and Cartilage Regeneration". *Dev. Biol.* 3(4): 177-192; Heino T J and Hentunen, T A (2008), "Differentiation of Osteoblasts and Osteocytes from Mesenchymal Stem Cells". *Current Stem Cell Research & Therapy*, 3:131-145; Csaki C, et al. (2009), "Synergistic chondroprotective effects of curcumin and resveratrol in human articular chondrocytes: inhibition of IL-1β-induced NF-κB-mediated inflammation and apoptosis". *Arthritis Research & Therapy*, 11:R165; Akiyama H, et al. (2002), "The transcription factor Sox9 has essential roles in successive steps of the chondrocyte differentiation pathway and is required for expression of Sox5 and Sox6". *Genes & Development*, 16:2813-2828; Li T F, et al. (2005), "TGF-β Signaling in Chondrocytes". *Front. Biosci.* 1:681-688; Grassel S, and Ahmed N (2007), "Influence of cellular microenvironment and paracrine signals on chondrogenic differentiation". *Frontiers in "Bioscience*, 12:4946-4956; Peng X, et al. (2014), "Wnt/β-Catenin Signaling Regulates the Proliferation and Differentiation of Mesenchymal Progenitor Cells through the p53 Pathway". *PLOS ONE* 9(5): e97283; Day T F, et al. (2005), "Wnt/–Catenin Signaling in Mesenchymal Progenitors Controls Osteoblast and Chondrocyte Differentiation during Vertebrate Skeletogenesi". *Developmental Cell*, 8:739-750; Lotz M, et al. (1999), "Mechanisms of chondrocyte apoptosis". *Osteoarthritis and Cartilage*, 7:389-391; Oh C D and Chun J S. (2003), "Signaling Mechanisms Leading to the Regulation of Differentiation and Apoptosis of Articular Chondrocytes by Insulin-like Growth Factor-1". *J. Biol. Chem.* 278(38): 36563-36571; Fox A J, et al. (2009), "The Basic Science of Articular Cartilage: Structure, Composition, and Function". *Sports Health*, 1:461-468; Goldring M B and Marcu K B (2009), .Ibid.; Charlier E, et al. (2016), "Insights on Molecular Mechanisms of Chondrocytes Death in Osteoarthritis". *Int. J. Mol. Sci.* 17:2146; Lotz M and Carames B (2011), "Autophagy and Cartilage Homeostasis Mechanisms in Joint Health, Aging and Osteoarthritis". *Nat. Rev. Rheumatol.* 7(10): 579-587.

In both OA and RA, the endpoint is degradation/loss of the cartilage; however, the respective triggers, mode of action, and mechanisms in their development and progression are different. The loss of cartilage is caused by enzymatically catalyzed degradation of matrix components (collagen and proteoglycans) by proteases, including collagenases, known as matrix metalloproteases (MMPs, primary one is MMP-13) and aggrecanases (ADAMTS5). In OA, chondrocytes are the main producers of the ECM degrading proteases; whereas, inflamed synovial cells are the primary source of the proteases that mediate RA development and progression.

Development and progression of OA are an outcome of: (1) loss of cartilage caused by enzymatically catalyzed degradation of matrix components (collagen and proteoglycans) by proteases, including collagenases and aggrecanases and (2) chondrocyte apoptosis, caused by DNA degrading enzymes, the caspases, of which caspase-3 is the active form.

In OA, homeostasis of AC is disrupted due to an increase in catabolism because of ECM degradation mediated by proteases and to a decrease in anabolism because of chondrocyte apoptosis. Such destruction of the matrix components causes loss of cartilage elasticity and tensile strength to the joint as well as impairment of chondrocytes ability to replace the loss of matrix proteins caused by the increase in catabolism mediated by apoptosis of chondrocytes and their inability to regenerate.

OA is triggered by multiple risk factors, including aging, mechanical stress, genetic predisposition, obesity, diabetes, chronic inflammation, oxidative stress. Of these risk factors, the primary ones are aging and biomechanical stress.

Aging triggers the development and progression of OA by (a) promoting apoptosis, which results in reduction of the population of chondrocytes; (b) impairing the response of chondrocytes to growth factors; (c) stimulating chondrocytes to produce catabolic factors, including pro-inflammatory cytokines (TNF-α, IL-6 and IL-1β) and matrix degrading enzymes (collagenases and aggrecanases); (d) promoting production and accumulation of advanced glycation end products (AGEs); (e) enhancing chondrocyte hypertrophy and ossification, (f) mediating mitochondrial dysfunction; (g) decreasing expression and/or activation of adenine monophosphate activated protein kinase (AMPK) and Sirtuin 1 (SIRT1); and (h) impairing autophagy, the natural, regulated, destructive mechanism of the cell that disassembles unnecessary or dysfunctional components. [See e.g., van der Kraan P M and van den Berg W B (2012), "Chondrocyte hypertrophy and osteoarthritis: role in initiation and progression of cartilage degeneration?". *Osteoarthritis and Cartilage* 20: 223e232; Li Y P, et al. (2013), "The Age-Related Changes in Cartilage and Osteoarthritis". *BioMed. Research International,* 916530; Taniguchia N, et al. (2009), "Chromatin protein HMGB2 regulates articular cartilage surface maintenance via catenin pathway". *PNAS,* 106:16817-16822; Liu-Bryan R (2015), Ibid.; Lotz M and Carames B (2011), "Autophagy and Cartilage Homeostasis Mechanisms in Joint Health, Aging and Osteoarthritis". *Nat. Rev. Rheumatol.* 7(10): 579-587; DeGroot J, et al. (2004), "Accumulation of Advanced Glycation End Products as a Molecular Mechanism for Aging as a Risk Factor in Osteoarthritis". *Arthritis Rheum.,* 50: 1207-1215; Yamabe S, et al. (2013), "Intracellular accumulation of advanced glycation end products induces apoptosis via endoplasmic reticulum stress in chondrocytes". *FEBS Journal,* 280:1617-1629; Wang Y, et al. (2015), "Mitochondrial Biogenesis Is Impaired in Osteoarthritis Chondrocytes but Reversible via Peroxisome Proliferator-Activated Receptor g Coactivator 1a". *Arthritis Rheumatol.,* 67: 2141-2153.]

AMPK deficiency has been shown to promote aging, ECM degradation and OA development by enhancing proteases, inflammatory cytokines production, and chondrocyte apoptosis. By contrast, induction and/or activation of AMPK and SIRT1 have been demonstrated to reverse mitochondrial dysfunction mediated by aging and OA and to enhance chondrocytes survival by inducing autophagy. Both AMPK and SIRT1 (Sirtuin 1) are considered master metabolic regulators due to their ability to modify and control numerous transcription factors and co-factors involved in systemic metabolic homeostasis as discussed in parent applications U.S. Ser. No. 15/674,876 and U.S. Ser. No. 15/908,365. SIRT1 also functions as a key transcriptional regulator of inflammation. Macrophage activation and infiltration into resident tissues mediate local inflammation. This local inflammation has been increasingly recognized as a causal factor leading to the development of a cluster of diseases including arthritis, osteoporosis as well as type 2 diabetes mellitus (T2DM) and obesity. Several recent studies indicate that the beneficial effect of SIRT1 on metabolic disorders is due in part to its ability to suppress the activity of NF-κB, the master regulator of cellular inflammatory response in macrophages. [See e.g., Zhou S, et al. (2017), "AMPK deficiency in chondrocytes accelerated the progression of instability-induced and ageing associated osteoarthritis in adult mice". *Scientific Reports,* 7:43245; Liu-Bryan, R (2015), Ibid; Wang Y, et al. (2015), Ibid.]

Mechanical loading, stress and/or injury of AC cause the degradation of key matrix components, collagen and proteoglycans, and apoptosis of chondrocytes, both leading to OA development and progression. Even though mechanical loading within a physiological range is essential for maintaining healthy AC, it has also been shown to lead to OA. Excess loading stress can cause degradation of ECM network and release of degradation fragments and collagen. These are sensed by chondrocytes through mechanoreceptors and molecular cell surface receptors called the integrins, which lead to degradation of AC mediated by induction of ECM degrading enzymes (including MMP-13 and ADAMTS5), pro-inflammatory cytokines (TNF-α, IL-6 and IL-1β), and reactive oxygen species (ROS). These interactions between integrins and ECM components have been implicated in dysfunction of chondrocytes, apoptosis and degradation of ECM. Furthermore, mechanical stress promotes chondrocyte hypertrophic differentiation, which causes stimulation of MMPs, expression of inflammatory cytokines and subsequent induction of cartilage degradation and chondrocyte apoptosis, primarily mediated by Runx2. [See e.g., Kauguchi H (2016), "Mechanisms of Osteoarthritis from Animal Models". *J. Osteo. Arth.* 1: 1-5; Lee H S and Salter D M (2015), "Biomechanics of Cartilage and Osteoarthritis". *Osteoarthritis—Progress in Basic Research and Treatment,* Chapter 3; Krammer W C, et al. (2011), "Pathogenetic mechanisms of posttraumatic osteoarthritis: opportunities for early intervention". *Int. J. Clin. Exp. Med.* 4:285-298.]

The various OA triggers (aging, mechanical loading/stress/injuries, obesity, diabetes, chronic inflammation, oxidative stress, sedentary lifestyle, and genetic pre-disposition) separately or in combination, cause the development and progression of OA by modulating production and/or activation of the following OA promoters. [See e.g., Leong D J, et al. (2013), "Nutraceuticals: Potential for Chondroprotection and Molecular Targeting of Osteoarthritis". *Int. J. Mol. Sci.* 14:23063-23085; Goldring M B and Goldring S R (2007), "Osteoarthritis". *J. Cell. Physiol.* 213:626-634; Pelletier J P, et al. (2001), "Osteoarthritis, an Inflammatory Disease Potential Implication for the Selection of New Therapeutic Targets". *Arthritis Rheum.* 44:1237-1247; Charlier E, et al. (2016), "Insights on Molecular Mechanisms of Chondrocytes Death in Osteoarthritis". *Int. J. Mol. Sci.* 17:2146; Abramson S B and Attur M (2009), "Developments in the scientific understanding of osteoarthritis". *Arthritis Research & Therapy,* 11:227; Grogan S P and D'Lima D D (2009), "Joint aging and chondrocyte cell death". *Int. J. Clin. Rheumtol.* 5(2):199-214.]

(1) Release of fragmented and un-fragmented matrix proteins: Matrix proteins, particularly collagen type 2 can initiate OA by binding to a receptor called tyrosine kinase discoidin domain receptor 2 (DDR-2). This causes degradation of matrix proteins, including collagen type 2 and aggrecan. Subsequently, these degradation products cause an initiation of OA mediated by induction of proteases expression through binding to a chondrocyte transmembrane receptor called integrins. Collagen type II plays important role in the survival of chondrocytes through providing adhesion. As a result, degradation of collagen has been demonstrated to cause chondrocyte apoptosis, increased degradation of ECM, and chondrocyte hypertrophy. [See e.g., Kauguchi H (2016), Ibid.; Facchini A, et al. (2014), "Hydroxytyrosol Prevents Increase of Osteoarthritis Markers in Human Chondrocytes Treated with Hydrogen Peroxide or Growth-Related Oncogene a". *PLOS ONE*, 9(10): e109724; Lee H S and Salter D M (2015), Ibid.; Hwang H S and Kim H A (2015), "Chondrocyte Apoptosis in the Pathogenesis of Osteoarthritis". *Int. J. Mol. Sci.* 16: 26035-26054.]

(2) Accumulation of advanced glycation end products (AGEs): During aging, accumulation of AGEs due to non-enzymatic glycation occurs in AC. Such an increase in AGEs promotes the development and progression of OA through multiple mechanisms, including (a) stimulation of collagen and proteoglycans degradation, (b) suppression of collagen and proteoglycan synthesis, (c) inducing production of pro-inflammatory cytokines (IL-1β and TNF-α), proteinases (MMPs and aggrecanases), nitric oxide (NO) and prostaglandin E2 (PGE2), production of reactive oxygen species (ROS) and (d) causing chondrocytes apoptosis. These undesirable effects on cartilage are in part mediated through activation of necrosis factor-κB (NF-κB) and activator protein 1 (AP-1) by AGEs. [See e.g., Liu F C, et al. (2010). Chondroprotective effects and mechanisms of resveratrol in advanced glycation end products stimulated chondrocytes. *Arthritis Research & Therapy*, 12:R167; Li Y P, et al. (2013), "The Age-Related Changes in Cartilage and Osteoarthritis". *BioMed Research International*.]

(3) Impaired autophagy: AC does not have phagocytes to remove dead and/or damaged organelles or macromolecules. As a result, dead cells and organelles accumulate in the ECM, and subsequently cause matrix degradation and chondrocyte apoptosis. To prevent these processes, AC utilizes an autophagy (lysosomal degradation) to remove dead cells, dysfunctional organelles, and damaged macromolecules. Autophagy is a lysosomal degradation pathway that is essential for survival of chondrocytes and AC homeostasis. Impairment of autophagy causes accumulation of dead cells macromolecules in the cartilage matrix, mitochondrial dysfunction, production of reactive oxygen species (ROS), abnormal gene expression and cell death, all of which subsequently and negatively affect matrix structure and function of chondrocytes. Hence, a functioning autophagy plays an important role in ECM synthesis, chondrocyte viability, and energy production. Autophagy is regulated by (1) promoters including antiapoptotic proteins (beclin-1 and Bcl-2), energy sensors (SIRT1, AMPK), and hypoxia inducible factor 1 alpha (HIF-1α) and (2) inhibitors including mammalian target for rapamycin (mTOR), NF-κB, and hypoxia inducible factor 2 alpha (HIF-2α). [See e.g., Lotz M, et al. (1999), "Mechanisms of chondrocyte apoptosis". *Osteoarthritis and Cartilage*, 7: 389-391; Lotz M and Carames B (2011). "Autophagy and Cartilage Homeostasis Mechanisms in Joint Health, Aging and Osteoarthritis". *Nat. Rev. Rheumatol.*, 7(10):579-587; Qin N, et al. (2017), "Local intra-articular injection of resveratrol delays cartilage degeneration in C57BL/6 mice by inducing autophagy via AMPK/mTOR pathway". *Journal of Pharmacological Sciences* 134:166-174; Hwang H S and Kim H A (2015), "Chondrocyte Apoptosis in the Pathogenesis of Osteoarthritis". *Int. J. Mol. Sci.*, 16:26035-26054.]

(4) Chondrocyte hypertrophy: Under normal condition, chondrocytes do not undergo further differentiation to hypertrophic cells. However, in a joint disease state and/or presence of triggers, chondrocytes transform into hypertrophic-chondrocytes. Instead of producing collagen and proteoglycans, these hypertrophic-like chondrocytes produce degrading enzymes (MMPs), and transcription factors, including Runx2 and VEGF, which are promoters of cartilage degradation and calcium deposition. In healthy AC, chondrocytes resist proliferation and terminal differentiation. In OA and under mechanical stress, chondrocytes proliferate and become hypertrophic, causing cartilage degradation by enhancing expression of MMPs and matric calcification. [See e.g., van der Kraan P M and van den Berg W B (2012), "Chondrocyte hypertrophy and osteoarthritis: role in initiation and progression of cartilage degeneration?" *Osteoarthritis and Cartilage* 20: 223e232; Thong L. et al. (2015), Ibid.; Kauguchi H (2016), Ibid.]

(5) Mitochondrial dysfunction: Mitochondrial dysfunction of chondrocytes causes functional abnormalities and apoptosis, which contributes to impaired ability of chondrocytes to produce ECM, oxidative stress, enhanced production of proteases and inflammatory cytokines, and degradation of matrix proteins. Chondrocytes mitochondrial dysfunction is mediated through multiple promoters such as NO, pro-inflammatory cytokines, oxidative stress, impaired autophagy, and decrease in adenine monophosphate activated protein kinase (AMPK) and Sirtuin 1 (SIRT1) expression and/or activation. [See e.g., Wang Y, et al. (2015), Ibid.]

(6) Oxidative stress: Oxidative stress has been shown to cause the development of OA by upregulating the expression of iNOS and NAD phosphate oxidase in chondrocytes. These results in matrix protein degradation, mitochondrial dysfunction, and chondrocytes hypertrophy and chondrocytes apoptosis. [See e.g., Kauguchi H (2016), Ibid.; Chin K Y and Pang K L (2017), "Therapeutic Effects of Olive and its Derivatives on Osteoarthritis: From Bench to Bedside". *Nutrients*.]

(7) Nitric Oxide (NO): Increase in nitric oxide in the cartilage has been demonstrated to inhibit synthesis of cartilage matrix (collagen and proteoglycans), to enhance activity of MMPs and to promote chondrocyte apoptosis. [See e.g., Pelletier J P, et al. (2001), Ibid.]

(8) Induction of pro-inflammatory cytokines (TNF-α, IL-6 and IL-1) expression and activation: Many of the triggers including aging and mechanical stress promote increase in proinflammatory cytokines production. These cytokines activate two major groups of proteinases, MMPs, and, aggrecanases, which breakdown the collagens and proteoglycans, respectively. In addition, these cytokines induce chondrocytes to produce more cytokines and MMPs, which promote the production of nitric oxide (NO), which has been shown to inhibit collagen and proteoglycan synthesis, to increase MMPs activity and to promote apoptosis of chondrocytes. In addition, these cytokines promote chondrocyte apoptosis by downregulating β1-integrin function and expression of the chondrocyte pro-survival kinase, i.e., extracellular signal-regulated kinase (ERK1/2). [See e.g., Gupta P K, et al. (2012), Ibid.; Pelletier J P, et al. (2001), Ibid.; Lotz M, et al. (1999), Ibid.; Wang A, et al. (2016), "Procyanidins Mitigate Osteoarthritis Pathogenesis by at Least in Part suppressing Vascular Endothelial Growth Factor Signaling". *Int. J. Mol. Sci.* 17.]

The present inventive compositions for treating and preventing development and progression of OA and RA are based on delineating the critical triggers, promoters, processes and mechanisms described above that lead to these debilitating conditions. Specifically the present compositions comprise a combination of bio-active agents that effectively prevents/arrests loss of and/or damage to the articular cartilage (AC) by suppressing (a) extracellular matrix (ECM) degradation, (b) chondrocyte apoptosis, and (c) inflammation of synovium.

The inventive compositions used for administration to human and other mammalian subjects having or at risk for development and/or progression of osteoarthritis (OA) and/or rheumatoid arthritis (RA) comprise (1) at least one agent that inhibits and/or suppresses expression and/or activity of one or more of inflammatory mediators including interleukins IL-1α, IL-1β, IL-6, NF-κB, TNF-α, matrix metalloproteinases (MMPs), prostaglandin E2 (PGE2), and nitric oxide (NO); (2) at least one agent that inhibits the activity of pro-oxidants including reactive nitrogen species (RNS) and reactive oxygen species (ROS) and/or upregulates expression and/or activity of antioxidants including glutathione (GS), superoxide dismutase (SOD) and catalase; (3) at least one agent that induces the expression of and/or activates one or more of AMPK (adenosine monophosphate-activated protein kinase, SIRT1 (sirtuin1), HIF-1α (hypoxia inducible factor 1 alpha), SOX9 (SRY-related protein 9), BMP-7 (bone morphogenetic protein 7), and ERK 1/2 (extracellular regulated kinase isoforms 1 and 2); (4) at least one agent capable of modulating expression and/or activity of one or more of Runx2 (Runt-related transcription factor 2 also known as core-binding factor subunit alpha-1), P38-MAPK (mitogen-activated protein kinase), HIF-2α (hypoxia inducible factor 2 alpha), and AP-1 (Activator protein 1); (5) at least one agent capable of modulating expression and/or activity of one or more of VEGF (vascular endothelial growth factor) and FGF (fibroblast growth factor); (6), at least one agent capable of modulating expression and/or activity of one or more of NMDAR (N-methyl-D-aspartic acid receptor), mTOR (mammalian target for rapamycin) and Wnt/β-catenin signaling pathway; and (7) at least one agent capable of inducing expression of and/or activating antiapoptotic proteins (including Bcl-2 and beclin) and/or suppressing proapoptotic proteins (including Bax, Bcl-2-associated X protein).

In one embodiment, the active agents used in the present compositions are natural products, specifically phytonutrients in combination with minerals and/or vitamins that have a long history of safety for human and mammalian consumption. It is emphasized that any one of these active agents may provide multiple activities or functions; thus in some embodiments the present combinations may comprise less than seven different agents to provide the seven specified activities. Preferably the present compositions comprise at least three phytonutrients, four phytonutrients, five phytonutrients and even six or more phytonutrients in various embodiments. Synergistic mechanisms result from the optimal combination of phytonutrient components, each one possessing multi-targeting biological effects and acting at different cellular, molecular and biochemical levels. The beneficial health effects of the present phytonutrients are potentiated in synergy with each other through complementing mechanisms. Studies have also suggested that delivering these compounds in combination improve the acute bioavailability of each component compared to supplementation with single compounds, allowing for lower overall doses and simpler treatment protocols using combination therapies, such as provided by the present compositions.

Compositions with combinations of such natural agents are efficacious to prevent, reduce or treat OA, RA and associated disorders or triggers including diabetes, obesity, oxidative stress and systemic inflammation. A first embodiment includes dietary supplements composed of a combination of phytochemicals and other nutrients, which work together synergistically or additively to deliver benefits in (1) preventing the development of and/or slowing/reversing the progression of OA and RA prior to the development of arthritis symptoms, (2) relieving OA and RA mediated pain and disability and importantly, (3) product safety.

While in the past decades a lot of progress has been made in understanding the pathogenesis of arthritis both at the cellular and molecular levels, pharmacological treatments to prevent and/or treat the development and progression of arthritis remain unavailable. At most, current pharmacological treatments such as analgesics and non-steroidal anti-inflammatory drugs (NSAIDS) relieve pain and improve function. Current treatment for arthritis (OA and RA) include a wide variety of medicines ranging from steroidal/nonsteroidal anti-inflammatory drugs (NSAIDs, corticosteroids such as prednisone and other pain killers) to potent biological agents targeting specific immune and inflammatory pathways, such as TNF-alpha (TNF-α) inhibitors and interleukin-1 receptor antagonists. Among NSAIDs, acetaminophen is most frequently used in fairly high doses (4000 mg/day). Other pain killers used include tramadol and other opioids (e.g., morphine). Examples of TNF-α inhibitors used for the treatment of severe RA include Etanercept, infliximab and rituximab. IL-1 receptor antagonists and methotrexate are other therapeutic choices for RA. While some of these therapies have proven to be somewhat effective in the majority of RA cases, the use of these drugs is accompanied by numerous and frequently serious side effects such as gastrointestinal ulcerations; hemorrhagic events; NSAID-induced nephrotoxicity; infusion hypersensitivity reactions; auto-immune responses (e.g., lupus-like syndrome) triggered by TNFα inhibitors; increased risk of severe infection affecting mainly the respiratory tract caused by biological drugs (anakinra, rituximab, or abatacept); and fatal cytopenia induced by methotrexate. Current therapies only treat the symptoms (e. g. pain, swelling and stiffness); they do not offer prevention and/or cure for OA and RA. By contrast to current therapies, the present compositions comprising a combination of phytonutrients, minerals and/or vitamins are safe and effective for treating and preventing the development and/or progression of OA and RA as well as for alleviating the symptoms of these debilitating diseases. As discussed above, the etiology of arthritis is complex and involves multiple triggers and mechanisms. It is important to recognize that the two culprits to arthritis development and progression: degradation of ECM by proteases and apoptosis of chondrocytes by caspases, are modulated by multiple triggers, modes of action and mechanisms. Thus, since the current approaches focus on a single trigger or mechanism, they fail to prevent or reverse arthritis. In fact, several clinical studies have demonstrated that targeting a single trigger and/or mechanism does not work, because of lack of efficacy and/or serious side effects. [See e.g., Mayo Clinic (2017), "Rheumatoid arthritis"; Dragos D, et al. (2017), "Phytomedicine in Joint Disorders". *Nutrients.* 9(1):70; Mobasheri A (2012), "Intersection of Inflammation and Herbal Medicine in the Treatment of Osteoarthritis". *Curr. Rheumatol. Rep.* 14(6): 604-616; Green J A, et al. (2014), "The potential for dietary factors to prevent or treat osteoarthritis". *Proceedings of the Nutrition Society,* 73(2): 278-288; Leong D J, et al. (2013), Ibid.; Goldring M B and Goldring S R (2007), Ibid.; Pelletier J P, et al. (2001), Ibid.; Lotz M, et al. (1999), Ibid.; Goldring M B, Marcu K B (2009), Ibid.; Kauguchi H (2016), Ibid.; Facchini A., et al. (2014), Ibid.; Lee H S and Salter D M (2015), Ibid.; FDA. "Medication Guide for Non-Steroidal Anti-Inflammatory Drugs (NSAIDs)"; Hwang H S and Kim H A (2015), Ibid;.]

The primary modes of action and mechanisms of some of the present natural bio-actives in promoting joint health and reducing development and progression and symptoms of OA and RA are illustrated in Table 1 below. These bio-actives prevent development and progression of and/or treat OA and RA by modulating mechanisms that involve transcription factors, growth factors, kinases, antiapoptotic/apoptotic factors and deacetylases. Through modulation of these activities, specifically downregulating inducers of OA/RA and upregulating promoters of joint health, the present combination of natural bio-actives provides a holistic approach to preventing and/or reducing the development and progression of these debilitating diseases. Together the present bio-actives (phytochemicals and other nutrients) provide the following additive and/or synergistic effects:

Inhibiting the accumulation of AGEs, which stimulates production of pro-inflammatory cytokines (IL-1β and TNF-α), proteinases (MMPs), NO and prostaglandin E2 (PGE2).

Inducing autophagy, which plays important role in ECM synthesis, chondrocyte survival, and energy production by removing damaged organelles and macromolecules, and nutrient supply.

Suppressing NO production, which inhibits cartilage matrix production (collagen and proteoglycans), enhances MMPs activation, and promote chondrocyte apoptosis.

Preventing hypertrophic-like chondrocyte formation, which induce the expression/activation of ECM degrading enzymes (MMPs), and the transcription factor, Runx2, which promotes ECM degradation, chondrocyte apoptosis, and ossification within the AC.

Inhibiting pro-inflammatory cytokines (TNF-α, IL-6 and IL-1) expression and activation, which stimulate production of MMPs, aggrecanases, NO, which cause chondrocytes apoptosis and ECM destruction.

Enhancing antiapoptotic (Bcl-2 and beclin) and suppressing proapoptotic proteins (Bax).

Increasing expression and/or activation of AMPK, SIRT1, HIF-1α, Sox9 and BMP-7 and upregulating expression and/or activation of antioxidants [glutathione (GS), superoxide dismutase (SOD) and catalase].

Inhibiting Runx2, P38-MAPK, ERK1/2, HIF-2α, VEGF, FGF, AP1, NMDAR, mTOR.

TABLE 1

Activities of Natural Agents That Promote Joint Health and Prevent RA and OA

| Bio-actives | Upregulate Promoters of joint health | | | | | | | |
|---|---|---|---|---|---|---|---|---|
| | Sox9 | BMP-7 | HIF-1α | AMPK | SIRT1 | ERK1/2 | Bcl-2 | Beclin |
| Resveratrol | ↑ | ↑ | ↑ | ↑ | ↑ | | ↑ | ↑ |
| Curcumin | | | | ↑ | ↑ | ↑ | ↑ | ↑ |
| EGCG | ↑ | | | ↑ | ↑ | | | |
| Quercetin | | | | ↑ | ↑ | | | |

| Bio-actives | Downregulate Inducers of arthritis | | | | | | | | | |
|---|---|---|---|---|---|---|---|---|---|---|
| | P38 MAPK | AP1 | VEGF | Bax | mTOR | Runx2 | HIF-2α | NMDAR | FGF | NF-κB |
| Resveratrol | | ↓ | | ↓ | ↓ | | ↓ | | ↓ | ↓ |
| Curcumin | ↓ | | | | | | | | | ↓ |
| Hydroxytyrosol | | | ↓ | | ↓ | | | | | |
| Procyanidins | | | ↓ | | | | | | | |
| Magnesium | | | | | | | | ↓ | | ↓ |
| EGCG | ↓ | ↓ | | | | | | | | ↓ |
| Quercetin | | | | | | | | | | ↓ |

In a first embodiment, the active agents used in the present compositions are natural products, specifically phytonutrients in combination with minerals and/or vitamins that have a long history of safety for human and mammalian consumption. It is to be understood that any one of these active agents may provide multiple activities or functions; thus in some embodiments the present combinations may comprise less than seven different agents. Preferably the present compositions comprise at least three phytonutrients, four phytonutrients, five phytonutrients and even six or more phytonutrients in various embodiments. Synergistic mechanisms result from the optimal combination of phytonutrient components, each one possessing multi-targeting biological effects and acting at different biochemical and metabolic levels. The beneficial health effects of the present phytonutrients are potentiated in synergy with each other through complementing mechanisms. Studies have also suggested that delivering these compounds in combination improve the acute bioavailability of each component compared to supplementation with single compounds, allowing for lower overall doses and simpler treatment protocols using combination therapies, such as provided by the present compositions.

Table 2 below shows examples of dietary/nutritional supplements specifically formulated to treat and/or prevent OA and RA and to promote overall joint health. These dietary supplements comprise phytonutrients and magnesium mineral as actives with amounts per serving shown. Some compositions may further comprise vitamins (such as D3 and K2) and other minerals such as calcium. Other optional components include S-Adenosyl-L-methionine; (SAM-e), glucosamine, chondroitin, methylsulfonylmethane, omega-3 fatty acids, and selenomethionine, which are common ingredients in currently marketed OTC dietary supplements. In particular, glucosamine and chondroitin are commonly used in joint health dietary supplements since these compounds are structural components of cartilage, the tissue that cushions the joints and both are produced naturally in the body. Researchers have studied the effects of these supplements, individually or in combination, on osteoarthritis. No serious side effects have been reported in large, well-conducted studies of people taking glucosamine, chondroitin, or both for up to 3 years.

The selection of preferred phytonutrient polyphenols such as quercetin, curcumin, EGCG, hydroxytyrosol, procyanidins and resveratrol and minerals (magnesium) are based in part on epidemiological studies that have shown a reduction in arthritis associated with increased consumption of fruits and vegetables that are rich sources of the present bio-actives, including polyphenols, vitamins and minerals. Several published in vitro, animal, and clinical studies have shown that these bio-actives have important joint health benefits mediated through their multiple modes of action and mechanisms. [See e.g., Leong D J, et al. (2013), Ibid.; Mobasheri A, et al. (2012), "Scientific Evidence and Rationale for the Development of Curcumin and Resveratrol as Nutraceutricals for Joint Health". *Int. J. Mol. Sci.* 13: 4202-4232; Mobasheri A (2013), "Osteogenic effects of resveratrol in vitro: Potential for the prevention and treatment of Osteoporosis". *Ann. N. Y. Acad. Sci.,* 1290:59-66; Shakibaei M (2011), "Resveratrol-mediated SIRT-1 Interactions with p300 Modulate Receptor Activator of NF-κB Ligand (RANKL) Activation of NF-κB Signaling and Inhibit Osteoclastogenesis in Bone-derived Cells". *The Journal of Biological Chemistry.* 286(13):11492-11505; Grover A K and Samson S E (2016), Ibid.; Csaki C, et al. (2009), Ibid.; Ansari M and Khan H A (2014), Ibid.; Facchini A. et al. (2014), Ibid.; Oliveira A L, et al. (2017), Ibid.]

Some of the phytonutrient components that may be used herein are pure materials either isolated from natural extracts or synthesized and some components are extracts, which may contain mixtures of active compounds. For example, Pycnogenol™ is a pine bark extract which contains procyanidin compounds; *Polypodium* (*Polypodium leucotomos* extract) contains calagualine, a triterpenoid glycoside and several phenolic acids; *Acacia* contains robinetinidol, fisetinidol, catechin and gallocatechin. Another example is soybean extract which contains isoflavones including about 37 percent daidzein, 57 percent genistein and 6 percent glycitein. In situations where it is convenient and/or cost effective, natural extracts may be substituted for pure compounds without markedly diminishing their effectiveness. For example, mangiferin may be replaced with extracts of *Mangifera indica* (mango) or the genus *Salacia*; beta-boswellic acid by *Boswellia Serrata* extract; salicortin by *Populus balsamifera* or *Salix alba* (white willow) extract. Genistein and daidzein may be replaced with soy extract. Preferred phytochemicals (phytonutrients) and other bioactives for use herein and in compositions formulated to provide benefits against associated conditions including vascular calcification, diabetes, obesity and osteoporosis are described in more detail below. Table 3 below shows details of the modes of actions of some preferred bio-actives against OA and RA.

Phytonutrients (Phytochemicals)

Among phytonutrients useful in the present invention are the flavonoids and other polyphenols. Flavonoids or bioflavonoids, also known as "phenylchromones", are naturally occurring, water-soluble compounds known to have antioxidant characteristics. Flavonoids are widely distributed in plants and are found in numerous vegetables, fruits and beverages such as tea and wine (particularly red wine) and therefore, are a common component of the human diet. The animal kingdom is unable to synthesize the flavone nucleus; flavonoids are therefore strictly exogenous food components of plant origin.

Flavonoids are conjugated aromatic compounds having the general structure of a 15-carbon skeleton, which consists of two phenyl rings (A and B) and a dihydropyran heterocyclic ring (C). Flavonoids are all ketone-containing compounds, such as flavones and flavonols (also referred to as anthoxanthins). This class was the first to be termed bioflavonoids. The terms flavonoid and bioflavonoid have also been more loosely used to describe non-ketone polyhydroxy polyphenol compounds, which are more specifically termed flavanoids. Flavonoids (specifically flavanoids such as the catechins, and their oligomeric forms, proanthocyanidins) are the most common group of polyphenolic compounds in

TABLE 2

Dietary Supplement Compositions for Joint Health

| Bio-actives (mg) | Formula 1 | Formula 2 | Formula 3 | Formula 4 | Formula 5 | Formula 6 |
|---|---|---|---|---|---|---|
| Resveratrol | 100 | 100 | 100 | 100 | 100 | 100 |
| Curcumin* | 120 | 120 | 120 | 120 | 120 | 120 |
| Hydroxytyrosol** | 25 | 25 | | | | |
| Magnesium | 200 | 200 | 200 | 200 | 200 | 200 |
| EGCG | | 150 | | 150 | 150 | 150 |
| Quercetin*** | | | 50 | | | |
| Glucosamine | | | | 200 | | |
| Chondroitin | | | | | 200 | |
| S-adenosylmethionine | | | | | | 200 |

*As Theracurmin ®,
**As OOE containing 20% or more hydroxytyrosol,
***As EMIQ.

the human diet and are found ubiquitously in plants. Flavonols, the original bioflavonoids such as quercetin, are also found ubiquitously, but in lesser quantities. The widespread distribution of flavonoids, their variety and their relatively low toxicity compared to other active plant compounds such as some alkaloids mean that humans and animals can ingest significant quantities in their diet. Foods with high flavonoid content include parsley, onions, blueberries and other berries, apples, tea, bananas, all citrus fruits, red wine, and dark chocolate.

As of the mid 1980's more than 4000 chemically unique flavonoids have been identified and this is only a fraction of the total number likely to be present in nature. The most widely occurring flavonoids are flavones and flavonols. While the present invention is open to the use of all flavonoids, flavonols such as myricetin, (3,5,7,3',4',5',-hexahydroxyflavone), quercetin (3,5,7,3',4'-pentahydroxyflavone), kaempferol (3,5,7,4'-tetrahydroxyflavone), and flavones such as apigenin (5,7,4'-trihydroxyflavone) and luteolin (5,7,3',4'-tetrahydroxyflavone) and glycosides thereof are preferred. The main catechins are catechin [(2R, 3S)-2-(3,4-dihydroxyphenyl)-3,4-dihydro-2H-chromene-3, 5,7-triol], the cis isomer epicatechin (EC), procyanidins, epicatechin gallate (ECG), epigallocatechin-3-gallate (EGCG) and epigallocatechin (EGC). Although all catechins share similar properties, EGCG and procyanidins appear to be most potent. Some other isomers or conjugates may be present in plant sources (with either catechin or epicatechin as a backbone, and varying levels of gallic acids). Other polyphenolic compounds for use herein are structurally not flavonoids, i.e., do not contain the 15-carbon ring structure but contain the phenol functional group and may also contain the ketone group. Examples include genistein (5,7-Dihydroxy-3-(4-hydroxyphenyl)chromen-4-one); daidzein (7-Hydroxy-3-(4-hydroxyphenyl) chromen-4-one); magnolol [4-Allyl-2-(5-allyl-2-hydroxy-phenyl)phenol]; curcumin [(1E,6E)-1,7-Bis(4-hydroxy-3-methoxyphenyl)-1, 6-heptadiene-3,5-dione; hesperitin (5,7,3'-trihydroxy-4'-methoxyflavanone); hesperidin (hesperitin-7-O-rutinoside); mangiferin R1S)-1,5-anhydro-1-(1,3,6,7-tetrahydroxy-9-oxo-9H-xanthen-2-yl)-D-glucitol]; salacinol R2S,3S)-4-[(2R,3S,4S)-3,4-dihydroxy-2-(hydroxymethyl)thiolan-1-ium-1-yl]-1,3-dihydroxybutan-2-yl] sulfate]; kotalanol R2S, 3S,4R,5R,6S)-1-[(2R,3S,4S)-3,4-dihydroxy-2-(hydroxymethyl)thiolan-1-ium-1-yl]-2,4,5,6,7-pentahydroxyheptan-3-yl] sulfate]; resveratrol (3,5,4'-trihydroxy-trans-stilbene; oleuropein [methyl (4S,5E,6S)-4-[2-[2-(3,4-dihydroxyphenyl)ethoxy]-2-oxoethyl]-5-ethylidene-6-R2S,3R,4S,5S,6R)-3,4,5-trihydroxy-6-(hydroxymethyl)oxan-2-yl]oxy-4H-pyran-3-carboxylate]; hydroxytyrosol (4-(2-Hydroxyethyl)-1,2-benzenediol); oleocanthal [2-(4-hydroxyphenyl)ethyl (3S,4E)-4-formyl-3-(2-oxoethyl)hex-4-enoate]; Fisetinidol [(2R,3S)-2alpha-(3, 4-Dihydroxyphenyl)-3,4-dihydro-2H-1-benzopyran-3beta, 7-diol]; Robinetinidol [(−)-5-[(2R)-3,4-Dihydro-3beta,7-dihydroxy-2H-1-benzopyran-2alpha-yl]-1,2,3-benzenetriol]; eugenol [2-methoxy-4-(2-propenyl)phenol]; (6)-shogaol [(E)-1-(4-Hydroxy-3-methoxyphenyl)dec-4-en-3-one]; with anolides (5,6-Epoxy-4,20,22-trihydroxy-1-oxoergosta-2,24-dien-26-oic acid delta-lactone); rosmarinic acid [((2R)-3-(3,4-Dihydroxyphenyl)-2-{[(2E)-3-(3,4-dihydroxyphenyl)-2-propenoyl]oxy}propanoic acid)]; boswellic acids (e.g, beta-boswellic acid); gingerol [(S)-5-hydroxy-1-(4-hydroxy-3-methoxyphenyl)-3-decanone]; lutein (β,ε-carotene-3,3'-diol); zeaxanthin (β,β-carotene-3,3'-diol). These flavonoids and other polyphenols are preferred because each agent provides multiple biologic, therapeutic and health activities/benefits. Other phytonutrients having different chemical structures from the above flavonoids and polyphenols but having therapeutic activities are also useful herein such as certain alkaloids like berberine [5,6-dihydro-9,10-dimethoxybenzo[g]-1,3-benzodioxolo[5,6-a]quinolizinium]. Another agent of interest is the fern extract commonly known as *Polypodium*, which has powerful antioxidant and anti-inflammatory activities and has been reported as useful for protecting skin tissue. *Polypodium leucotomos* (correctly *Phlebodium aureum*) extract contains calagualine and phenolic acids such as 3,4-dihydroxybenzoic acid, 4-hydroxybenzoic acid hydroxycinnamic acids. Because the present formulations use a combination of the above natural compounds having multiple activities, smaller amounts of each active are sufficient for therapeutic effectiveness while minimizing potential dose-dependent side effects. In addition, synergy is achieved with certain combinations. Preferred phytonutrients are described in more detail below.

Quercetin

A preferred flavonoid for use in the invention is quercetin, which is found in many fruits and vegetables, but highest levels are found in apples, cranberries, onions, kale and broccoli. Like many other bioflavonoids, quercetin has been promoted for its anti-oxidant, anti-inflammatory, anti-atherogenic, cardioprotective, and anti-carcinogenic properties. Quercetin is ingested from the daily diet, and also widely marketed as a dietary supplement in the U.S. and Europe at doses ranging from 500 to 2000 mg per day. Beneficial effects of quercetin supplements have been reported in clinical trials. Evaluation by the International Agency for Research on Cancer (IARC) concluded that quercetin is not classified as carcinogenic to humans. Quercetin has received GRAS (Generally Recognized As Safe) status, and no side effects have yet been noted in doses of a few grams a day in either humans or animals. Quercetin may be also supplied in the present compositions as its glycosides including rutin (quercetin-3-O-rutinoside), quercitrin (quercetin-3-rhamnoside), isoquercetin (quercetin-3-glucoside aka isoquercitrin) and alpha-glycosyl isoquercetin (aka EMIQ or Enzymatically Modified Isoquercitrin). The glycosides are preferred for use herein because of their greater water solubility and absorbability and thus bioavailability as compared to quercetin itself.

It is believed that quercetin, which exhibits some of the strongest antioxidant effects of the flavonoids and which has been reported to inhibit oxidation and cytoxicity of low density lipoproteins (LDL), may have beneficial health consequences since oxidized low density lipoproteins are reported to be atherogenic, i.e., they contribute to the buildup of fatty substances in the arterial wall. Lipid peroxidation is caused by free radicals such as reactive oxygen species (ROS). Free radicals are molecules with at least one unpaired electron, which makes them highly reactive. Free radicals are continually formed in the metabolic processes of the human body but are tightly regulated. Human plasma contains various antioxidants which makes it difficult for such reactions to occur within the plasma. When LDL is within the arterial wall, the situation is different and the plasma antioxidant protection is not available. The reaction that can result in buildup of oxidized lipids in the arterial wall can be stopped or decreased by the presence of an antioxidant such as a flavonoid. Flavonoids appear to act by protecting LDL against oxidation, as they inhibit the generation of lipid peroxides and also may help protect alpha-tocopherol (vitamin E), a major lipophilic antioxidant carried in lipoproteins, from being consumed by oxidation in LDL. The activities of quercetin and other phytonutrients that are beneficial against vascular calcification, cardiovascular diseases, diabetes, obesity and other comorbidities are discussed in parent U.S. Pat. Nos. 1,564,084 filed on Jul. 13, 2017 and 1,567,486 filed on Aug. 11, 2017.

Against osteoporosis, a useful activity of quercetin as well as of other flavonoids and polyphenols (e.g., magnolol and honokiol, psi-baptigenin, apigenin, hesperidin, amorfrutins, and catechins) is their function as potent agonists to peroxisome proliferator activated protein receptor gamma (PPAR-γ) [See e.g., Wang L., et al. (2014). "Natural product agonists of Peroxisome proliferator-activated receptor gamma (PPAR-γ): a review". Biochemical Pharmacology 92: 73-89]. Other quercetin actions that are beneficial against osteoporosis include (1) inducing expression of Runx2, Osterix, BMP2, Wnt/β-catenin signaling, and extracellular protein kinases 1 and 2 (ERK1/2) signaling thereby increasing osteoblast differentiation from MSCs; (2) suppressing the production of pro-inflammatory cytokines (e.g., TNF-α, IL-1, IL-6) produced by microphages and adipocytes, and RANKL, produced by pre-osteoblasts and osteoblast, and inducing expression of OPG, which binds to RANKL thereby inhibiting RANK and osteoclast differentiation and promoting apoptosis of osteoclasts; (3) down-regulating PPAR-γ and C/EBP, which promote adipocyte differentiation at the expense of osteoblastogenesis and inducing AMPK and Wnt/β-catenin signaling (inhibitors of adipogenesis), thereby suppressing adipocyte differentiation, while favoring osteoblast differentiation. These are the same activities that are beneficial against obesity along with inducing pre-adipocytes apoptosis by enhancing caspase 3 and reducing oxidative damage by quenching reactive oxygen species (ROS) and enhancing production of endogenous antioxidants.

These activities of quercetin have been documented in several studies. [See e.g., Sharan K, et al. (2009). "Role of phytochemicals in the prevention of Menopausal bone loss: Evidence from in vitro, in vivo, human interventional and pharmacokinetic studies". Current Med. Chem. 16: 1138-1157; Wang R W K and Rabie A B M (2008). "Effect of Quercetin on Bone Formation". Journal of Orthopaedic Research, 1061-1066; Zhou Y, et al. (2015), "The Effect of Quercetin on the Osteogenesic Differentiation and Angiogenic Factor Expression of Bone Marrow-Derived Mesenchymal Stem Cells". PLOS ONE 0129605; Cao J J (2011). Effect of Obesity on Bone Metabolism. J. Orthopaedic Surgery and Res. 6(30): 1-7; Yamaguchi M and Weitzmann N (2011), "Quercetin, a potent suppressor of NF-κB and Smad activation in osteoblasts". Int. J. Molecular Medicine 28:521-525; Wattel A, et al. (2004), "Flavonoid Quercetin Decreases Osteoclastic Differentiation Induced by RANKL via a Mechanism Involving NF-κB and AP-1". Journal of Cellular Biochemistry, 92:285-295; Aguirre L, et al. (2011), "Beneficial Effects of Quercetin on Obesity and Diabetes". The Open Nutraceuticals Journal, 4:189-198; Zhou J, et al. (2014), "Isoquercitrin activates the AMP-activated protein kinase (AMPK) signal pathway in rat H4IIE cells". Complementary and Alternative Medicine, 14: 42; González-Castejón M, and Rodriguez-Casado A (2011), "Dietary Phytochemicals and their Potential Effects on Obesity". Pharmacological Research 64: 438-455; Baboota R K, et al. (2013), "Functional food ingredients for the management of obesity and associated co-morbidities—A review". Journal of Functional Foods, 5:997-1012; Chen S, et al. (2016), "Therapeutic Effects of Quercetin on Inflammation, Obesity, and Type 2 Diabetes". Mediators of Inflammation. 2016: 5pp; Dong J, et al. (2014), "Quercetin reduces obesity-associated ATM infiltration and inflammation in mice: a mechanism including AMPKα1/SIRT1". J. Lipid Res. 55(3):363-374.]

Quercetin and other polyphenols such as curcumin and magnolol also possess potent antibacterial activity in addition to their anti-oxidant and anti-inflammatory properties. For example, potent activity against oral pathogens responsible for gingivitis and periodontitis has been documented in published studies supporting their use in oral care formulations to help control gum disease. Some polyphenols are more active than others and some combinations do better than single agents. These polyphenols are active in killing bacteria as well as in controlling biofilm maturation and growth. The beneficial effects of quercetin and other polyphenols against inflammatory processes and immune responses are also well established, thereby enhancing their therapeutic potency. In vitro studies using different cells have shown that quercetin can inhibit production of inflammatory cytokines such as IL-6, IL-8 and TNF-α from human cultured mast cells and immunoglobulin E (IgE)-mediated release of histamine. [See e.g., Shahzad M et al. (2015), "Selected dietary (poly)phenols inhibit periodontal pathogen growth and biofilm formation". Food Funct. 6: 719; Palaska I, et al. (2013), "Use of Polyphenols in Periodontal Inflammation". European J. Pharmacology 720: 77-83; Min Y D, et al. (2007), "Quercetin inhibits expression of inflammatory cytokines through attenuation of NF-kappaB and p38 MAPK in HMC-1 human mast cell line". Inflamm. Res. 56(5): 210-5; Theoharides T C, et al. (2001), "Anti-inflammatory actions of flavonoids and structural requirements for new design". International Journal of Immunopathology and Pharmacology, 14(3):119-127; Kimata S, et al. (2000), "Effects of luteolin, quercetin and baicalein on immunoglobulin E-mediated mediator release from human cultured mast cells". Clinical & Experimental Allergy, 30(4): 501-508; Askari G, et al. (2012), "The effect of quercetin supplementation on selected markers of inflammation and oxidative stress". J. Res. Med. Sci., 17(7): 637-641.]

Curcumin

Curcumin is a yellow-orange pigment obtained from the plant Curcuma longa (turmeric) by making a powder of the dried rhizomes of the plant. It is a common ingredient in curry powders and has a long history of use in traditional Asian medicine and cooking. It is sold as an herbal supplement, cosmetics ingredient and as food flavoring and food coloring, thus being safe for human consumption. It is listed as food additive E100 in European Commission. "Food Additives". (2014 Feb. 15). Two preliminary clinical studies in cancer patients consuming high doses of curcumin (up to 8 grams per day for 3-4 months) showed no toxicity, though some subjects reported mild nausea or diarrhea. In vitro tests suggest curcumin has quite a large safety threshold. [See e.g., Goel A; et al. (2008). "Curcumin as "Curecumin": From kitchen to clinic". Biochemical Pharmacology 75 (4): 787-809; Hsu C H and Cheng A L (2007), "Clinical studies with curcumin". Advances in Experimental Medicine and Biology 595: 471-480.]

In addition to its antibacterial activity along with quercetin, curcumin has also been demonstrated to have potent antifungal activity against 23 fungi strains including Candida species at a fairly low concentration and to have an inhibitory effect on the adhesion of Candida species to human buccal epithelial cells. Since the adhesion of microorganisms to host mucosal surfaces is a prerequisite for colonization and infection, these results indicate that curcumin is a promising lead antifungal agent with none of the many side effects associated with the restricted number of commercially available antifungal drugs. [Martins C V B, et al. (2008), "Curcumin as a promising antifungal of clinical interest". *Journal of Antimicrobial Chemotherapy,* 63:2, 337-339.] The broad antimicrobial activity of curcumin along with its anti-inflammatory and antioxidant effects makes it applicable in many cosmetic, skin and hair care products. Examples include anti-dandruff shampoos, anti-aging skin creams, exfoliating cleansers, and anti-acne treatment. [See e.g., Mukherjee P K, et al. (2011), "Bioactive compounds from natural resources against skin aging". *Phytomedicine,* 19:64-73; Shimatsu A, et al. (2012), "Clinical Application of Curcumin, A Multi-Functional Substance". *Anti-Aging Med.,* 9(1): 43-51.]

Other areas of interest as it pertains to curcumin are alleviating cognitive decline associated with aging, reducing lipid and plaque levels in arteries and both reducing the risk of diabetes and being a good treatment for the side-effects associated with diabetes.

Consequently, curcumin is marketed as a supplement worldwide at concentrations ranging from 400-1000 mg. The European Food Safety Authority has concluded that curcumin when taken orally as food additive is safe for children age 1-10 years at dosages of 3 mg/kg body weight/day. Furthermore, the WHO made a recommendation that curcumin is safe for adults when taken at 150 mg/day. Also, the US FDA issued GRAS status to Curcumin C3 Complex produced by Sabinsa Corp. for use in food and beverage products.

Curcumin inherently is poorly absorbed when orally ingested by itself; thus bioavailable or absorbable forms are preferred for use in the present compositions. For example, the combination of curcumin with a small amount of piperine has been shown to increase the bioavailabity of curcumin 20-fold. [Shoba G, et al. (1998), "Influence of piperine on the pharmacokinetics of curcumin in animals and human volunteers". *Planta Med.* 64(4):353-6.] Other bioavailable forms of curcumin include a phospholipid-curcumin complex marketed as Meriva™ or Longvida™; a nanoparticulate emulsion such as Theracurmin™; a mixture of curcuminoids in their natural ratio found in turmeric prepared using a molecular dispersion process (CurcuWIN™); and a curcumin+turmeric essential oil mixture known as BCM-95 (BIOCURCUMIN™). [See e.g., Sunagawa Y, et al. (2015), "Colloidal Submicron Particle Curcumin Exhibits High Absorption Efficiency—A Double-Blind, 3-Way Crossover Study". *J. Nutr. Vitaminol.* 61: 37-44]

The activities of curcumin and mechanisms of action are somewhat similar to that of quercetin with regard to its benefits against vascular calcification, diabetes, obesity and osteoporosis. Both inhibit inflammatory responses, reduce oxidative stress, and inhibit pre-adipocyte differentiation via activation of AMPK and Wnt/β-catenin signaling while down-regulating the expression of PPAR-γ, C/EBPα, and SREBP-1 in adipocytes. Curcumin also induces adiponectin production in adipose tissue, which promotes fat oxidation, glucose uptake and insulin sensitivity. Curcumin further increases osteoblast differentiation from MSCs by upregulating the expression of Runx2, BMP2 and Wnt/β-catenin signaling; inhibits osteoclast differentiation; and induces apoptosis of osteoclasts by inhibiting pro-inflammatory cytokines (NF-kB, TNF-α, IL-6, IL-1α) and oxidative stress. [See e.g., Gu Q, et al. (2012), Ibid; Wang S, et al. (2014), "Novel insights of dietary polyphenols and obesity". *J. Nutr. Biochem.,* 25(1):1-18; Ejaz A, et al. (2009), "Curcumin Inhibits Adipogenes is in 3T3-L1 Adipocytes and Angiogenesis and Obesity in C57/BL Mice". *J. Nutr.* 139: 919-925; Cheng M, et al. (2016), Ibid; Ahn J, et al. (2010). "Curcumin-induced suppression of adipogenic differentiation is accompanied by activation of Wnt/−catenin signaling". *Am. J. Physiol. Cell Physiol.* 298: C1510-C1516; Zhang D, et al. (2013), "Curcumin and Diabetes: A Systematic Review". *Evidence Based Complementary and Alternative Medicine* 636053; Ghorbani Z, et al. (2014), "Anti-Hyperglycemic and Insulin Sensitizer Effects of Turmeric and Its Principle Constituent Curcumin". *Int. J. Endocrinol. Metab.* 12(4):e18081.]

Resveratrol

Resveratrol (3,5,4'-trihydroxy-trans-stilbene) is a stilbenoid, a type of natural polyphenol, produced by several plants. Sources of resveratrol in food include the skin of grapes and berries, peanuts and red wine. Like other plant polyphenols, resveratrol has potent antioxidant and anti-inflammatory activities. These activities among others have been implicated to contribute substantially to the health benefits of resveratrol. Studies have demonstrated resveratrol's capacity to favorably modulate factors involved in a number of disease models, including vascular calcification (VC), cardiovascular disease, diabetes, obesity, systemic inflammation, cancer and neurodegenerative diseases. [See e.g., Baur J A and Sinclair D A (2006). "Therapeutic potential of resveratrol: the in vivo evidence". *Nat. Rev. Drug Discov.* 5: 493-506; Juhasz B, et al. (2010), "Resveratrol: a multifunctional cytoprotective molecule". *Curr. Pharm. Biotechnol.* 11:810-818; Ning Xia, et al. (2017), "Antioxidant effects of resveratrol in the cardiovascular system". *British J. Pharmacology,* 174(12):1633-1646; Vogelman B (March 2012), "How Resveratrol Combats Leading Causes of Death". *Life Extension Magazine*; Vang O, et al. (2011), "What is new for an old molecule? Systematic review and recommendations on the use of resveratrol". *PLOS One.* 6(6):e19881.]

With regard to conditions that are associated with obesity and diabetes, resveratrol has been shown to reduce risks for these conditions by targeting multiple factors that set the stage for such. Animal studies in pigs have shown that resveratrol helps mitigate the cholesterol elevations that result from obesity and a high-fat diet by directly regulating expression of genes that control lipid metabolism. Exposure to resveratrol triggers correction of abnormal fatty acid utilization, by inducing mitochondrial enzymes that help break down fat molecules. In pigs with the equivalent of human metabolic syndrome, resveratrol supplementation lowered body mass indices, serum cholesterol and the inflammatory marker C-reactive protein and improved glucose tolerance and endothelial function. [See e.g., Azorin-Ortuno M, et al. (2012), "Effects of long-term consumption of low doses of resveratrol on diet-induced mild hypercholesterolemia in pigs: a transcriptomic approach to disease prevention". *J. Nutr. Biochem.* 23(7):829-37; Bastin J, et al. (2011), "Exposure to resveratrol triggers pharmacological correction of fatty acid utilization in human fatty acid oxidation-deficient fibroblasts". *Hum. Mol. Genet.* 20(10): 2048-57; Robich M P, et al. (2011), "Resveratrol modifies risk factors for coronary artery disease in swine with metabolic syndrome and myocardial ischemia". *Eur. J. Pharmacol.* 664(1-3):45-53.]

Several studies have reported that supplementation with resveratrol reduces blood glucose, increases insulin sensitivity, restores insulin secretion, and prevents glucose resistance. These resveratrol effects arise via (1) increasing adiponectin expression, which improves insulin sensitivity in adipocytes; (2) increasing AMPK activity and SIRT1 thereby enhancing energy expenditure/thermogenesis, which mimics calorie restriction without affecting calorie intake; (3) inducing the expression of GLUT4 thereby increasing glucose uptake; and (4) reducing the expression of inflammatory response (TNF-kB, IL-6, and COX-2) in mature adipocytes. With regard to controlling obesity, resveratrol has been shown to (1) activate AMPK and down regulate the expression of PPAR-γ resulting in decreasing adipocyte differentiation (adipogenesis) and proliferation, (2) activate SIRT1 in addition to AMPK and down regulate expression of FAS and SREBP-1 resulting in lipogenesis inhibition and promotion of lipolysis and thermogenesis; (3) enhance apoptosis; (4) reduce the expression of inflammatory response (TNF-kB, IL-6, and COX-2) in mature adipocytes; and (5) reduce the expression of mediators of reactive oxygen species (ROS) thereby reducing oxidative stress. [See e.g., Vallianou N, et al. (2013), "Resveratrol and Diabetes". *Rev. Diabet. Stud.* 10: 236-242.6; Fischer-Posovszky, P, et al. (2010), "Resveratrol regulates human adipocyte number and function in a Sirt1 dependent manner". *Am. J. Clin. Nutr.* 92:5-15; Wang A, et al. (2011), "Up-regulation of Adiponectin by Resveratrol". *The Journal of Biological Chemistry.* 286: 60-66; Wang S, et al. (2014), Ibid.; González-Castejón M, and Rodriguez-Casado (2011) Ibid.; Baboota R K, et al. (2013), Ibid.] The same beneficial activities of resveratrol against obesity and diabetes are also beneficial against osteoporosis. These include (1) suppressing suppressing/inhibiting PPAR-γ and C/EBP expression and activity and thus adipocyte differentiation and (2) inducing the expression and/or activation of bone transcription factors Runx2/Cbfα1 and Sirtuin 1 (Sirt 1), Wnt/β-catenin and ERK1/2 signaling, all leading to increased differentiation of mesenchymal stem cells (MSCs) to osteoblasts. MSCs are the precursors for both adipocytes and osteoblasts. With aging, differentiation to adipocytes dominates over the differentiation to osteoblasts in bone marrow, contributing to lower bone mass and the increased tendency for fractures to occur in the elderly. Thus, an inverse relationship exists between adipocytes and osteoblasts in the bone marrow. Resveratrol acts on several molecular targets in adipocytes and osteoblasts leading to a decrease in adipocyte number and size and an increase in osteogenesis (bone building). Furthermore, it has been shown that resveratrol in combination with other phytochemicals such as quercetin and genistein and synergistically decreased adipogenesis in murine and human adipocytes. A recent in vivo study also showed that phytochemicals including resveratrol in combination with vitamin D prevented weight gain and bone loss in a postmenopausal rat model. Therefore, combinations of resveratrol with other phytochemicals and/or minerals are contemplated herein as treatment for osteoporosis as well as obesity.

Resveratrol also inhibits osteoclast differentiation and promotes apoptosis of osteoclasts by (a) inhibiting pro-inflammatory cytokines (e.g., TNF-α and IL-6), RANK and RANKL via Sirt 1 activation, and (b) binding to estrogen receptors without having the side effects mediated by estrogen. Note that hormone replacement therapy (HRT) with estrogen has been an established treatment of bone mineral loss and osteoporosis, but there are concerns that HRT has several adverse side effects and can increase the risk of cancer, heart disease, and stroke. In vitro studies have demonstrated that resveratrol-activated Sirt-1 plays pivotal roles in regulating the balance between the osteoclastic versus osteoblastic activity resulting in bone formation thereby highlighting the benefits from resveratrol for treating osteoporosis and rheumatoid arthritis-related bone loss. [See e.g., Mobasheri A and Shakibaei M (2013), "Osteogenic Effect of Resveratrol In Vitro: potential for the Prevention and Treatment of Osteoporosis". *Ann. N. Y. Acad. Sci.*, 1290: 59-66; Sharan K, et al. (2009), "Role of phytochemicals in the prevention of Menopausal bone loss: Evidence from in vitro, in vivo, human interventional and pharmacokinetic studies". *Current Med. Chem.* 16: 1138-1157; Shakibaei M, et al. (2011), Ibid.; Rayalam S, et al. (2011), "Synergism between resveratrol and other phytochemicals: Implications for obesity and osteoporosis". *Mol. Nutr. Food Res.*, 55: 1177-1185; Rayalam S, et al. (2008), "Resveratrol induces apoptosis and inhibits adipogenesis in 3T3-L1 adipocytes". *Phytother. Res.* 22(10):1367-71.]

Oleuropein and Hydroxytyrosol

Olive plant (*Olea europaea*) leaves have been widely used in traditional remedies as well as in human diet as an extract, in herbal tea and in the powder form in the European and Mediterranean countries. Olive leaves extract (OLE) is marketed as a natural nutraceutical with wide-ranging health benefits. Olive leaves contain several different compounds collectively termed as olive biophenols, which impart health and therapeutic properties. The most abundant biophenol is oleuropein, followed by other biophenols such as verbascoside, luteolin, rutin, catechin, and hydroxytyrosol in lower quantities. High amounts of oleuropein (OL) and its main derivative hydroxytyrosol (HT, 3,4-dihydroxyphenyl ethanol) are released from the olive fruit during the extraction process to produce olive oil extract (OOE, also referred as VOO, virgin olive oil). Chemically, oleuropein is an ester of hydroxytyrosol.

In recent years, research has focused on the effects of OLE and OOE related to the prevention of obesity and diabetes as well as associated conditions such as hypertension, atherosclerosis and other cardiovascular diseases. OL and HT represent the molecules of major interest for their biological and pharmacological properties and beneficial effects, related for example, to their antioxidant activity in many preclinical models of diseases. The antioxidant activity of OL and HT in vivo is related to their high bioavailability. Various studies have documented a high degree of absorption, fundamental to exert their metabolic and pharmacokinetics properties. OL and HT behave as antioxidants acting as: (1) free radical scavengers and radical chain breaking; (2) anti-oxygen radicals; and (3) metal chelators. With their catecholic structure, they are able to scavenge the peroxyl radicals and break peroxidative chain reactions producing very stable resonance structures.

Animal studies have also demonstrated that addition of oleuropein to a high fat diet (HFD) decreased body weight gain and improved the lipid profiles in the plasma of mice. These beneficial effects against obesity in mice appear to be mediated, at least in part, through downregulating the expression of molecules involved in adipogenesis (PPAR-γ and C/EBPα) and upregulating the expression of factors (AMPK and Wnt/β-catenin signaling) involved in thermogenesis and fat oxidation in the visceral adipose tissue of HFD-fed mice. Other effects of oleuropein supplementation resulted in significantly lower concentrations of triglyceride, total cholesterol, LDL+VLDL cholesterol, free fatty acids (FFA), glucose, and leptin in the plasma of HFD-fed mice. Other studies have reported that oral administration of oleuropein (as olive leaves extract) decreased serum glucose, hemoglobinA1c (HbA1c), total cholesterol, triglycerides, urea, uric acid, creatinine, aspartate amino transferase (AST) and alanine amino transferase (ALT) and increased serum insulin in diabetic rats. It is hypothesized that the hypoglycemic activity of oleuropein result from stimulating AMP activated protein kinase (AMPK) and inducing GLUT4 resulting in enhanced insulin sensitivity and increased peripheral uptake of glucose. It has also been suggested that the antidiabetic and anti-obesity effects of oleuropein might be due to its antioxidant activity restraining the oxidative stress and inflammation which are widely associated with diabetes and obesity pathologies and complications. [See e.g., Kim Y, et al. (2010), "Hepatoprotective effect of oleuropein in mice: mechanisms uncovered by gene expression profiling". *Biotechnology Journal*. 5(9):950-960; Eidi A, et al. (2009), "Antidiabetic effect of *Olea europaea* L. in normal and diabetic rats". *Phytotherapy Research*. 23(3):347-350; Gonzalez M, et al. (1992), "Hypoglycemic activity of olive leaf". *Planta Med*. 58:513-5; Jemai H, et al. "Antidiabetic and antioxidant effects of hydroxytyrosol and oleuropein from olive leaves in alloxan-diabetic rats". *J. Agric. Food Chem*. 57: 8798-804; Hadrich F et al. (2016), "Oleuropein activated AMPK and induced insulin sensitivity in C2C12 muscle cells". *Life Sci*. 151: 167-73; Lee-Huang S, et al. (2013), "Oleuropein and Related Compounds from Olive Plants Modulate Adipogenesis". *The Open Conference Proceedings Journal*. 4: 113-124; Shen Y, et al. (2014), "Olive Leaf Extract Attenuates Obesity in High-Fat Diet-Fed Mice by Modulating the Expression of Molecules Involved in Adipogenesis and Thermogenesis". *Evidence-Based Complementary and Alternative Medicine*, 2014: 971890, 12 pages http://dx.doi.org/10.1155/2014/971890; Ebaid G, et al. (2010), "Effects of olive oil and its minor phenolic constituents on obesity-induced cardiac metabolic changes". *Nutrition Journal* 9:46; Qadir N M, et al. (2016) "Antidiabetic Effect of Oleuropein from *Olea europaea* Leaf against Alloxan Induced Type 1 Diabetic in Rats". *Braz. Arch. Biol. Technol. v.* 59: e16150116.]

As with resveratrol, quercetin and curcumin described above, oleuropein also has activities that are beneficial against osteoporosis. These include inducing Runx2 and Osterix expression that lead to increased osteoblast differentiation; increasing OPG and inhibiting RANKL and pro-inflammatory cytokines such as TNF-α thereby inhibiting osteoclast differentiation; and suppressing/inhibiting PPAR-γ expression and activity, thereby suppressing adipocyte differentiation, while favoring osteoblast differentiation. [See e.g., Santiago-Mora R, et al. (2011). "Oleuropein enhances osteoblastogenesis and inhibits adipogenesis: the effect on differentiation in stem cells derived from bone marrow". *Osteoporos. Int.* 22: 675-684; Garcia-Martinez O, et al. (2014), "The effect of olive oil on osteoporosis prevention". *Int. J. Food Sci. Nutr*, Early Online: 1-7 DOI: 10.3109/09637486.2014.931361; Chin K Y and Ima-Nirwana S (2016). "Olives and Bones: A Green osteoporosis". *Int. J. Environ. Res. Public Health,* 13: 755.]

EGCG

Green tea (from *Camellia sinensis*) is one of the world's most popular beverages consumed at a high rate, especially in Asian countries including Korea, China, and Japan. A population-based, prospective cohort study has shown that green tea consumption is associated with reduced mortality due to all causes and cardiovascular disease as well, and randomized controlled trials have indicated that green tea is effective in decreasing blood pressure, low density lipoprotein cholesterol, oxidative stress, and chronic inflammation. Various studies have shown the beneficial effects of green tea, not only on cardiovascular diseases but also on obesity and T2DM. In a retrospective cohort study performed in Japan, a 33% risk reduction of developing T2DM was found in subjects consuming six or more cups of green tea daily compared to those consuming less than 1 cup per week. Another study reported that Taiwanese subjects who had habitually consumed tea for more than 10 years showed lower body fat composition and smaller waist circumference. Evidences from epidemiological studies thus suggest the possibility of green tea being a strategy for treatment or prevention of obesity and diabetes. [See e.g., Kuriyama S, et al. (2006), "Green tea consumption and mortality due to cardiovascular disease, cancer, and all causes in Japan: the Ohsaki study". *JAMA,* 296:1255-1265; Nantz M P, et al. "Standardized capsule of *Camellia sinensis* lowers cardiovascular risk factors in a randomized, double-blind, placebo-controlled study". *Nutrition,* 25:147-154; Iso H, et al. (2006), "JACC Study Group. The relationship between green tea and total caffeine intake and risk for self-reported type 2 diabetes among Japanese adults". *Ann. Intern. Med.* 144:554-562; Wu C H, et al. (2003), "Relationship among habitual tea consumption, percent body fat, and body fat distribution". *Obes. Res.* 11:1088-1095; Mackenzie T, et al. (2007), "The effect of an extract of green and black tea on glucose control in adults with type 2 diabetes mellitus: double-blind randomized study". *Metabolism*. 56:1340-1344; Nagao T, et al. (2009), "A catechin-rich beverage improves obesity and blood glucose control in patients with type 2 diabetes". *Obesity (Silver Spring)* 17:310-317; Hsu C H, et al. (2011), "Does supplementation with green tea extract improve insulin resistance in obese type 2 diabetics? A randomized, double-blind, and placebo-controlled clinical trial". *Altern. Med. Rev.* 16:157-163; Higdon J V and Frei B (2003), "Tea catechins and polyphenols: health effects, metabolism, and antioxidant functions". *Crit. Rev. Food Sci. Nutr.* 43:89-143; Furuyashiki T, et al. (2004), "Tea catechin suppresses adipocyte differentiation accompanied by down-regulation of PPARgamma2 and C/EBPalpha in 3T3-L1 cells". *Biosci. Biotechnol. Biochem.* 68: 2353-2359; Klaus S, et al. (2005), "Epigallocatechin gallate attenuates diet-induced obesity in mice by decreasing energy absorption and increasing fat oxidation". *Int. J. Obes. (London)* 29: 615-623; Kim H S, et al. (2014), "New insights into the mechanisms of polyphenols beyond antioxidant properties; lessons from the green tea polyphenol, epigallocatechin 3-gallates". *Redox Biology,* 2: 187-195; Wang S, et al. (2014), Ibid.; Babu P V, et al. (2013), "Recent Advances in Understanding the Anti-diabetic Actions of Dietary Flavonids" *J. Nutr. Biochem.* 24(11):1777-89; González-Castejón M, and Rodriguez-Casado (2011), Ibid.; Baboota R K, et al. (2013) Ibid.]

Green tea extract (GTE) has many naturally occurring biological components of which polyphenolic epicatechins (ECs) are predominantly active. These include (−)-epigallocatechin-3-gallate (EGCG), (−)-epigallocatechin (EGC), (−)-epicatechin-3-gallate (ECG), and (−)-EC. The EC and EGC are catechol catechins, EGC and EGCG are pyrogallol catechins, and ECG and EGCG are gallate catechins. The above cited studies revealed that EGCG, the most abundant form of catechin in green tea is the main attributable factor of its beneficial effects. EGCG has been shown to reduce blood glucose and improve glucose tolerance. These benefits are suggested to result from EGCG activities of (1) increasing expression of insulin receptor, insulin secretion, adiponectin and GLUT4, thereby increasing glucose uptake; (2) preventing oxidative distress and inflammation thereby protecting insulin producing β-cells from damage; and (3) inducing AMPK thereby inhibiting glucose absorption and gluconeogenesis.

The antiobesity benefits from EGCG result from (1) down regulating the expression of sterol regulatory element-binding protein (SREBP-1), thereby inhibiting FAS lipogenesis; (2) activating AMPK, adiponectin and sirtuin (SIRT1)

thereby promoting thermogenesis and lipolysis; (3) activating Wnt/b-catenin signaling in addition to AMPK and reducing expression of C/EBPα, PPAR-γ and SREBP-1 thereby suppressing adipocyte differentiation and proliferation; (3) Inducing pre-adipocyte apoptosis mediated by Cdk2 and caspase-3; and (4) reducing adipocyte derived inflammation that is associated with insulin resistance.

With regard to osteoporosis, epidemiological studies have found that consumption of green tea, a major source of EGCG, is associated with a lower risk of osteoporosis. Studies have also proved that EGCG and bone metabolism are closely linked. EGCG has been shown to induce the apoptosis of osteoclasts and inhibit the formation of osteoclasts by blocking the generation of NF-B and IL-1b, to reduce bone resorption by inhibiting osteoclast formation, and to promote the formation of mineralized bone nodules. The osteogenic effect of EGCG on human bone marrow-derived mesenchymal stem cells (hBMSCs) has also been studied and found to be a strong stimulatory effect on hBMSCs developing towards the osteogenic lineage, especially at a concentration of 5 µM. This effect is evidenced by an increased ALP activity and cell proliferation, the up-regulated expression of relevant osteogenic markers and the formation of bone-like nodules. EGCG directed osteogenic differentiation via the continuous up-regulation of Runx2. The underlying mechanism is believed to involve EGCG effects on the differentiation of hBMSCs into bone cells through the modulation of bone morphogenetic protein-2 (BMP-2) expression. EGCG has also been found to promote the proliferation of hBMSCs in a dose-dependent manner, thought to be associated with its anti-oxidative effect leading to favorable amounts of reactive oxygen species in the cellular environment. In summary, EGCG is a pro-osteogenic agent favoring bone formation over bone resorption. [See e.g., Chu C, et al. (2017), "Green Tea Extracts Epigallocatechin-3-gallate for Different Treatments." *BioMed. Research International*, Volume 2017, Article ID 5615647, 9 pp.; Nakagawa H., et al. (2002), "Fenton reaction is primarily involved in a mechanism of (−)-epigallocatechin-3-gallate to induce osteoclastic cell death." *Biochemical and Biophysical Research Communications,* 292(1): 94-101; Yun J-H, et al. (2004), "Inhibitory effects of green tea polyphenol (−)-epigallocatechin gallate on the expression of matrix metalloproteinase-9 and on the formation of osteoclasts." *Journal of Periodontal Research,* 3(5): 300-307; Val B, et al., (2007), "Epigallocatechin-3-gallate increases the formation of mineralized bone nodules by human osteoblast-like cells". *Journal of Nutritional Biochemistry,* 18(5): 341-347; Jin P, et al. (2014), "Epigallocatechin-3-gallate (EGCG) as a pro-osteogenic agent to enhance osteogenic differentiation of mesenchymal stem cells from human bone marrow: an in vitro study." *Cell and Tissue Research,* 356(2): 381-390.]

Procyanidins (Pcy)

Procyanidins are members of the proanthocyanidin (or condensed tannins) class of flavonoids. They are oligomeric compounds, formed from catechin and epicatechin molecules. They yield cyanidin when depolymerized under oxidative conditions. Procyanidins can be found in many plants, most notably apples, maritime pine bark, cinnamon, *aronia* fruit, cocoa beans, grape seed, grape skin, and açaí palm. Procyanidins have been shown to have antioxidant properties in vitro. Foods rich in procyanidins have high oxygen radical absorbance capacity, an in vitro measure of antioxidant effects. Types of procyanidins include dimers (e.g., Procyanidin A1 and Procyanidin B1, B2, B3, B4, B5, B6, B6), trimers [e.g., Procyanidin C1 (epicatechin-(4β→8)-epicatechin-(4β→8)-epicatechin)] and Procyanidin C2 (catechin-(4α→8)-catechin-(4α→8)-catechin)] and tetramers (e.g., Cinnamtannin A2). Procyanidin B1 for example is a procyanidin dimer with a 4→8 bond (epicatechin-(4β→8)-catechin). It can be found in *Cinnamomum verum* (Ceylon cinnamon, in the rind, bark or cortex), in *Uncaria guianensis* (root of cat's claw) and in *Vitis vinifera* (common grape vine, in the leaf) or in peach. Procyanidin B2 is another dimer with structure (−)-epicatechin-(4β→8)-(−)-epicatechin. Procyanidin B2 can be found in *Cinchona pubescens* (Chinchona, in the rind, bark and cortex), in *Cinnamomum verum* (Ceylon cinnamon, in the rind, bark and cortex), in *Crataegus monogyna* (Common hawthorn, in the flower and blossom), in *Uncaria guianensis*(Cat's claw, in the root), in (common grape vine, in the leaf), in *Litchi chinensis* (litchi, in the pericarp), and in the apple. In addition to its antioxidant property, Procyanidin B2 has been shown to inhibit the formation of advanced glycation end-products including pentosidine, carboxymethyllysine (CML), and methylglyoxal (MGO).

Pycnogenol™ is the trademarked name for a product derived from the pine bark of a tree known as *Pinus pinaster* standardized to contain 70% procyanidins. The active ingredients in pycnogenol can also be extracted from other sources, including peanut skin, grape seed, and witch hazel bark. Pycnogenol™ is marketed as a dietary supplement providing antioxidant and anti-inflammatory benefits.

Described below are other phytochemicals with activities against diabetes, obesity and associated conditions including inflammation and oxidative stress and thus may also be used in combination with one or more of the above preferred phytochemicals to treat osteoporosis, OA and RA.

Hesperidin

Hesperidin [hesperitin-7-O-rutinoside or hesperitin-7-O-rhamnosyl(1-6)glucoside] is a flavanone glycoside named after the term "Hesperidium", referring to citrus fruits which are the main source of hesperidin. Hesperidin and its aglycone (hesperitin) are common dietary flavonoids being found in many citrus products and are most well known for being concentrated in orange peels and pericarp. Hesperidin is widely known in traditional Chinese medicine alongside with naringenin as Chimpi, wherein the dried peels of citrus have been used medicinally. The actual active from hesperidin is its aglycone hesperitin (5,7,3'-trihydroxy-4'-methoxyflavanone); thus hesperidin acts like a hesperitin prodrug, i.e., supplies the body with hesperitin. After ingestion, hesperidin is hydrolyzed by gut microflora into aglycone form (hesperetin) and then conjugated mainly into glucuronides. Hesperetin and its metabolites have been reported to have several biological activities, including antioxidant, anti-inflammatory, lipid lowering, cardioprotective and neuroprotective effects; influencing bone strength and osteoblast differentiation; and ameliorating insulin resistance and endothelial dysfunction, among others. Synthetic variants of hesperidin that can be used to supply hesperitin to the body include hesperidin-7,3'-O-dimethylether (HDME), which is more lipid soluble than hesperidin and glucosyl-hesperidin (G-Hesperidin) where the aglycone (hesperitin) is not changed, but the diglycoside group has been modified into a triglycoside. This variant has increased water solubility approximately 10,000-fold relative to hesperidin but ultimately it releases hesperidin (glycone) in the body after being metabolized by intestinal α-glucosidases and then hesperidin can release free hesperitin. Another derivative that may be used to supply hesperidin in formulations is hesperidin methyl chalcone (HMC), which has been demonstrated to have high bioavailability. Most studies using hesperidin tend to use about 500 mg of supplemental hesperidin, and use the standard form of hesperidin if taking it as a daily preventative.

Hesperidin, as a bioflavonoid, provides antioxidant benefits via enhanced activity and production of cellular antioxidant enzymes such as superoxide dismutase (SOD), heme oxygenase-1 (HO-1), catalase, etc., and elevation of the predominant cellular antioxidant called glutathione [Roohbakhsh A, et al. (2015), "Molecular mechanisms behind the biological effects of hesperidin and hesperetin for the prevention of cancer and cardiovascular diseases". *Life Sci.* 124:64-74; Kalpana K B, et al. (2009), "Evaluation of antioxidant activity of hesperidin and its protective effect on H2O2 induced oxidative damage on pBR322 DNA and RBC cellular membrane". *Mol Cell Biochem.* 323(1-2): 21-9].

Oxidative stress in the body is often accompanied by systemic inflammation characteristic of many chronic conditions. Numerous studies indicate that hesperidin and hesperetin are able to reduce various pathologically elevated inflammatory markers. [See e.g., Agrawal Y O, et al. (2014), "Hesperidin produces cardioprotective activity via PPAR-γ pathway in ischemic heart disease model in diabetic rats", *PLOS One* https://doi.org/10.1371/journal.pone.0111212; Tamilselvam K, et al. (2013), "Antioxidant and anti-inflammatory potential of hesperidin against 1-methyl-4-phenyl-1,2,3, 6-tetrahydropyridine-induced experimental Parkinson's disease in mice", *Int. J. Nutr. Pharm. Neurol. Dis.* 3:294-302; Xiaoting L, et al. (2010), "Effect of hesperidin on expression of inducible nitric oxide synthase in cultured rabbit retinal pigment epithelial cells". *Adv. Exp. Med. Biol.* 664:193-201.] This inhibitory effect has been predominantly associated with their antioxidant activity and ability to inactivate the pro-inflammatory cascade initiated by free radicals. These compounds were also effective in decreasing the synthesis of pro-inflammatory cytokines e.g. tumor necrosis factor-alpha (TNF-α) as well as pro-inflammatory enzymes such as inducible nitric oxide synthase (iNOS), which yields nitric oxide (NO) and cyclooxygenase-2 (COX-2), which is involved in the production of inflammatory mediators such as prostaglandins.

Hesperidin is also well-known as a cardiovascular protective and strengthening agent. It demonstrates several benefits to the cardiovascular system due to its ability to affect various cellular mechanisms. For instance, due to its antioxidant properties hesperidin can prevent low density lipoprotein (LDL) oxidation and protect the cell membrane of erythrocytes (red blood cells) from oxidative damage. It also acts as an inhibitor of two main enzymes in cholesterol metabolism—HMGCoA reductase and ACAT that regulate total LDL (so called "bad" cholesterol") and "good cholesterol" (high density lipoprotein HDL) levels. While HMG-CoA reductase is a regulatory enzyme in cholesterol biosynthesis and a primary target for statin drugs (cholesterol lowering medication), ACAT catalyzes the intracellular esterification of cholesterol and is also engaged in cholesterol absorption, hepatic secretion of very low density lipoprotein (VLDL) and cholesterol accumulation in the vascular wall [Bok S H, et al. (1999), "Plasma and hepatic cholesterol and hepatic activities of 3-hydroxy-3-methyl-glutaryl-CoA reductase and acyl CoA: cholesterol transferase are lower in rats fed citrus peel extract or a mixture of citrus bioflavonoids". *J. Nutr.* 129(6): 1182-5]. Thus, by inhibiting the activity of these two enzymes hesperidin decreases the total "bad" cholesterol (LDL) and increases the "good" cholesterol (HDL). [See e.g., de Oliveira D M, et al. (2013), "Hesperidin associated with continuous and interval swimming improved biochemical and oxidative biomarkers in rats". *J. Int. Soc. Sports Nutr.* 10: 27.] A study on rats fed a high cholesterol diet supplemented with flavonoids (hesperidin and naringin) demonstrated inhibition of liver cholesterol biosynthesis (28.3%) and the esterification of hepatic cholesterol (23.7%) by hesperidin. In the same study tangerine peel extract was even more potent by decreasing liver cholesterol synthesis by 37% and its esterification by 32%. These results are in agreement with others, including a human study that demonstrated a marked decrease in triglyceride level after 4 weeks of hesperidin supplementation (using G-Hesperidin, 500 mg/day). [See e.g., Kim H K, et al. (2003), "Lipid-lowering efficacy of hesperetin metabolites in high-cholesterol fed rats". *Clin. Chim. Acta,* 327(1-2):129-37; Miwa Y, et al. (2005), "Glucosyl hesperidin lowers serum triglyceride level in hypertriglyceridemic subjects through the improvement of very low-density lipoprotein metabolic abnormality". *J. Nutr. Sci. Vitaminol.* (Tokyo) 51(6): 460-70.]

Another health benefit of hesperidin has been associated with its antihypertensive effect. It is believed that hesperidin is responsible for blood pressure lowering effect of orange juice since it promotes nitric oxide production resulting in vasodilation (widening of blood vessels). Moreover, hesperidin can enhance relaxation of the endothelial cells (cells of the inner blood vessel wall) induced by the neurotransmitter acetylcholine and can inhibit secretion of endothelium-derived vasoconstricting factor endothelin-1 (ET-1) [Morand C, et al. (2011), "Hesperidin contributes to the vascular protective effects of orange juice: a randomized crossover study in healthy volunteers". *Am. J. Clin. Nutr.* 93(1):73-80]. All aforementioned mechanisms aid in blood pressure normalization.

In addition to reducing inflammation and oxidative stress, hesperidin actions relevant to treatment of T2DM include (1) inducing the expression of adiponectin and (2) upregulating activity of hepatic glucokinase, PPAR-Y and adipocyte GLUT4 resulting in lower blood glucose and HBA1c. [See e.g., Akiyama S, et al. (2010), "Dietary Hesperidin Exerts Hypoglycemic and Hypolipidemic Effects in Streptozotocin-Induced Marginal Type 1 Diabetic Rats". *J. Clin. Biochem. Nutr.* 46, 87-92; Vinayagam R and Xu B (2015). Ibid.]

Magnolol and Honokiol

Magnolol is an active component isolated from *Magnolia officinalis* (*Magnolia* bark), typically along with its structural isomer, honokiol and also 4-O-methylhonokiol. Both are di-allyl biphenyl diols. The bark is stripped from the stems, branches, and roots of *Magnolia* tree, and the polyphenolic components containing magnolol and honokiol are extracted. *Magnolia officinalis* is widely used in traditional Chinese medicine to facilitate bowel movement and ameliorate abdominal fullness. In past decades, magnolol/honokiol have been characterized as anti-oxidant, anti-depressant, anti-allergic, anti-cancer and anti-microbial agents. The potent antioxidant activities of magnolol and honokiol are thought to be the contribution of hydroxyl and allylic groups on a biphenolic moiety. The hydroxyl group on the biphenolic moiety results in magnolol/honokiol activity against reactive oxygen species, inhibiting cell proliferation and antimicrobial activity. Similar to quercetin, magnolol and honokiol have been demonstrated to have significant antimicrobial activity, for example, against periodontopathic microorganisms such as *Porphyromonas gingivalis, Prevotella gingivalis,* and *Actinobacillus actinomycetemcomitans* and a relatively low cytotoxic effect on human gingival cells, suggesting potential therapeutic use as a safe oral antiseptic for the prevention and the treatment of periodontal disease. [Chang B S, et al. (1998), "Antimicrobial Activity of Magnolol and Honokiol against Periodontopathic Microorganisms". *Planta Medica* 64: 367.]

A series of positive effects on the cardiovascular (CV) system have also been demonstrated for magnolol/honokiol. These effects are mostly attributed to their antioxidant activity. Excessive free radicals induce lipid peroxidation, protein denaturation and DNA damage triggering cell death. In the past 20 years, magnolol has been found to have diverse functions in different cells of the CV system. The cardiovascular protective activities of magnolol are reported to result from attenuating ischemic/reperfusion heart injury, reducing atherosclerotic change and endothelial cell apoptosis, inhibiting neutrophil activation/adhesion and vascular smooth muscle cell proliferation, preventing platelet aggregation and thrombosis, and promoting vessel relaxations. Such cardiovascular protection effects regulated by magnolol are cell-type specific and dose-related. [See e.g., Ho J H-C and Hong, C-Y (2012), "Cardiovascular protection of magnolol: cell-type specificity and dose-related effects". *Journal of Biomedical Science* 19:70.]

Safety testing of magnolol or extracts of *Magnolia* bark has been reported. In a preclinical study, oral administration in animals (mice: 0.625-2.5 g/kg; rat: 0.06-0.48 g/kg/day for 21 days or 0.06-0.24 g/kg/day for 90 days) of ethanol extracts (94% magnolol and 1.5% honokiol) of *Magnolia* bark neither induced drug-related side effects nor altered immune response. A randomized, double-blind, placebo-controlled clinical study for weight control among female adults showed that oral administration of capsuled extracts of *Magnolia officinalis* and *Phellodendron amurense* (250 mg, three times a day for 6 weeks) was well tolerated in both healthy and obese patients, and regulation of cortisol only in obese patients was a benefit for weight control. The oral bioavailability of magnolol is reportedly about 4-5%. To reach the therapeutic level through oral administration with 5% of oral bioavailability, 2 mg/kg per day, i.e. daily 120 mg of magnolol for a 60-kg adult, is considered sufficient for cardiovascular protection, and such a dosage is applicable and safe based on the safety studies cited above.

With regard to diabetes and obesity, the benefit from magnolol results in part from its being a strong agonist of peroxisome proliferator activated receptor gamma (PPAR-γ). Magnolol functions as a PPAR-γ agonist through direct binding to the PPAR-γ ligand binding domain. As discussed above, PPAR-γ agonists such as the drugs troglitazone and rosiglitazone are used to treat diabetes. Magnolol/honokiol (MG/HK) are believed to have the same effect. In addition, the strong antioxidant activity of MG/HK (1000 times more potent than vitamin E) prevents lipid peroxidation and the generation of reactive oxygen species (ROS), which are factors in the development of obesity and T2DM. It has been reported that MG reduced fasting blood glucose and plasma insulin levels in type 2 diabetic rats and increased the glucose uptake in 3T3-L1 adipocytes. In addition, both HK and MG stimulated glucose uptake in insulin-sensitive and insulin-resistant murine and human adipocytes via an insulin signaling pathway and protected tissues and cells against a variety of oxidative stressors. It was also reported that 4-O-methylhonokiol (MH), another major bio-active component of *Magnolia* extracts, had anti-inflammatory properties via inhibition of NF-κB pathway in macrophage raw 264.7 cells. In a study of lipid and glucose metabolism in high fat diet-induced obese mice, it was reported that magnolol and honokiol individually and in combination significantly reduced plasma total cholesterol and glucose levels, and improved glucose tolerance, compared with controls. Both also increased expression of the glucose transporter GLUT4 and adiponectin genes in white adipose tissue. Honokiol and magnolol improved hyperglycemia and dyslipidemia and act synergistically when used in combination. [See e.g., Lee J, et al. (2005), "Anti-inflammatory effects of magnolol and honokiol are mediated through inhibition of the downstream pathway of MEKK-1 in NF-κB activation signaling". *Planta Medica* 71(4):338-343; Chiang J, et al. (2009) "Honokiol protects rats against eccentric exercise-induced skeletal muscle damage by inhibiting NF-κB induced oxidative stress and inflammation". *European Journal of Pharmacology.* 610(1-3):119-127; Alonso-Castro A J, et al. (2011), "*Magnolia dealbata* Zucc and its active principles honokiol and magnolol stimulate glucose uptake in murine and human adipocytes using the insulin-signaling pathway". *Phytomedicine.* 18(11):926-933; Choi S-S, et al. (2009), "Magnolol enhances adipocyte differentiation and glucose uptake in 3T3-L1 cells". *Life Sciences.* 84(25-26):908-914; Wang L, et al. (2014), "Natural product agonists of Peroxisome proliferator-activated receptor gamma (PPARγ): a review". *Biochemical Pharmacology* 92:73-89; Lee Y-S et al. (2015), "Honokiol, magnolol, and a combination of both compounds improve glucose metabolism in high-fat diet-induced obese mice". *Food Science and Biotechnology.* 24(4): 1467-1474.]

Berberine

Berberine (5,6-dihydro-9,10-dimethoxybenzo[g]-1,3-benzodioxolo [5,6-a]quinolizinium) is found in a handful of plants widely used in botanical medical practice including Goldenseal (*Hydrastis canadensis*), Oregon grape (*Berberis aquifolium*), Barberry (*Berberis vulgaris*), and Chinese Goldthread (*Coptis chinensis*). Two other berberine-containing plants that are familiar to practitioners of Chinese medicine are *Phellodendron chinense* and *Phellodendron amurense*. Berberine is usually prepared from these sources. Berberine is yellow in color, and plants containing berberine often have been used as a dye, particularly for coloring wool. Chemically, berberine is classified as an isoquinoline alkaloid. Among the most common chemical forms of berberine are the hydrochloride, sulfate, citrate and phosphate salts.

The traditional therapeutic use of berberine was as anti-infection or anti-inflammation agent. In China, berberine is an over-the-counter drug for the treatment of bacterial diarrhea. In the late 1980s the hypoglycemic effect of berberine was firstly reported when berberine was prescribed to treat diarrhea in diabetic patients and since then, berberine has been used as an anti-diabetic agent in Chinese folk medicine. Newly published research reports in the last 20 years reveal that berberine may have clinical applications in a range of conditions including metabolic syndrome, inflammation, and cancer. Metabolic syndrome includes hyperglycemia, diabetes, lipid abnormalities, energy imbalances and obesity.

The fundamental mechanism of action underlying berberine's impact on human health is most probably its action on the adenosine monophosphate-activated protein kinase or AMP-activated protein kinase (AMPK). This enzyme acts as a central energy regulatory control switch regulating how energy is produced and used in the body. AMPK induces a cascade of events within cells that are all involved in maintaining energy homeostasis. The AMPK system senses and responds to changes in energy metabolism both on the cellular and the whole-body level. It is via AMPK that low energy status switches cellular metabolism from ATP-consuming anabolic pathways to ATP-producing catabolic pathways. AMPK regulates an array of biological activities that normalize lipid, glucose, and energy imbalances. Metabolic syndrome occurs when these AMPK-regulated pathways are turned off, triggering the above diseases.

AMPK activation was cited early on as an explanation of berberine's ability to improve glucose control in diabetic animals. Berberine increases glucose uptake by muscle fibers independent of insulin levels. Berberine triggers AMPK activation and increases glycolysis, leading to decreased insulin resistance and decreased oxygen respiration. The same mechanism leads to a reduction in gluconeogenesis in the liver. In addition to its activity to activate AMPK, berberine also inhibits α-glucosidase, maltase and sucrase activities; reduces the expression of a number of adipocyte-specific genes including FAS, SREBP-1 and PPAR-γ; and reduces oxidative stress and down-regulates pro-inflammatory responses, all resulting in reduced blood glucose and hemoglobinA1c (HbA1c) levels and increased insulin sensitivity. The same activities and mechanisms reportedly underlie berberine's antiobesity effects and favorable influence on weight loss, i.e., inhibiting adipogenesis and lipogenesis while promoting lipolysis and thermogenesis in adipose tissues and muscle. [See e.g., Lee Y S, et al. (2006). "Berberine, a Natural Plant Product, Activates AMP-Activated Protein Kinase With Beneficial Metabolic Effects in Diabetic and Insulin-Resistant States". *Diabetes*, 55: 2256-2264; Yin J, et al. (2012). "Effects and mechanisms of berberine in diabetes treatment". *Acta Pharmaceutica Sinica B*, 2: 327-334; Wu Y, et al. (2015), "Protective effects of berberine on high fat-induced kidney damage by increasing serum adiponectin and promoting insulin sensitivity". *Int. J. Clin. Exp. Pathol.* 8(11):14486-14492; Yin J, et al. (2008), "Efficacy of Berberine in Patients with Type 2 Diabetes". *Metabolism*, 57: 712-717.]

*Salacia*

The *Salacia* genus consist of about 120 species (e.g., *Salacia reticulata, Salacia* oblonga, *Salacia chinensis, Salacia prinoides*), which are widely distributed in Sri Lanka, India, China, Vietnam, Indonesia and other Asian countries. *Salacia reticulata* (SR), known as Kothala himbutu in Sinhalese is widely distributed in Sri Lanka and southern India. It is a large woody climber and its root and stem has been extensively used in Ayurvedic medicine for the treatment of diabetes. It is also believed to contain anti-rheumatic properties and is also used for many skin related ailments in traditional healing practices. *Salacia* species have been studied widely for its presumed hypoglycemic and anti-obesity effects in animal models and humans. Multiple compounds with hypoglycemic effects have been isolated from *Salacia* species. Many triterpenes, hydrocarbons and sitosterol have been isolated from roots and stem barks. The root of several species has been reported to contain mangiferin, kotalanol, and salacinol. Mangiferin is a flavonoid with polyphenolic groups and a glycosidic group. Kotalanol, and salacinol have a polyhydroxy sulfonium sulfate structure. These 3 compounds are believed to be the main bio-actives credited for the actions of *Salacia* species. Beyond that, *Salacia* appears to have a fairly unique polyphenolic profile. [See e.g., Li Y, et al. (2008), "*Salacia* root, a unique Ayurvedic medicine, meets multiple targets in diabetes and obesity". *Life Sci.* 82(21-22):1045-9; Matsuda H Y M, et al. (2005), "Antidiabetogenic constituents from *Salacia* species". *J. Trad. Med.* 22(1):145-53; Yoshikawa M M T, et al. (1998), "Kotalanol a potent alpha glucosidase inhibitor with thiosugar sulfonium sulphate structure from antidiabetic Ayurvedic medicine *Salacia reticulata*". *Chem. Pharm. Bull.* 46(8):1339-40; Yoshikawa M N N, et al. (2001), "Polyphenol constituents from *Salacia* species: quantitative analysis of mangiferin with alpha glucosidase and aldose reductase inhibitory activities". *Yakugaku Zasshi*. 121:5371-8; Medagama A B (2015), "*Salacia reticulata* (Kothala himbutu) revisited; a missed opportunity to treat diabetes and obesity?". *Nutrition Journal* 14:21.]

The evidence available from in vitro, animal and human studies point towards effective reduction of plasma glucose and body weight in subjects treated with *Salacia* extracts. In vitro studies demonstrated the ability of *Salacia* to inhibit intestinal alpha glucosidase. In mouse mesenteric fat, *Salacia* enhances the mRNA expression of hormone sensitive lipase (HSL) and adiponectin; thus increasing lipolysis and reducing insulin resistance respectively. In 3T3-L-1 adipocytes, lipogenesis factors are down regulated and lipolysis factors are up regulated with *Salacia* treatment. Animal studies and clinical trials are consistent in demonstrating improvement of glucose concentrations in the fasted and sugar-loaded states. Clinically significant reductions of HbA1C and plasma insulin are reported with treatment of 6 weeks to 3 months. One clinical trial reported significant reduction of body weight and BMI when *Salacia* is used in combination with vitamin D.

*Acacia* Polyphenols (AP)

The *Acacia* genus of evergreen tree (e.g., *A. mearnsii* or black wattle, *A. catechu, A. mollissima*, and *A. milanoxylon*) is common in Australia, Tasmania, South Africa, eastern Africa and South America. The aqueous extracts of the bark of *A. mearnsii* contain significant amounts of polyphenols, referred to as *Acacia* polyphenols (AP), whose major components are unique flavan-3-ol oligomers and polymers consisting of 4 or 5 monomeric units, including robinetinidol, fisetinidol, catechin and gallocatechin. *Acacia* extract has long been used as an astringent and antibacterial to treat stomatitis and diarrhea in Asian countries.

Other therapeutic effects of AP include anti-diabetic and anti-obesity. Early studies have reported that the powdered seeds of *Acacia* exhibit hypoglycemic actions by increasing insulin secretion in non-diabetic rats and rabbits. In more recent animal studies it was reported that oral doses of an AP preparation significantly inhibited fat accumulation and body weight gain and reduced hyperglycemia and insulin resistance in KKAy mice, model animals for obesity and type 2 diabetes. The AP preparation used in this study was an extract of South African *A. mollissima*, which contains ~80% (w/v) polyphenols with molecular weights ranging from 300 to 3,000 kDa, robinetinidol and fisetinidol being the major content. The parameters that were observed to explain the anti-obesity and anti-diabetic effects of AP include (1) increased mRNA and protein expressions of energy expenditure-related genes in skeletal muscle and liver, thereby increasing energy expenditure; (2) decreased mRNA expression of (a) acetyl-CoA carboxylase (ACC) and fatty acid synthase (FAS), the rate-limiting enzymes of fatty acid synthesis in the liver; (b) SREBP-1c, which controls the expression of these enzymes and (c) PPAR-γ and lipoprotein lipase (LPL), fat intake-related genes, which control fat intake by the liver; (3) increased mRNA expression of adiponectin and decreased mRNA expression of TNF-α in white adipose tissue, thereby inhibiting insulin resistance; and (4) increased mRNA expression of GLUT4 in skeletal muscle, thereby reducing insulin resistance. AP thus reduces hyperglycemia and hyperinsulinemia, not simply through alleviated obesity, but through increased adiponectin secretion and suppressed TNF-α secretion in white adipose tissue, and increased GLUT4 expression in skeletal muscle.

In human clinical trials, the safety and effects of short-term intake of an AP supplement on glucose and insulin responses to an oral glucose tolerance test (OGTT) in otherwise healthy subjects with IGT (impaired glucose tolerance) were evaluated. The AP product used was a tablet-form AP preparation, which contains ~80% (w/v) polyphenols, available commercially as a supplementary diet product in Japan. This trial demonstrated that AP supplement intake for up to 8 weeks significantly reduced (improved) overall glucose and insulin responses to an oral glucose load in the OGTT, indicating a beneficial effect of the AP supplement on glucose homeostasis. Throughout the 8-week intervention period, no AP supplement-related adverse events were reported. The safety of the AP supplement is supported by a previous study demonstrating that a 4-week intake of the AP supplement in daily doses ≤1,000 mg AP was safe in healthy male adults. [See e.g., Ikarashi N, et al. (2011), "Anti-obesity and anti-diabetic effects of *acacia* polyphenol in obese diabetic KKAy mice fed high-fat diet". *Evid. Based Complement. Alternat. Med.* 2011: 952031; Ikarashi N, et al. (2011), "The inhibition of lipase and glucosidase activities by *acacia* polyphenol". *Evid. Based Complement. Alternat. Med.* 2011:272075; Kataoka T, et al. (2011), "Safety of *acacia* polyphenol dietary supplement: safety evaluation studies in healthy male adults". *Pharmacometrics.* 80:43-52; Ogawa S, et al. (2013), "Effect of *acacia* polyphenol on glucose homeostasis in subjects with impaired glucose tolerance: A randomized multicenter feeding trial". *Exp. Ther. Med.* 5(6): 1566-1572; Singh K N, et al. (1976), "Hypoglycaemic activity of *Acacia catechu, Acacia suma*, and *Albizzia odoratissima* seed diets in normal albino rats". *Indian Journal of Medical Research,* 64(5): 754-757; Wadood A, et al. (1989), "Effects of *Acacia arabica* and *Caralluma edulis* on blood glucose levels of normal and alloxan diabetic rabbits". *Journal Pakistan Medical Assoc.* 39(8):208-212.]

PPAR-γ Modulators

As indicated above, substances that act as ligands of PPAR-γ are useful in the present compositions. Examples include plant lipids such as n-3 and n-6 fatty acids and their derivatives, isoflavones and flavonoids. Dietary lipids include cis-5,8,11,14,17-eicosapentaenoic acid (EPA); cis-4,7,10,13,16,19-docosahexaenoic acid (DHA) and oxidized derivatives such as 4-hydroxy docosahexaenoic acid (4-HDHA) and 4-oxo docosahexaenoic acid (4-oxoDHA); linoleic acid; and eicosadienoic acid. Isoflavones include daidzein, genistein, and glycitein. Flavonoids and other polyphenols that have PPAR-γ modulating activity include quercetin, psi-baptigenin, hesperidin, hesperitin, magnolol, honokiol, EGCG, baicalein and its glucoside baicalin, Cinnamtannin B1 (in cinnamon) and rosmarinic acid (in marjoram). By PPAR-γ modulating activity is meant that the agents herein may function either as activator (up-regulator) or suppressor (down-regulator) of PPAR-γ. Human PPARs including PPAR-γ are expressed in several metabolically active tissues including liver, kidney, spleen, heart, skeletal muscle, large intestine and white and brown fat and are present in many cell types including monocytic, vascular endothelial, and vascular smooth muscle cells. Mediation of metabolic and cellular processes is very complex and depends on the particular tissue(s), cellular condition(s) and stimulated signaling pathway(s) being affected. Thus, in some instances, up-regulation of PPAR-γ activity is beneficial and suppression is beneficial in other instances.

Other Bio-Actives—Vitamins and Minerals

The present compositions may optionally include (a) vitamins including vitamins A, E, D, C, B2, B1, niacin B12, K (K1, K2) and folic acid and (b) minerals such as Mg, Ca, Zn, Fe, iodine. Magnesium and vitamins C, D and K are preferred components herein.

Magnesium

Magnesium is an essential mineral for the human body. It is involved in many biological reactions in the body, including glucose use, fat synthesis, muscle contraction and in the production and transport of energy and proteins. A diet rich in green, leafy vegetables, legumes, nuts, whole grains and fish is normally sufficient to meet the daily magnesium requirement. However, many people take less than the recommended dietary allowance. Low magnesium levels are often seen with malnutrition, or with the use of diuretic medicines, which can cause excessive losses of magnesium. Low Mg levels have been linked to diseases such as osteoporosis, high blood pressure, clogged arteries, heart disease, diabetes and stroke and magnesium supplements have been administered for these conditions. It has also been reported that increased consumption of magnesium is associated with reduced mortality in adults at high cardiovascular risk. [See e.g., Guasch-Ferre, M, et al (2014), "Dietary Magnesium Intake Is Inversely Associated with Mortality in Adults at High Cardiovascular Risk". *J. Nutr.* 144(1): 55-60.] The major side effect of magnesium is diarrhea, which is more common the higher the dose.

Dosing depends on the indication for which magnesium is being used. It also depends on the type of magnesium compound used, such as the chloride, sulfate, carbonate, oxide, citrate, malate, aspartate, glutamate, taurate and bisglycinate, to name a few. Preferred for use herein include the organic salts and complexes, e.g., citrate and malate and the amino acid chelated Mg complexes, such as magnesium bisglycinate, which is a soluble organic complex of Mg with the amino acid glycine. Amino acid chelated magnesium is highly bioavailable and has no gastrointestinal side effects such as diarrhea. The reported RDA for Mg is 300-400 mg/kg/day, except for people with impaired kidney function. Overall, the risk of magnesium intake at prescribed levels to healthy people is very low. The glycinate salt is readily soluble and allows for a safe level of total salt and glycine to be introduced by this complex.

Importantly, magnesium has been shown to provide benefits against vascular calcification (VC), which is a condition associated with diabetes as a trigger. [See related U.S. Pat. No. 1,564,084 filed on Jul. 13, 2017.]

Both obesity and T2DM are associated with magnesium (Mg) deficits. A chronic latent Mg deficit or an overt clinical hypomagnesemia is common in patients with type 2 diabetes, especially in those with poorly controlled glycemic profiles. Low dietary Mg intake has also been related to the development of type 2 diabetes and metabolic syndrome. The body requires magnesium to absorb and utilize nutrients. Without magnesium the body cannot properly use the fats, proteins and carbohydrates consumed every day. Magnesium is a co-factor of many enzymes involved in glucose metabolism and has an important role in insulin action. Insulin stimulates magnesium uptake in insulin-sensitive tissues. Magnesium is required for both proper glucose utilization and insulin signaling. Metabolic alterations in cellular magnesium, which may play the role of a second messenger for insulin action, contribute to insulin resistance. Conditions like insulin resistance and diabetes are strongly associated with obesity, so controlling blood sugar levels is a key factor in maintaining a healthy weight. When enough magnesium is present in the body, insulin can function properly and blood glucose is used for energy. Magnesium deficiency causes insulin to function poorly, resulting in high blood sugar and fat storage. Thus magnesium supplementation is beneficial toward control and/or prevention of both T2DM and obesity. Studies have shown that indeed magnesium increases insulin sensitivity and also reduces inflammation and oxidative stress. These actions of magnesium contribute to reducing blood glucose and hemoglobinA1c (HbA1c) levels. [See e.g., Balon T W, et al. (1995). "Magnesium supplementation reduces development of diabetes in a rat model of spontaneous NIDDM. *Am. J. Physiol.* 269: E745-52; Barbagallo M and Dominguez L (2015). "Magnesium and Type 2 Diabetes". *World J. Diabetes.* 6: 1152-1157; Dong J Y (2011). "Magnesium Intake and Risk of Type 2 Diabetes". *Diabetes Care,* 34: 2116-2122; Dong J Y and Qin L Q. (2012), "Dietary calcium intake and risk of type 2 diabetes: possible confounding by magnesium. *Eur. J. Clin. Nutr.* 66: 408-410.]

Additionally magnesium deficiency, through exacerbating chronic inflammatory stress, is believed to play a role in the onset of chronic diseases including osteoporosis, OA and RA. Several direct and indirect mechanisms contribute to the effects of low Mg on bone density. Studies of Mg deficient animals show that not only severe but also moderate dietary restriction of Mg results in qualitative changes in bone (i.e., reduced Mg concentration) as well as in aberrant bone turnover in young growing rats (i.e., severely depressed rates of bone formation and bone resorption), which may impair bone development and bone strength. Low Mg intake has also been found to retard cartilage and bone differentiation as well as matrix calcification. In experimental Mg deficiency in rodents, decreased bone formation is partly due to reduced osteoblastic activity. Thus, the number of osteoblasts detected by histomorphometry is reduced and the levels of two markers of osteoblastic function, namely alkaline phosphatase and osteocalcin, are decreased. Moreover, an increase in the number of osteoclasts has been described. Low extracellular Mg inhibits osteoblast growth by increasing the release of nitric oxide through the upregulation of inducible nitric oxide synthase, while it increases the number of osteoclasts generated from bone marrow precursors.

Apart from direct effects on the structure and the cells of bone, Mg deficiency also impacts on the bone indirectly by affecting the homeostasis of the two master regulators of calcium homeostasis, i.e., parathyroid hormone (PTH) and $1,25(OH)_2$-vitamin D thus leading to hypocalcemia. In most species, hypomagnesemia impairs secretion of PTH and renders target organs refractory to PTH. Reduced secretion of PTH or impaired peripheral response to the hormone lead to low serum concentrations of $1,25(OH)_2$-vitamin D. Hypomagnesemia also promotes inflammation and a relation exists between inflammation and bone loss. In Mg deficient rodents, TNFα, IL-1 s and IL-6 are increased both in serum and in the bone marrow microenvironment. These cytokines not only amplify osteoclast while inhibiting osteoblast function but also perpetuate inflammation. In addition to enhancing pro-inflammatory cytokine secretion, substance P is released on nerve ending in bone at high levels in Mg deficiency and this stimulates the activity of osteoclasts. Mg deficiency also promotes oxidative stress, partly as a consequence of inflammation and partly because of the reduced anti-oxidant defenses which occur upon Mg restriction. The increased amounts of free radicals further potentiate the activity of osteoclasts and depress that of osteoblasts. Overall, all experimental data from animal studies indicate that reduced dietary intake of Mg is a risk factor for osteoporosis through many different mechanisms. The mechanisms explaining the effects of Mg deficiency on the bone in humans are similar to what has been described in experimental animal models. These beneficial activities of magnesium against osteoporosis include (a) increasing osteoblast differentiation by inducing Runx2 expression and activity; (b) inhibiting osteoclast differentiation by inhibiting RANKL, pro-inflammatory cytokines such as TNF-α and IL-6; and (c) promoting secretion of parathyroid hormone (PTH).

[See e.g., Nielsen F H, (2010), "Magnesium, inflammation, and obesity in chronic disease". *Nutr. Rev.;* 68:333-40; Stendig-Lindberg G, Tepper R, Leichter I. (1993). "Trabecular bone density in a two year controlled trial of peroral Magnesium in osteoporosis". *Magnesium research: official organ of the International Society for the Development of Research on Magnesium.* 6(2):155-63; Carpenter To, et al. (2006), "A randomized controlled study of effects of dietary magnesium oxide supplementation on bone mineral content in healthy girls". *J. Clin. Endocrinol. Metab.* 91: 4866-4872; Cheng M, et al. (2016), "A novel open-porous magnesium scaffold with controllable microstructures and properties for bone regeneration" *Scientific Reports.* 6:24134; Roy M and Bose S (2012), "Osteoclastogenesis and Osteoclastic Resorption of Tricalcium Phosphate: Effect of Strontium and Magnesium Doping". *J. Biomed. Mater. Res. A.* 100: 2450-2461; Castigglioni S, et al. (2013), "Magnesium and Osteoporosis: Current State of Knowledge and Future Research Directions". *Nutrients,* 5: 3022-3033; Rude R K, et al. (2009), "Skeletal and hormonal effects of magnesium deficiency. *J. Am. Coll. Nutr.* 28:131-141; Creedon A, et al. (1999), "The effect of moderately and severely restricted dietary magnesium in takes on bone composition and bone metabolism in the rat". *Br. J. Nutr.* 82:63-71; Schwartz R and Reddi A H. (1979), "Influence of magnesium depletion on matrix-induced endochondral bone formation". *Calcif. Tissue Int.* 29:15-20; Rude R K, et al. (2004), "Magnesium deficiency and osteoporosis: Animal and human observations". *J. Nutr. Biochem.* 15:710-716; Rude R K, et al. (1999), "Magnesium deficiency-induced osteoporosis in the rat: Uncoupling of bone formation and bone resorption". *Magnesium Res.* 12:257-267; Rude R K, et al. (2003), "Magnesium deficiency: Effect on bone and mineral metabolism in the mouse". *Calcif. Tissue Int.* 72:32-41; Leidi M, et al. (2012), "Nitric oxide mediates low magnesium inhibition of osteoblast-like cell proliferation". *J. Nutr. Biochem.* 23:1224-1229; Belluci M M, et al. (2013), "Magnesium deficiency results in an increased formation of osteoclasts". *J. Nutr. Biochem.* doi: 10.1016/j.jnutbio.2012.12.008; Pironi L, et al. (2009), "The complex relationship between magnesium and serum parathyroid hormone: A study in patients with chronic intestinal failure. *Magnesium Res.* 22:37-43; Mazur A, et al. (2007), "Magnesium and the inflammatory response: Potential physiopathological implications". *Arch. Biochem. Biophys.* 458: 48-56; Baker-LePain J C, et al. (2011) "Effects of inflammation on bone: An update". *Curr. Opin. Rheumatol.* 23:389-395; Wolf F I, et al. (2009), "Magnesium deficiency affects mammary epithelial cell proliferation: Involvement of oxidative stress". *Nutr. Cancer.* 61:131-136; Garrett I R, et al. (1990), "Oxygen-derived free radicals stimulate osteoclastic bone resorption in rodent bone in vitro and in vivo". *J. Clin. Investig.* 85:632-639.]

Vitamin D

Vitamin D refers to a group of fat-soluble sterols that are functional in humans for increasing intestinal absorption of calcium, iron, magnesium, phosphate, and zinc. The two major forms in this group are vitamin D3 (also known as cholecalciferol) and vitamin D2 (ergocalciferol), and vitamin $D_3$ or cholecalciferol; vitamin D without a subscript refers to either D2 or D3 or both. These are known collectively as calciferol. Cholecalciferol and ergocalciferol can be ingested from the diet and from supplements. However, very few foods contain vitamin D. Synthesis of vitamin D (specifically cholecalciferol) from 7-dehydrocholesterol in the skin of humans and most vertebrate animals by sunlight/ UVB radiation exposure is the major natural source of the vitamin. Vitamin D from the diet or dermal synthesis from sunlight is biologically inactive; activation requires enzymatic conversion (hydroxylation) in the liver and kidney. In the liver, cholecalciferol (vitamin D3) is converted to calcidiol (aka 25-hydroxycholecalciferol or 25-hydroxyvitamin D3); ergocalciferol (vitamin D2) is converted to 25-hydroxyergocalciferol (aka 25-hydroxyvitamin D2). Part of the calcidiol from vitamin D3 is converted by the kidneys to calcitriol, the biologically active form of vitamin D. Calcitriol circulates as a hormone in the blood and functions e.g., to regulate the concentration of calcium and phosphate in the bloodstream and to promote the healthy growth and remodeling of bone. Calcitriol also affects neuromuscular and immune function. Most people are not deficient in vitamin D, but neither do they have an optimal level of vitamin D. Due to the many health benefits of vitamin D, supplementation is encouraged if optimal levels are not present in the body. The recommended daily allowance for Vitamin D is currently set at 400-800 IU/day, but this is too low for adults with deficiency. The safe upper limit in the United States and Canada is 4,000 IU/day. Research suggests that the true safe upper limit is 10,000 IU/day. For moderate supplementation, a 1,000-2,000 IU dose of vitamin D3 is sufficient to meet the needs of most of the population. This is the lowest effective dose range. Higher doses, based on body weight, are in the range of 20-80 IU/kg daily.

Vitamin D and calcium have long been recognized as important and required nutrients for bone health and maintenance. Optimal bone health requires both a high dietary calcium intake and high vitamin D intake to ensure proper levels of these essential nutrients in the body. Calcium is necessary to many cell functions. Calcium is not only important to bone health, but it is also essential for neuromuscular activity, blood coagulation, and normal cardiac function. It is a vital component of bone architecture and is required for deposition of bone mineral throughout life. Although the body stores more than 99% of its calcium in the bones and teeth, it is also found in the extracellular fluid (ECF) or plasma. The levels of plasma calcium dictate calcium balance. If the plasma level decreases, bone resorption increases to restore plasma levels. Adequate intake of calcium is necessary to maintain this balance. Calcium is absorbed in the small intestines with the aid of vitamin D. Vitamin D is thus an equally important nutrient in the maintenance of bone health. The primary functions of vitamin D are the regulation of intestinal calcium absorption and the stimulation of bone resorption leading to the maintenance of serum calcium concentration. In vitamin D deficiency states, decreased calcium absorption occurs from the intestines, causing increased osteoclast production, which enhances the mobilization of calcium from the bone. During periods of decreased dietary intake, 1,25(OH)2 Vitamin D interacts with receptors in osteoblasts, ultimately leading to increased formation of osteoclasts The mature osteoclast then releases enzymes to breakdown bone matrix ultimately releasing calcium and other minerals into the circulation. If the serum free calcium level remains low, the parathyroid gland is stimulated. Release of parathyroid hormone (PTH) causes increased renal reabsorption of calcium and also stimulates osteoclast production, leading to increased serum levels of calcium. If vitamin D deficiency is not corrected, calcium continues to be pulled from the bone resulting in increased risk of rickets in children and of bone thinning, compromised bone strength, and osteoporosis in adults. Reasons for an increased risk of fracture associated with vitamin D deficiency are numerous. Inability to absorb adequate amounts of calcium for optimal bone health, as well as an increased susceptibility of falling, impaired muscle strength, and increased rates of bone loss can increase the risk of fracture It has been reported that lower levels of vitamin D are independently associated with an increased risk of falling particularly in the elderly. In fact, supplementation with vitamin D has been shown to improve musculoskeletal function and reduce the risk of falling in elderly women. Human muscle contains vitamin D receptors that may lead to increasing muscle strength and improving stability The combination of 700 units/day of vitamin D and 500 mg of calcium (obtained through supplementation in addition to diet) was shown to reduce falls by as much as 65% over three years in less active women over the age of 65. [See e.g., Sunyecz J A, (2008), "The use of calcium and vitamin D in the management of osteoporosis." *Ther. Clin. Risk Manag.* 4(4): 827-836; Bringhurst F R, et al. (2005), "Bone and mineral metabolism in health and disease." *Harrison's Principles of Internal Medicine.* 16th ed. II. New York: pp. 2246-9; Holick M F. (2004), "Sunlight and vitamin D for bone health and prevention of autoimmune diseases, cancers and cardiovascular disease". *Am. J. Clin. Nutr.* 80(Suppl):1678S-88S; Holick M F (2005), "Vitamin D: important for prevention of osteoporosis, cardiovascular heart disease, type 1 diabetes, autoimmune diseases, and some cancers". *South Med. J.* 98:1024-7; Holick M F, et al. (2005), "Prevalence of Vitamin D inadequacy among postmenopausal North American women receiving osteoporosis therapy". *J. Clin. Endocrinol. Metab.* 90:3215-24; Holick M F. (2006), "Resurrection of vitamin D deficiency and rickets". *J Clin Invest.* 116:2062-72; Holick M F, et al. (2008), "Vitamin D2 is as effective as vitamin D3 in maintaining circulating concentrations of 25-hydroxyvitamin D". *J Clin Endocrinol Metab.* 93: 677-81; "Weaver C M and Fleet J C. (2004), "Vitamin D requirements: current and future". *Am. J. Clin. Nutr.* 0(suppl): 1735S-9S; Lips P. (2001), "Vitamin D deficiency and secondary hyperparathyroidism in the elderly: consequences for bone loss and fractures and therapeutic implications". *Endocr Rev.* 22:477-501; Bischoff H A, et al. (2003), "Effects of vitamin D and calcium supplementation on falls: a randomized controlled trial". *J Bone Miner Res.* 18:343-51; Bischoff-Ferrari H A, et al. (2006), "Effect of cholecalciferal plus calcium on falling in ambulatory older men and women: a 3 year randomized controlled trial". *Arch Intern Med.* 166: 424-30; Snijder M B, et al. (2006), "Vitamin D status in relation to one-year risk of recurrent falling in older men and women". *J. Clin. Endocrinol. Metab.* 91:2980-5.]

In addition to its vital role in bone health, vitamin D has also been found to play a role in insulin, glucose, and inflammation regulation and may well be a warning sign for different cardiovascular and endocrine diseases including T2DM. There are vitamin D receptors in almost all the cells in the body, suggesting vitamin D plays a role in most chemical processes including beta cell function and regulation—the cornerstone of diabetes. The beta cells in the pancreas are responsible for producing and secreting insulin. In type 1 diabetes, the beta cells are destroyed by the body's immune system; in T2DM, the beta cells attempt to overproduce insulin due to increasing insulin resistance caused by a variety of factors. Vitamin D is present in beta cells and may affect insulin production and secretion as insulin secretion is dependent on calcium (and calcium absorption is dependent on vitamin D). Some animal studies demonstrated that removing vitamin D receptors, or creating a state of vitamin D deficiency, resulted in less insulin produced when needed; correcting vitamin D status restored proper insulin function. Researchers have also noted a deficiency in vitamin D possibly related to decreased insulin sensitivity, which is seen prior to and post T2DM diagnosis. In addition, vitamin D deficiency has been linked with an increase in parathyroid hormone, or hyperparathyroidism, which decreases insulin sensitivity as well. Thus supplementation to correct vitamin D deficiency may be a strategy for improvement of diabetes management, decreased risk of complications and overall health. [See e.g., Zeitz U, et al. (2003), "Impaired insulin secretory capacity in mice lacking functional vitamin D receptor". *Faseb Journal*, 17(3):509-11; Soares M J, et al. (2011), "Vitamin D and parathyroid hormone in insulin resistance of abdominal obesity: cause or effect?. *European Journal of Clinical Nutrition*, 65: 1348-1352; Chiu K C, et al. (2004), "Hypovitaminosis D is associated with insulin resistance and beta cell dysfunction". *Am. J. Clin. Nutr.* 79(5):820-5]

Certain co-factors are needed for the body to utilize vitamin D properly. Magnesium is the most important co-factor for vitamin D. In fact, it is common for rising vitamin D levels to exacerbate an underlying magnesium deficiency, which is associated with T2DM and obesity. Research has shown that low serum magnesium levels can be raised with vitamin D supplementation. [Farhanghi M A, et al. (2009), "Obesity induced magnesium deficiency can be treated by vitamin D supplementation". *J. Pak. Med. Assoc.* 59(4):258-61].

Vitamin K

Vitamin K (VK) is an essential, lipid-soluble vitamin that plays a vital role in the production of coagulation proteins to help blood clotting and preventing excessive bleeding. Vitamin K is actually a group of compounds. The most important of these compounds appears to be vitamin K1 and vitamin K2. Vitamin K1 (also known as phylloquinone or phytonadione) is obtained from leafy greens and some other vegetables. Vitamin K2 (menaquinone) is a group of compounds largely obtained from meats, cheeses, and eggs, and synthesized by the intestinal flora. In adults, Vitamin K deficiency is uncommon because of the intake of a wide variety of vegetables and other foods, the body's ability to recycle VK, and adequate gut flora production. Thus, unlike many other vitamins, VK is not typically used as a dietary supplement. An adult's daily requirement of VK has been estimated at 100-200 mcg/day, with the diet normally being a sufficient source.

Vitamin K acts as a cofactor, i.e., it is needed for the conversion of glutamic acid residues on the NH2-terminal of precursor coagulation proteins into the active form of γ-carboxyglutamic acid, which occurs via VK-dependent gamma-glutamyl carboxylase. This essential reaction allows the VK-dependent proteins to bind to surface phospholipids through calcium ion channel-mediated binding, in order to start the normal antithrombotic process. The major use of VK is treating and preventing bleeding problems in people with low levels of the blood clotting protein prothrombin and in newborns with low levels of vitamin K (hemorrhagic disease). VK is also used to reverse the effects of too much anti-coagulation caused by warfarin.

As discussed in parent U.S. application Ser. No. 15/649,084 filed on Jul. 13, 2017, anti-coagulation therapy with warfarin has been demonstrated to trigger vascular calcification by inhibiting the same essential reaction, i.e., activation of matrix Gla protein (MGP) via γ-carboxylation. MGP, which is synthesized by VSMCs, functions as a calcification inhibitor. For MGP to be functional in inhibiting soft-tissue calcification, vitamin K is required as an enzymatic cofactor in the γ-carboxylation of the protein. This role of vitamin K in vascular calcification has been demonstrated in animal, human and in vitro studies as cited in the above application. [See also Schurgers L J, et al. (2008), "Matrix Gla-protein: the calcification inhibitor in need of vitamin K". *Thromb. Haemost.* 100: 593-603.]

Aside from its established role in blood clotting, several studies support a critical function of vitamin K in improving bone health. As discussed above bone turnover involves the dynamic interplay of osteoclastic resorption and osteoblastic formation of bone matrix. Upon absorption of bone, osteoclasts undergo apoptosis, leaving a void that is then repaired by osteoblasts that are recruited to the area. When osteoblastic bone formation cannot keep up with the excavation of bone by osteoclasts, bone mineral density decreases. There are three proteins involved in bone formation that depend on vitamin K carboxylation: osteocalcin, matrix Gla protein, and protein S. All of these proteins are produced by osteoblasts and undergo activation via post translational carboxylation. Vitamin K is required for osteocalcin carboxylation, which in turn promotes normal bone mineralization. In general, vitamin K acts as a cofactor for the enzyme carboxylase, which catalyzes carboxylation of glutamic acid (Glu) residues to gamma carboxyglutamic acid in vitamin K dependent proteins. This reaction allows the protein to bind calcium ions with high affinity. In the case of osteocalcin, vitamin K dependent carboxylation allows the protein to bind to hydroxyapatite thereby regulating the growth of hydroxyapatite crystals.

Beyond the role of cofactor in carboxylation of bone proteins, vitamin K may have more direct actions on cells involved in bone formation. Animal studies have shown that Vitamin K promotes the transition of osteoblasts to osteocytes and also limits the process of osteoclastogenesis. Specifically, vitamin K2 has been shown to inhibit the expression of the osteoclast differentiation factor (ODF)/RANK ligand, tartrate-resistant acid phosphatase activity, and mononuclear cell formation, and to induce apoptosis in osteoclastic cells, thereby reducing the lifespan of osteoclasts and their ensuing lytic activity. Vitamin K2 also is a ligand for the xenobiotic nuclear receptor (SXR) and that binding leads to an increase in osteoblastic markers including alkaline phosphatase, osteopontin and matrix Gla protein. At a transcriptional level, vitamin K2 binding to the SXR domain may work in concert with estrogen receptor alpha to affect the differentiation of osteoblastic cells. It appears the effect of the binding results in formation of extracellular matrix proteins as well. It is believed there are also transcriptional modifications favoring bone formation that are completely independent of the SXR receptor region. [See e.g., Iwamoto J, et al. (2004), "Effects of vitamin K2 on osteoporosis". Curr. Pharm. Des. 10(21):2557-76; Kameda, T. et al. (1996), "Vitamin K inhibits osteoclastic bone resorption by inducing osteoclast apoptosis". *Biochemical and Biophysical Research Communications* 220:515-519; Koshihara Y and Hoshi K. (1997), "Vitamin K2 enhances osteocalcin accumulation in the extracellular matrix of human osteoblasts in vitro". *Journal of Bone and Mineral Research* 12:431-438; Tabb M M, et al. (2003), Vitamin K2 regulation of bone homeostasis is mediated by the steroid and xenobiotic receptor SXR". *Journal of Biological Chemistry* 278: 43919-43927; Igarashi M, et al. (2007), "Vitamin K induces osteoblast differentiation through pregnane x receptor-mediated transcriptional control of the msx2 gene". Molecular and Cellular Biology 27:7947-7954; Ichikawa T, et al. (2007), "Vitamin K2 induces phosphorylation of protein kinase a and expression of novel target genes in osteoblastic cells". *Journal of Molecular Endocrinology* 39:239-247; Palermo A, et al. (2017), "Vitamin K and osteoporosis: Myth or reality?". *Metabolism Clinical and Experimental,* 70:57-71; Plaza S M and Lamson D W (2005), "Vitamin K2 in bone metabolism and osteoporosis". *Altern. Med. Rev.* 10(1):24-35.]

TABLE 3

| Mode of Action and Mechanisms of Preferred Bio-actives Against OA | |
|---|---|
| Bio-actives | Mode of Action and Mechanism |
| Resveratrol | Significantly reduced OA severity, prevented type II collagen and proteoglycan degradation, increased collagen type II expression, and inhibited chondrocyte apoptosis in mice fed high fat diet [Gu H, et al. (2016), "Oral Resveratrol Prevents Osteoarthritis Progression in C57BL/6J Mice Fed a High-Fat Diet". *Nutrients* 8: 233]. Suppressed the AGEs mediated induction of iNOS and COX-2 expression and production of NO and PGE2, prevented AGEs induced degradation of collagen type II, and decreased AGEs induced expression and activity of MMP-13 by down regulating NF-κB and AP-1 signaling pathways [Liu FC, et al. (2010), "Chondroprotective effects and mechanisms of resveratrol in advanced glycation end products stimulated chondrocytes". *Arthritis Research & Therapy*, 12: R167]. Significantly reduced fibroblast growth factor (FGF) and IL-1β induced chondrocytes apoptosis, expression of cartilage degrading proteases (MMPs and aggrecanases) and decrease in proteoglycan biosynthesis by inducing bone morphogenic protein 7 (BMP7), downregulating catabolic transcription signaling, NF-κB, and MAPK and p53 [Im HJ et al. (2012), "Biological Effects of the Plant-derived Polyphenol Resveratrol in Human Articular Cartilage and Chondrosarcoma Cells". *J. Cell Physiol.* 227: 3488-349741]. Reduced chondrocyte apoptosis mediated by (a) an inhibition of proapoptotic protein B cell lymphoma 2 associated X protein (Bax), MMPs, and β-catenin, and (b) inducing the expression of antiapoptotic protein Bcl-2 and SIRT1 [Liu S, et al. (2017), "Sirt1 regulates apoptosis and extracellular matrix degradation in resveratrol-treated osteoarthritis chondrocytes via the Wnt/β-catenin signaling pathways". *Experimental and Therapeutic Medicine* 14: 5057-5062.8]. Resveratrol in combination with curcumin inhibited IL-1β induced chondrocytes apoptosis and suppression of collagen type II expression. The modulating benefit of curcumin plus resveratrol was mediated by (a) inducing a cartilage specific transcription factor, Sox9 (promoter of ECM expression); (b) inhibiting NF-kB activation; (c) inducing expression of antiapoptotic proteins (Bcl-2 and beclin); (d) suppressing proteases (MMPs) and proapoptotic proteins, including caspase-3 and poly(ADP-ribose) polymerase; and (e) downregulating β1-integrin expression [Shakibaei M (2011), *Ibid.*]. Resveratrol injection maintained expression of collagen type II, reduced the expression of iNOS and MMP-13 by stimulating SIRT1 and the inhibition of hypoxia induced factor-2α (HIF-2α) in OA cartilage of animal model and IL-1β treated human chondrocytes [Li W, et al. (2015), "Intra-Articular Resveratrol Injection Prevents Osteoarthritis Progression in a Mouse Model by Activating SIRT1 and Thereby Silencing HIF-2a". *J. Orthop. Res.* 33: 1061-1070]. Resveratrol delayed AC degradation, increased matrix synthesis, and reduced OA symptoms through mechanisms including (a) stimulating hypoxia induced factor-1α (HIF-1α), activating AMPK, and promoting autophagy (by increasing Beclin1, autophagy regulator), and (b) inhibiting mammalian target for rapamycin (mTOR) (associated with aging), HIF-2α, MMP-13, ADAMTS5 [Qin N, et al. (2017), "Local intra-articular injection of resveratrol delays cartilage degeneration in C57BL/6 mice by inducing autophagy via AMPK/mTOR pathway". *Journal of Pharmacological Sciences,* 134: 166-174.52]. Resveratrol inhibited RA development and progression by suppressing inflammation promoters, including IL-1β, TNF-α, NF-κB, COX2 and PGE2, MMPs, and arthritis index through induction of SIRT1 [de Brito Oliveira AL, et al. (2017), *Ibid.*; Hao L, et al. (2017), *Ibid.*]. Resveratrol significantly reduced knee swelling, histological score of synovial tissue, proliferating cell nuclear antigen (anti-PCNA), and proteins expressed by circulating microphages (CD 68, CD3) [Riveiro-Naveira RR, et al. (2016), "Resveratrol lowers synovial hyperplasia, inflammatory markers and oxidative damage in an acute antigen-induced arthritis model". *Rheumatology* 55: 1889-1900.] Resveratrol induced apoptosis of rheumatoid arthritis synovial fibroblast (RASF) significantly. This is mediated by caspase-dependent activation of caspase-9 and -3, poly ADPribose polymerase (PARP) cleavage and mitochondrial cytochrome c release, and/or caspase-independent [translocation of apoptosis-inducing factor (AIF) to the nucleus] signaling pathway [Byun HS, et al. (2008), "Caspase-8 has an essential role in resveratrol-induced apoptosis of rheumatoid fibroblast-like synoviocytes". *Rheumatology (Oxford)* 47: 301-308). |
| Curcumin | Prevented acute and chronic arthritis index, join swelling and cartilage destruction induced by peptidoglycan-polysaccharides administration by inhibiting NF-κB activation [Hao L, et al. (2017), *Ibid.*]. Inhibited IL-1β induced chondrocytes apoptosis, by suppressing caspase-3 expression/activation, enhancing autophagy, increasing anti-apoptotic proteins (Bcl-2 and Beclin-1) through ERK1/2 signaling activation [Chin KY (2016), "The spice for joint inflammation: anti-inflammatory role of curcumin in treating osteoarthritis". *Drug Design, Development and Therapy*; 10: 3029-3042; Li Z, et al. (2017), |

TABLE 3-continued

Mode of Action and Mechanisms of Preferred Bio-actives Against OA

| Bio-actives | Mode of Action and Mechanism |
|---|---|
| | "Curcumin Inhibits Apoptosis of Chondrocytes through Activation ERK1/2 Signaling Pathways Induced Autophagy". *Nutrients*, 9: 414].<br>Curcumin and resveratrol combination synergistically prevented IL-1β mediated chondrocytes apoptosis and stimulated collagen type II expression as described above under resveratrol [Shakibaei M (2011), *Ibid.*; Csaki C, et al. (2009), *Ibid.*]. |
| EGCG | Significantly decreased AGEs induced expression of TNF-α and MMP-13 in OA chondrocytes, which was mediated by inhibiting activation of p-38 mitogen activated protein kinase (p38-MAPK) and NF-κB [Rasheed Z, et al. (2009), "Green tea polyphenol epigallocatechin-3-gallate inhibits advanced glycation end product-induced expression of tumor necrosis factor-α and matrix mettaloproteinase-13 in human chondrocytes". *Arthritis Research and Therapy*, 11(3): 1-13].<br>Enhanced chondrocyte proliferation, production of collagen type II and aggrecan. These were mediated by suppression of chondrocytes hypertrophy, Sox9 (master transcription factor), and degradation of matrix proteins (mediated by MMPs and aggrecanases) [Huang H, et al. (2015), "Effect of EGCG on proliferation and phenotype maintenance in rabbit articular chondrocytes in vitro". *Exp. Ther. Med.* 9(1): 213-21851].<br>Inhibited IL-1β-induced IL-6 and IL-8 synthesis in RASF via suppressing transforming growth factor β activated kinase 1 (TAK1) [Sing AK, et al. (2016), "Regulation of TAK1 activation by epigallocatechin-3-gallate in RA synovial fibroblasts: suppression of K63-linked autoubiquitination of TRAF6". *Arthritis Rheumatol.* 68(2): 347-358.] |
| Magnesium | Reduced cartilage degradation and chondrocyte apoptosis deposition by blocking calcium from entering into chondrocyte cells and inhibiting calcium phosphate formation. This is mediated by magnesium's ability to act as an antagonist to the ion channel N-methyl-D-aspartate receptor(NMDAR), which regulates calcium's entry to the cells, and (b) decreasing inflammation [Lee CH, et al. (2009), "Intraarticular magnesium sulfate (MgSO4) reduces experimental osteoarthritis and nociception: association with attenuation of N-methyl-D-aspartate (NMDA) receptor subunit 1 phosphorylation and apoptosis in rat chondrocytes". *Osteoarthritis and Cartilage*, 17: 1485-1493; Zhang Y, et al. (2016), "Magnesium and osteoarthritis: from a new perspective". Annals of Joint, 1: 29]. |
| Procyanidins (Pcy) | Pcy and components of Pcy (procyanidin B2 and B3) slowed OA progression, indicated by reduction in OA symptoms, and proteoglycan, collagen type II degradation, MMPs and aggrecanases, and proinflammatory cytokines, in animal model by downregulating the expression and activation of vascular endothelial growth factor (VEGF), which is a mediator of OA progression [Wang A, et al. (2016), *Ibid.*]<br>Pcy B3 prevents cartilage degradation and heterotopic ossification (bone formation in the soft tissue around joint by inhibiting iNOS expression [Lee CH, et al. (2009), *Ibid.*]. |
| Hydroxytyrosol (HT) | Pretreatment of chondrocytes with HT (a) prevented chondrocytes apoptosis, DNA damage mediated, and (b) inhibited the increase in caspase activity, expression of INOS, COX-2, MMP-13, Runx2, and vascular endothelial growth factor (VEGF) levels, caused by either oxidative stress or oncogene α (GROα), which are known to cause OA development and promote hypertrophy [Facchini A., et al. (2014), *Ibid.*]<br>HT prevented degradation of cartilage matrix proteins and chondrocyte apoptosis by decreasing p62 expression and inducing autophagy mediated by an increase in SIRTI expression and activity [Chin KY and Pang KL (2017), "Therapeutic Effects of Olive and its Derivatives on Osteoarthritis: From Bench to Bedside". *Nutrients*].<br>HT treatment significantly increased the level of SIRT1 mRNA in the presence of GROα. An increase in SIRT1 has been shown to prevent chondrocyte apoptosis, ECM degradation, and mineralization, mediated via an increase in Runx2, MMP-13 and VEGF, inducing autophagy, and preventing mitochondrial dysfunction [Wang Y, et al. (2015), *Ibid.*; Facchini A., et al. (2014), *Ibid.*]<br>HT in combination with Pcy significantly reduced the severity of post-traumatic OA. Their action was mediated by significant reduction of inflammation via inhibition of PGE2, IL-1β, NO production, nitric oxide synthase (iNOS), COX2 and MMP-13 expression. [Mevel E, et al. (2016), "Olive and grape seed extract prevents post-traumatic osteoarthritis damages and exhibits in vitro anti IL-1β activities before and after oral consumption". *Scientific Reports* | 6: 33527 |]<br>HT plus Pcy prevented degradation of aggrecan (major proteoglycan in ECM) in post-traumatic induced OA [Mevel E, et al. (2016), *Ibid.*] |
| Quercetin | Quercetin significantly decreased severity of RA by inhibiting expression of microphage derived pro-inflammatory cytokines (TNF-α, IL-1β, MCP1), and iNOS [Mamani-Matsuda M, et al. (2006), "Therapeutic and preventive properties of quercetin in experimental arthritis correlate with decreased macrophage inflammatory mediators". *Biochemical pharmacology*; 72: 1304-1310].<br>Quercetin supplementation (a) reduced progression of RA as indicated by a reduction in arthritis score and paw swelling, (b) elastase activity, (c) oxidative stress and NO expression. These quercetin benefits were mediated by upregulating antioxidants expression and/or activation (glutathione (GS), superoxide dismutase (SOD) and catalase), and downregulating NF-κB, and COX2 expression [Ansari M and Khan HA (2014), *Ibid.*] |

TABLE 3-continued

Mode of Action and Mechanisms of Preferred Bio-actives Against OA

| Bio-actives | Mode of Action and Mechanism |
|---|---|
| | Quercetin supplementation significantly reduced NF-κB activity, IL-1β, CRP, monocyte chemotactic protein-1, and increased plasma antioxidant activity [Gardi C, et al. (2015), "Quercetin reduced inflammation and increased antioxidant defense in rat adjuvant arthritis". *Archives of Biochemistry and Biophysics*, 583: 150-157] |

Additional preferred bio-actives with joint health benefits include genistein, daidzein, lutein, zeaxanthin, apigenin, kaempferol, oleuropein, oleocanthal, hesperidin, rutin, beta-boswellic acid, rosmarinic acid, and gingerol.

Additional Therapeutic Agents

Preferably, the present compositions do not contain additional actives other than the preferred phytonutrients, vitamins and minerals described above since the compositions as formulated with these actives are therapeutically effective. However, in certain embodiments, the present compositions may comprise additional therapeutic agents to obtain an optimal effect. Thus, for example, the present compositions may comprise an additional agent such as other non-steroidal and steroidal anti-inflammatory agents, antioxidants, micronutrients and trace elements. Certain embodiments may also combine the present compositions with other therapeutic agents including prescription drugs for associated disorders such as anti-diabetic drugs like metformin; anti-hypertensives like thiazide diuretics and beta-blockers; anti-cholesterol drugs like statins; and analgesics.

Other anti-inflammatory agents may include, but are not limited to, lipoxygenase inhibitors, such as nordihydroguaiaretic acid; cyclo-oxygenase inhibitors such as flurbiprofen; and non-steroidal anti-inflammatory agents such as aspirin, ketorolac, flurbiprofen, ibuprofen, naproxen, indomethacin, ketoprofen, piroxicam, meclofenamic acid, rofecoxib, celecoxib, and mixtures thereof. If present, the other anti-inflammatory agents generally comprise from about 0.001% to about 5% by weight of the compositions of the present invention.

Modifiers of cell redox status include antioxidants such as N-acetyl cysteine and gallic acid; antioxidant enzyme inducers such as anethole-dithiothione, oltipraz, pyrrolidine dithiocarbamate (PDTC) and indole-3-carbinol. Other micronutrients include Co-enzyme Q10, pyrroloquinoline quinone (PQQ), thiamine, riboflavin, niacin, pantothenic acid, pyridoxine, choline, biotin, inositol, para-aminobenzoic acid. Trace elements include manganese, chromium, molybdenum, copper, selenium and combinations thereof.

Other Benefits

In addition to being beneficial for improving bone and joint health and against osteoporosis, OA and RA the present compositions comprising magnesium and phytochemicals such as quercetin, curcumin, reseveratrol and EGCG are beneficial against other aging-associated disorders, including neurodegenerative ones, such as dementia, Parkinson's disease and Alzheimer's disease (AD). A decline in a large spectrum of cognitive abilities including reasoning, memory, perceptual speed, and language is particularly prevalent with aging. The impairment of more of these activities, when lasting long enough and being associated to functional loss is referred to as dementia. AD is the most common and feared form of dementia representing about 70% of all dementia cases and displaying a dramatic epidemic due to increased life expectancy and an aging population. According to the World Alzheimer Report, dementia affects over 46 million people worldwide and this number is estimated to increase to 131.5 million by 2050. [Alzheimer's Disease International. (2016) "The Global Voice on Dementia".

Alzheimer disease is a multifactorial disease with genetic and environmental causes. The familial early-onset form of AD is caused by mutations in genes APP (amyloid precursor protein), PSEN1 (Presenilin 1) and PSEN2 (Presenilin 2). The pathology initiates in the hippocampus brain region that is involved in memory and learning, then progresses affecting the entire brain. Major pathological features of AD include the accumulation of extracellular amyloid plaques and fibrils, intracellular neurofibrillary tangles, as well as chronic inflammation, an abnormal increase of oxidative stress and disruption of cholinergic transmission, including reduced acetylcholine levels in the basal forebrain. The neurodegenerative process leads to synaptic damage, neuronal loss accompanied by astrogliosis and microglial cell proliferation, ultimately leading to brain dysfunction and marked atrophy in susceptible regions of the brain, such as the hippocampus, amygdale and basal forebrain Amyloid plaques, also known as "senile plaques", originate from the amyloid beta (Aβ) peptide, following up its aberrant cleavage by β-secretase, of the transmembrane protein amyloid precursor protein (APP), whose function is thought to be involved in neuronal development. Aβ monomers aggregate into soluble oligomers and coalesce to form insoluble fibrils deposited outside neurons in dense formations, the amyloid plaques, in less dense aggregates as diffuse plaques, and sometimes in the walls of small blood vessels in the brain. Small Aβ oligomers (40 and 42 aminoacids) are particularly toxic to neurons causing membrane damage, Ca leakage, oxidative damage, disruptions to insulin signaling pathways and synaptic function, and mitochondrial dysfunction Abnormal AP accumulation may be associated with disruption in cholinergic neurotransmission and initiate inflammatory mechanisms that produce reactive oxygen species (ROS). Abnormal release of neurotransmitters such as glutamate contributes to neuronal death and inflammation. There is direct evidence for free radical oxidative damage in brain of patients with AD. Oxidative stress is associated with various aspects of AD such as metabolic, mitochondrial, metal, and cell cycle abnormalities. Oxidative stress is evidenced by lipid peroxidation end products, formation of toxic peroxides, alcohols, free carbonyl, and oxidative modifications in nuclear and mitochondrial DNA. Neuroinflammation is also involved in the complex cascade leading to AD pathology and symptoms. It has been shown that AD is associated with increased levels of cyclooxygenase 1 and 2 and of prostaglandins, release of cytokines and chemokines, acute phase reaction, astrocytosis and microgliosis. These pro-inflammatory factors may induce degeneration of normal neurons through upregulation of nuclear factor-κB, mitogen-activated protein kinase, and c-Jun N-terminal kinase. Another feature observed in AD is abnormal aggregation of the tau protein (P-tau), a microtubule-associated protein expressed in neurons. P-tau acts to stabilize microtubules in the cell cytoskeleton. Like most microtubule-associated proteins, tau protein is normally regulated by phosphorylation; in AD patients, hyperphosphorylated P-tau accumulates as paired helical filaments that in turn aggregate into masses inside nerve cell bodies known as neurofibrillary tangles (NFTs), the other key pathological hallmark of AD. In summary, AD appears to be a complex and multifactorial disorder in which extracellular Aβ and intraneuronal hyperphosphorylated tau protein are the hallmark neuropathological features, along with oxidative stress and inflammation. Further, a recent longitudinal study reported significant longitudinal associations between long-term cognitive decline and high blood sugar levels and diabetes status.

Parkinson's disease is another chronic and progressive neurodegenerative malignancy that demonstrates chronic inflammatory responses mediating through increased accumulation of cellular free radicals, and oxidative damage to lipids, DNA and proteins. Parkinson's involves the malfunction and death of vital nerve cells called neurons. These dying neurons produce dopamine, a neurotransmitter that controls movement and coordination. Ultimately, affected persons are unable to control normal movement normally. [See e.g., Gabriela Mazzanti G and Di Giacomo S (2016), "Curcumin and Resveratrol in the Management of Cognitive Disorders: What Is the Clinical Evidence?". *Molecules*, 21(9):1243; P. Mecocci P, et al. (2014), "Nutraceuticals in cognitive impairment and Alzheimer's disease."*Front. Pharmacol.* 5:147; Gella A and Durany N (2009), "Oxidative stress in Alzheimer disease". *Cell Adh. Migr.* 3: 88-93; McGeer, P L and McGeer, E G, (2002), "Local neuroinflammation and the progression of Alzheimer's disease". *J. Neurovirol.* 8: 529-538; Steiner N, et al. (2015), "Neuroprotection of Neuro2a cells and the cytokine suppressive and anti-inflammatory mode of action of resveratrol in activated RAW264.7 macrophages and C8-B4 microglia". *Neurochem. Int.* 95: 46-54; Swaroop A and Bagchi D (Jan. 19, 2016), "Nutraceuticals and Functional Food Supplements for Brain Health".]

While all the factors that lead to the molecular cascade of neurodegeneration in dementia, Parkinson's and AD are not fully elucidated and because to date virtually no cure against these pathologies is known, interventions that prevent or at least delay the onset of neurodegeneration leading to cognitive impairment and dementia in older age are of tremendous significance. These interventions include natural nutrition and nutritional supplementation based on epidemiological and observational studies and clinical trials showing beneficial effects of regular consumption of certain plant-derived nutrients against age-related cognitive impairment and dementia. For example, curcumin, the most active element of tumeric (*Curcuma longa*) has been a staple of Indian diet and medicine for a long time. The prevalence of AD in Indian countries is much lower than in the US suggesting that a diet rich in curcumin is beneficial in reducing the risk of AD. Studies have also shown that a lower risk of dementia in subjects drinking moderate amounts of red wine when compared to abstainers. Red wine contains resveratrol, a polyphenol found enriched in seeds and skin of several fruits, including grapes used for red wine. Furthermore, a small clinical trial in healthy adults showed an increase of cerebral blood flow during cognitive tasks in subjects treated with resveratrol compared to placebo. Epidemiological observations in US and Finnish populations showed a reduced risk of Parkinson's disease in high consumers of tea and a reduced risk of cognitive impairment in a Japanese population drinking green tea. Black and green teas have a high content of catechins, EGCG being the most abundant. A large number of studies have also shown a protective activity against mild cognitive impairment (MCI) and AD of the Mediterranean diet, which is characterized by a moderate intake of wine and high consumption of plant foods (a source of the present phytochemicals such as quercetin, curcumin, reseveratrol, EGCG and oleuropein), fish and olive oil (as primary sources of monounsaturated fat). This kind of food intake pattern is believed to be particularly effective due to synergistic actions of its components. They act as potent antioxidants, as direct radical scavengers in lipid peroxidation, as anti-inflammatory and interact with and modulate critical signaling pathways, transcription factors and gene and/or protein expression in the brain structure. These activities result in inhibition of AP aggregation, reduction of oxidative stress, promotion of neuronal cell growth, inhibition of cholinesterase activity, inhibition of brain pro-inflammatory responses, prevention of neuronal cell death, up-regulation of the neuroprotective and longevity-linked gene sirtuin 1 activity among others, thus making them ideal actives against neurodegenerative diseases. [See e.g., Ogle W O, et al. (2013). "Potential of treating age-related depression and cognitive decline with nutraceutical approaches: a mini-review". *Gerontology* 59: 23-31 10; Ganguli M, et al. (2000), "Apolipoprotein E polymorphism and Alzheimer disease: The Indo-US Cross-National Dementia Study". *Arch. Neurol.* 57: 824-830; Orgogozo J M, et al. (1997), "Wine consumption and dementia in the elderly: a prospective community study in the Bordeaux area". *Rev. Neurol.* 153: 185-192; Kennedy D O, et al. (2010), "Effects of resveratrol on cerebral blood flow variables and cognitive performance in humans: a double-blind, placebo-controlled, crossover investigation". *Am. J. Clin. Nutr.* 91: 1590-1597; Panza F, et al. (2004), "Mediterranean diet and cognitive decline". *Public Health Nutr.* 7: 959-963; Calabrese V, et al. (2009), "Vitagenes, dietary antioxidants and neuroprotection in neurodegenerative diseases". *Front. Biosci.* 14: 376-397; Hu G, et al. (2007), "Coffee and tea consumption and the risk of Parkinson's disease". *Mov. Disord.* 22: 2242-2248; Kuriyama S, et al. (2006), "Green tea consumption and cognitive function: a cross-sectional study from the Tsurugaya Project 1". "*Am. J. Clin. Nutr.* 83: 355-361; Larson E B, et al. (2013), "New insights into the dementia epidemic". *New Engl. J Med.* 369: 2275-2277; Singh B, et al. (2013), "Association of Mediterranean diet with mild cognitive impairment and Alzheimer's disease: a systematic review and meta-analysis". *J. Alzheimers Dis.* 39: 271-282; Sofi F, et al. (2008), "Adherence to Mediterranean diet and health status: meta-analysis". *Brit. Med. J.* 337 a1344; Spencer J P (2009), "The impact of flavonoids on memory: physiological and molecular considerations". *Chem. Soc. Rev.* 38: 1152-1161; Spencer J P (2010), "Beyond antioxidants: the cellular and molecular interactions of flavonoids and how these underpin their actions on the brain". *Proc. Nutr. Soc.* 69: 244-260; Spencer J P, et al. (2008). Biomarkers of the intake of dietary polyphenols: strengths, limitations and application in nutrition research. *Brit. J. Nutr.* 99 12-22; Polidori M C, et al. (2012), "A review of the major vascular risk factors related to Alzheimer's disease". *J. Alzheimers Dis.* 32: 521-530; Polidori M C, et al. (2009), "High fruit and vegetable intake is positively correlated with antioxidant status and cognitive performance in healthy subjects". *J. Alzheimers Dis.* 17: 921-927; Polidori M C and Schulz R J. (2014), "Nutritional contributions to dementia prevention:

main issues on antioxidant micronutrients". *Genes Nutr.* 9: 382; Pocernich C B, et al. (2011), "Nutritional approaches to modulate oxidative stress in Alzheimer's disease". *Curr. Alzheimer Res.* 8: 452-469.]

The present compositions being also aimed toward normalizing metabolism and energy expenditure and managing oxidative stress and inflammation, are also beneficial in relation to physical activity, in particular performance, endurance, fatigue and recovery during intensive and/or continuous exercise/exertion or athletic activities.

Endurance performance during high intensity exercises is mainly determined by the capacity of the aerobic metabolism. It generally induces muscle fatigue defined as the reversible decline in skeletal muscle contractile performance. Fatigue is multifactorial and is often associated with many physiological parameters including reduced neural input and disruptive metabolic changes in skeletal muscles such as lactic acidosis and the production of oxidative free radicals. Moreover, it could lead to oxidative stress as a result of an imbalance between reactive oxygen species (ROS) production and intrinsic antioxidant defense. Therefore, improving performance and endurance would benefit from maintaining proper aerobic metabolism and inhibiting oxidative stress. The present compositions provide these benefits. Specifically, the present compositions activate both AMPK and Glut4. As discussed above, AMPK is a metabolic master switch that regulates downstream signals based on shifts in the surrounding energy reservoir. On activation, AMPK signals through its downstream substrates to achieve energy homeostasis by stimulating fatty acid oxidation and glucose transport, while inhibiting the opposing actions of fatty acid synthesis and protein synthesis. Thus, the net effect of AMPK activation is an increased cellular energy level via the inhibition of anabolic energy-consuming pathways, as well as the stimulation of catabolic, energy-producing pathways. Beyond energy homeostasis, AMPK plays a major role in glucose homeostasis by modulating glucose transport in peripheral tissues, in particular skeletal muscle. AMPK stimulates glucose uptake in skeletal muscle cells via increased expression of enzymes specialized in glucose uptake such as GLUT4 and hexokinase II. Moreover, AMPK directly phosphorylates the GLUT4 enhancer factor that is essential in the regulation of GLUT4 expression. Overall, these sequential alterations in the expression of enzymes involved in glucose uptake are the ultimate result of AMPK activation, which stimulates catabolic processes that counter the deleterious effects of glucose excess and maintains energy homeostasis. The importance of activating intracellular signaling pathways that involve AMPK and Glut4 to improve endurance capacity during exercise was demonstrated in a mouse study. This study found that that mice administered a black tea polyphenol combined with exercise training could run longer distances and for a longer time compared with the exercise only group. Intake of the polyphenol combined with exercise training increased phosphorylation of AMPK and mRNA level of glucose transporter 4 (GLUT4). [Eguchi T, et al. (2013), "Black Tea High-Molecular-Weight Polyphenol Stimulates Exercise Training-Induced Improvement of Endurance Capacity in Mouse via the Link between AMPK and GLUT4". *PLOS One* 8(7): e69480]

Many other animal and human studies have demonstrated the benefits from various flavonoids and polyphenols on physical activity particularly on athletic performance enhancement and sports nutrition. Among the phytonutrients that have been studied and found to be effective are quercetin, resveratrol, curcumin, green tea extract (GTE) and EGCG. Supplementation with these actives has been shown to correlate with prevention of aerobic exercise-induced muscle damage and inflammation, performance and endurance capacity. As discussed above, these phytonutrients exert a variety of biological activities often related to their antioxidant and anti-inflammatory nature, such as decreasing C-reactive protein, IL-6, and other cytokines and inflammatory biomarkers. In addition, these substances modulate a variety of biological and physiological processes including metabolic homeostasis, mitochondria biogenesis and skeletal muscle function. In animal studies, polyphenols including catechins, resveratrol, quercetin, and curcumin have been shown to activate sirtuins (especially SIRT1). SIRT1 activation modulates these processes. An animal study showed that 7 days quercetin treatment (12.5 or 25 mg/kg b.w.) increases the expression of genes associated with mitochondrial biogenesis (PPAR-$\gamma$ coactivator, PGC-1a and SIRT1), mitochondrial DNA content, and cytochrome-C concentration, both at muscle and brain levels in mice. Beside these biological data, quercetin-treated mice showed a significantly increased maximal endurance capacity (higher time to fatigue) and voluntary wheel-running activity, in a treadmill running test, compared with their placebo-treated counterparts. Another study found that treatment of 4-8 week-old male C57BL/6J mice with 0.4% (w/w) resveratrol significantly increased their aerobic capacity, as evidenced by an increased running time and higher oxygen consumption by muscle fibers via activation of SIRT1 and PGC1. Such effects are similar to the fatigue-resistant effect observed with tea polyphenols, such as ECGC. [See e.g., Myburgh K H, (2014), "Polyphenol Supplementation: Benefits for Exercise Performance or Oxidative Stress?". *Sports Med.* 44(Suppl 1): 57-70; Malaguti M, et al. (2013), "Polyphenols in Exercise Performance and Prevention of Exercise-Induced Muscle Damage". *Oxidative Medicine and Cellular Longevity*, 2013:825928, 9 pages; Davis J M, et al. (2010), "The dietary flavonoid quercetin increases $VO_{2max}$ and endurance capacity". *Int. J. Sport Nutr. Exerc. Metab.* 20(1):56-62; Lappalainen Z, (2011), "Sirtuins: a family of proteins with implications for human performance and exercise physiology, *Research in Sports Medicine*. 19(1); 53-65; Davis J M, et al. (2009), "Quercetin increases brain and muscle mitochondrial biogenesis and exercise tolerance". *American Journal of Physiology*, 296(4): R1071-R1077; Nieman D C, et al. (2010), "Quercetin's influence on exercise performance and muscle mitochondrial biogenesis". *Medicine and Science in Sports and Exercise*, 42(2): 338-345; Nieman D C, et al. (2009), "Effects of quercetin and egcg on mitochondrial biogenesis and immunity". *Medicine and Science in Sports and Exercise*, 41(7):1467-1475; Haramizu S, et al. (2011), "Catechins attenuate eccentric exercise-induced inflammation and loss of force production in muscle in senescence-accelerated mice". *Journal of Applied Physiology*, 111(6):1654-1663; Murase T et al. (2005), "Green tea extract improves endurance capacity and increases muscle lipid oxidation in mice". *American Journal of Physiology*, 288(3): R708-R715; S. Sae-Tan S, et al. (2011), "(−)-epigallocatechin-3-gallate increases the expression of genes related to fat oxidation in the skeletal muscle of high fat-fed mice". *Food and Function*, 2(2):111-116; Murase T, et al. (2009), "Suppression of the aging-associated decline in physical performance by a combination of resveratrol intake and habitual exercise in senescence-accelerated mice". *Biogerontology*, 10(4), 423-434; Lagouge M, et al, (2006), "Resveratrol improves mitochondrial function and protects against metabolic disease by activating SIRT1 and PGC-1$\alpha$". *Cell.* 127:1109-1122.]

Composition Use

A safe and effective amount of the compositions of the present invention comprising at least three phytonutrients optionally in combination with minerals and/or vitamins is typically administered to a subject having or at risk of developing arthritis (OA and/or RA) preferably from about once to four times per day, more preferably from about once to three times per day, even more preferably from about once per day to about twice per day. The period of such treatment typically can range from about one day to a lifetime. The subject may be any person or animal in need of treatment or prevention. By "animal" is meant to include in particular household pets or other domestic animals, or animals kept in captivity.

The present compositions preferably comprise magnesium mineral in combination with three or more of phytonutrients selected from quercetin, rutin (quercetin-3-O-rutinoside), curcumin, resveratrol, EGCG, oleuropein, hydroxytyrosol, genistein, daidzein. hesperidin, hesperitin, magnolol/honokiol, amorfrutins, *Salacia* extract (source of mangiferin, salacinol and kotalanol), and *Acacia* polyphenols (source of robinetinidol, fisetinidol, catechin and gallocatechin), lutein, zeaxanthin, apigenin, kaempferol, oleocanthal, and gingerol as active agents. The concentrations of the actives in the present compositions and delivered dosage of individual agents will vary depending on the type/form of composition, the intended purpose, and the gender and target age groups. Generally, each phytonutrient will be present at least about 5 mg in the composition, at least about 10 mg in some embodiments at least about 50 mg in other embodiments and up to about 3000 mg. However, since the present compositions contain a combination of these phytonutrients having multiple activities, only smaller amounts of each phytonutrient are generally used. For example, the preferred daily dose range for quercetin is from about 10 mg to about 3,000 mg, more preferably from about 300 mg to about 2,200 mg, even more preferably from about 500 mg to about 1,500 mg. For curcumin, the preferred daily dosage is from about 10 mg to about 1,500 mg, more preferably from about 300 mg to about 1,300 mg and even more preferably 500 mg to 1000 mg. For resveratrol, EGCG, hydroxytyrosol, procyanidins and magnolol/honokiol the preferred daily dosage is from about 5 mg to about 500 mg, more preferably about 15 mg to about 350 mg and even more preferably about 100 mg to about 300 mg. For hesperidin, the preferred daily dose is from about 5 to about 1000 mg, more preferably about 50 to about 500 mg and even more preferably about 75 to about 300 mg. For magnesium, the preferred daily dosage is from about 50 mg to about 1000 mg, more preferably from about 100 mg to about 500 mg and even more preferably from about 200 mg to about 400 mg. For Vitamin D the preferred daily dosage is from about 5 mcg to about 800 mcg, preferably from about 250 mcg to about 400 mcg. Vitamin K is optionally utilized in the compositions from about 10 to about 300 mcg. The compositions may be formulated for daily, weekly or monthly dosing. Preferably the compositions are formulated for daily dosing taken 1 to 4 times a day for ease of compliance in easy to swallow pills and capsules, chews, drink mixes and beverages.

The following non-limiting examples further describe preferred embodiments within the scope of the present invention. The examples are given solely for illustration and are not to be construed as limitations of this invention as many variations thereof are possible without departing from the spirit and scope thereof.

EXAMPLES

Example I. Efficacy Testing of Dietary Supplements

The benefits from the present compositions comprising phytonutrients and magnesium as active agents are demonstrated in (1) an in vitro study using human osteoarthritis (OA) cartilage explant cultures and chondrocyte monolayer cultures to assess the effect of the present compositions on (a) proteoglycan and extracellular matrix (ECM) synthesis; (b) secretion of matrix metalloproteins (MMPs), proteases that degrade collagen and proteoglycan in OA and (c) expression of apoptotic markers as a measure of apoptosis of chondrocytes and (2) an in vivo feeding study using C57BL/6J mice to assess the effect of supplementation with the present compositions on osteoarthritis development and/or progression by assessing (a) degradation of cartilage by measuring C-telopeptide of type II collagen (CTX-II); (b) Type II collagen expression; (c) severity of OA using a Mankin scoring system; and (d) chondrocyte apoptosis using TUNEL. The treatment products in each study comprise as actives magnesium and phytonutrients. The treatment products may include optional ingredients such as vitamins, other minerals, SAM-e, glucosamine, and chondroitin.

The experimental procedure in the in vitro cell study is as described in the literature with some modification. [Dave M et al. (2008), "The Antioxidant Resveratrol Protects Against Chondrocyte Apoptosis Via Effects on Mitochondrial Polarization and ATP Production". *Arthritis Rheum.* 58(9):2786-97; Attur M G, et al. (2000), "Reversal of autocrine and paracrine effects of interleukin 1 (IL-1) in human arthritis by type II IL-1 decoy receptor: potential for pharmacological intervention". *J. Biol. Chem.* 275: 40307-15]. Human articular cartilage (AC) samples are obtained from patients with advanced OA to prepare explant AC culture discs and chondrocyte monolayer cultures. For all studies, the cultures are adapted to serum-free conditions. Cultures are treated with control and test compositions and interleukin-1β (IL-1β), which induces production of prostaglandin $E_2$ (PGE$_2$) and leukotriene $B_4$ (LTB$_4$) in chondrocytes. At the end of each experiment, culture supernatants are removed and stored at −20° C. until being analyzed by ELISA or radio-immunoassay (RIA). Monolayer and explant cultures are harvested for analyses of gene expression, COX activity, proteoglycan synthesis, mitochondrial staining, levels of MMPs or expression of apoptotic markers.

The experimental procedure in the in vivo study is as described in the literature with some modification [Gu H, et al. (2016), "Oral Resveratrol Prevents Osteoarthritis Progression in C57BL/6J Mice Fed a High-Fat Diet". *Nutrients*, 8:233; Jiang M, et al. (2017), "Oral Administration of Resveratrol Alleviates Osteoarthritis Pathology in C57BL/6J Mice Model Induced by a High-Fat Diet". *Mediators of Inflammation*, Article ID 7659023, 11 pages]. Seven week old male 7BL/6J mice (supplied by Jackson Laboratories, Bar Harbor, Me.) are randomly divided into groups to establish control groups and test groups. Mice in the control groups are fed control formulations: (a) standard mouse diet (SMD) with 10% of calories from fat and (b) high fat diet (HFD) with 58% of calories from fat. Test groups are fed HFD+phytonutrient/mineral compositions according to the present invention. Diets and water are available ad libitum and all of the animals received their respective diets every day for 12 weeks. Body weight and the amount of food intake are recorded each week. Mice are maintained under a constant temperature of 20±2° C., a relative humidity of 50%±10%, and a 12 h light/dark cycle. Animal experimental procedures are conducted according to an approved animal protocol. All mice are sacrificed after 12 weeks. Blood samples are collected from the abdominal aorta, centrifuged and stored. Levels of serum C-telopeptide of type II collagen (CTX-II), indicator of cartilage degradation will are determined by ELISA. Severity of OA of the left joints will be measured by using a staining method. Histological evaluation of stained cartilage is performed by calculating modified Mankin scores. Type II collagen synthesis is determined by using anti-mouse type II collagen antibody. Chondrocyte apoptosis is measured by using the TUNEL assay, a method for detecting apoptotic DNA fragmentation to identify and quantify apoptotic cells, or to detect excessive DNA breakage in individual cells. The assay relies on the use of terminal deoxynucleotidyl transferase (TdT), an enzyme that catalyzes attachment of deoxynucleotides, tagged with a fluorochrome or another marker, to 3'-hydroxyl termini of DNA double strand breaks.

The dimensions and values disclosed herein are not to be understood as being strictly limited to the exact numerical values recited. Instead, unless otherwise specified, each such dimension is intended to mean both the recited value and a functionally equivalent range surrounding that value. For example, a value or amount disclosed as "40 mg" is intended to mean "about 40 mg".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition effective to treat or reduce development and/or progression of osteoarthritis (OA) and/or rheumatoid arthritis (RA) in human and other mammalian subjects, said composition consisting of a combination of:
   magnesium (Mg) mineral supplied as a chloride, sulfate, carbonate, oxide, citrate, malate, aspartate, glutamate, taurate, or bisglycinate compound or complex;
   procyanidins;
   curcumin;
   resveratrol;
   epigallocatechin-3-gallate (EGCG); and
   optionally, one or more inactive ingredients selected from the group consisting of excipients, carriers, flavoring agents, preservatives, and colorants,
   wherein each of the procyanidins, curcumin, resveratrol, and EGCG are present in an amount of from about 5 mg to about 3000 mg and the magnesium is present in an amount of from about 50 mg to about 1000 mg.

2. A composition according to claim 1, formulated as a dietary or nutritional supplement in a form selected from capsules, tablets, pills, gummies, gelcaps, granules, powder, teas, drink mixes and beverages.

3. A method of treating or reducing development and/or progression of osteoarthritis (OA) and rheumatoid arthritis (RA) comprising administering to humans and other mammalian subjects a composition consisting of:
   magnesium (Mg) mineral supplied as a chloride, sulfate, carbonate, oxide, citrate, malate, aspartate, glutamate, taurate, or bisglycinate compound or complex;
   procyanidins;
   curcumin;
   resveratrol;
   epigallocatechin-3-gallate (EGCG);
   optionally, one or more inactive ingredients selected from the group consisting of excipients, carriers, flavoring agents, preservatives, and colorants;
   wherein each of the procyanidins, curcumin, resveratrol, and EGCG are present in an amount of from about 5 mg to about 3000 mg and the magnesium is present in an amount of from about 50 mg to about 1000 mg.

4. The method according to claim 3, wherein the composition is administered as a dietary or nutritional supplement in a form selected from capsules, tablets, pills, gummies, gelcaps, granules, powder, teas, drink mixes and beverage.

5. The method according to claim 3, wherein the composition is administered one to four times daily.

6. The composition according to claim 1, wherein the magnesium is present in the composition as magnesium oxide.

7. The composition according to claim 1, wherein the magnesium is present in the composition as di-magnesium malate.

8. The composition according to claim 1, wherein the magnesium is present as magnesium oxide and di-magnesium malate.

9. The method according to claim 3, wherein the magnesium is present in the composition as magnesium oxide.

10. The method according to claim 3, wherein the magnesium is present in the composition as di-magnesium malate.

11. The method according to claim 3, wherein the magnesium is present as magnesium oxide and di-magnesium malate.

* * * * *